(12) United States Patent
Keefe

(10) Patent No.: US 8,840,565 B2
(45) Date of Patent: *Sep. 23, 2014

(54) TEST BATTERY SYSTEM AND METHOD FOR ASSESSMENT OF AUDITORY FUNCTION

(75) Inventor: Douglas H. Keefe, Omaha, NE (US)

(73) Assignee: Sonicom, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/569,849

(22) Filed: Aug. 8, 2012

(65) Prior Publication Data

US 2012/0302859 A1 Nov. 29, 2012

Related U.S. Application Data

(63) Continuation of application No. 11/885,919, filed as application No. PCT/US2006/009418 on Mar. 16, 2006, now Pat. No. 8,241,224.

(60) Provisional application No. 60/662,256, filed on Mar. 16, 2005.

(51) Int. Cl.

| A61B 5/00 | (2006.01) |
|---|---|
| A61B 5/12 | (2006.01) |
| H04R 1/28 | (2006.01) |
| G01D 7/00 | (2006.01) |
| G01C 3/08 | (2006.01) |
| A61F 5/56 | (2006.01) |
| A61B 19/00 | (2006.01) |

(52) U.S. Cl.
CPC ..................................... *A61B 5/121* (2013.01)
USPC ................. 600/559; 73/585; 73/586; 73/587; 73/645; 73/646; 73/647; 73/648; 128/848; 128/897; 128/898

(58) Field of Classification Search
USPC ........... 73/585, 586, 587, 645, 646, 647, 648; 128/848, 897, 898; 600/559
See application file for complete search history.

(56) References Cited

U.S. PATENT DOCUMENTS

| 4,014,320 A | 3/1977 | Richards |
|---|---|---|
| 4,029,083 A | 6/1977 | Baylor |

(Continued)

FOREIGN PATENT DOCUMENTS

| CA | 2191442 | 6/1995 |
|---|---|---|
| EP | 0 957 764 | 11/1999 |

(Continued)

OTHER PUBLICATIONS

U.S. Appl. No. 60/662,256, filed Mar. 16, 2005, Keefe.

(Continued)

*Primary Examiner* — Sean Dougherty
(74) *Attorney, Agent, or Firm* — Mueting, Raasch & Gebhardt, P.A.

(57) ABSTRACT

A test battery method and system for use in assessing auditory function (e.g., the screening or diagnosis of impairments, fitting of hearing aids, etc.) is provided which performs one or more auditory tests including, for example, an acoustic reflectance test. Such an acoustic reflectance test may be a reflectance tympanometry test that includes a feedback system to control static pressure in the ear canal. Such acoustic reflectance tests may be used alone or in combination with one or more other auditory tests. Further, for example, such a battery of tests may include middle-ear muscle reflex tests in combination with one or more other auditory or hearing tests.

22 Claims, 15 Drawing Sheets

(56) References Cited

U.S. PATENT DOCUMENTS

| | | | |
|---|---|---|---|
| 4,237,905 A | 12/1980 | Keller et al. | |
| 4,459,996 A | 7/1984 | Teele | |
| 4,548,082 A | 10/1985 | Engebretson et al. | |
| 4,601,295 A | 7/1986 | Teele | |
| 4,688,582 A | 8/1987 | Heller et al. | |
| 5,594,174 A | 1/1997 | Keefe | |
| 5,601,091 A | 2/1997 | Dolphin | |
| 5,651,371 A | 7/1997 | Keefe | |
| 5,697,379 A | 12/1997 | Neely et al. | |
| 5,699,809 A | 12/1997 | Combs et al. | |
| 5,738,633 A | 4/1998 | Christiansen | |
| 5,792,072 A | 8/1998 | Keefe | |
| 5,792,073 A | 8/1998 | Keefe | |
| 5,885,225 A | 3/1999 | Keefe et al. | |
| 5,916,174 A | 6/1999 | Dolphin | |
| 6,126,614 A | 10/2000 | Jenkins et al. | |
| 6,139,507 A | 10/2000 | Jeng | |
| 6,602,202 B2 | 8/2003 | John et al. | |
| 6,837,857 B2* | 1/2005 | Stirnemann | 600/559 |
| 6,866,639 B2 | 3/2005 | Causevic et al. | |
| 6,964,642 B2 | 11/2005 | Wasden et al. | |
| 6,974,421 B1 | 12/2005 | Causevic et al. | |
| 7,416,531 B2* | 8/2008 | Mohler | 600/528 |
| 7,715,577 B2* | 5/2010 | Allen et al. | 381/312 |
| 8,241,224 B2 | 8/2012 | Keefe | |
| 2003/0144603 A1 | 7/2003 | Zoth et al. | |
| 2004/0006283 A1 | 1/2004 | Harrison et al. | |
| 2004/0039299 A1 | 2/2004 | Harrison et al. | |
| 2004/0152998 A1 | 8/2004 | Stott et al. | |
| 2005/0015018 A1 | 1/2005 | Dolphin et al. | |
| 2005/0033193 A1 | 2/2005 | Wasden et al. | |
| 2006/0083395 A1 | 4/2006 | Allen et al. | |
| 2006/0093395 A1* | 5/2006 | Igarashi et al. | 399/101 |
| 2007/0161924 A1 | 7/2007 | Dolphin et al. | |

FOREIGN PATENT DOCUMENTS

| | | |
|---|---|---|
| EP | 1042726 | 10/2000 |
| EP | 0 853 462 B1 | 12/2002 |
| EP | 1 275 340 A1 | 1/2003 |
| WO | WO 95/33405 | 12/1995 |
| WO | WO 97/04704 | 2/1997 |
| WO | WO 97/20501 | 6/1997 |
| WO | WO 99/040533 A1 | 8/1999 |
| WO | WO 00/65983 | 11/2000 |
| WO | WO 03/099121 A2 | 12/2003 |
| WO | WO 2004/027981 A2 | 4/2004 |
| WO | WO 2004/105607 A2 | 12/2004 |
| WO | WO 2005/072605 A1 | 8/2005 |
| WO | WO 2007/084674 A2 | 7/2007 |

OTHER PUBLICATIONS

U.S. Appl. No. 60/619,517, filed Oct. 15, 2004, Allen (MIMOSA).

U.S. Appl. No. 60/473,297, filed May 23, 2003, Dolphin et al.

Allen et al., "Evaluation of human middle ear function via an acoustic power assessment," *Journal of Rehabilitation Research & Development*, Jul./Aug. 2005;42(4):Supplement 2:63-78 [online]. Retrieved on Mar. 13, 2006. Retrieved from the Internet<URL:http://www.vard.org.jour/05/42/4%20Suppl%202/Allen.html>; 14 pgs.

Blayney et al., "An experimental technique for determining middle ear impedance," *Acta Otolaryngol*, 1996; 116:201-204.

Carney, Laurel, "Psychological and Physiological Acoustics: Auditory Periphery and Models," *J Acoust Soc Am.*, May 2004; 115(5)Pt. 2, 147th Meeting: Acoustical Society of America: 2499.

Chan and Geisler, "Estimation of eardrum acoustic pressure and of ear canal length from remote points in the canal," *J Acoust. Soc. Am.*, 1990; 87:1237-1247.

Communication pursuant to Article 94(3) EPC dated Jul. 24, 2008 for European Application No. 06 738 478.4; 11 pgs.

Dirks, "Bone-conduction threshold testing," *Handbook of Clinical Audiology*, Chapter 9, 4th Edition, Williams & Wilkins, Baltimore, MD, 1994, pp. 132-146.

Gibson, Andrea, "New Hearing Test can Improve Diagnosis of Middle Ear Disorders," HearingCenterOnline.Com, [online] 2005. [retrieved on Feb. 9, 2006]. Retrieved from the Internet:<URL:http://www.hearingcenteronline.com/newsletter.july00m.shtml>; 2 pgs.

Gorga et al., "Identification of Neonatal Hearing Impairment: Distortion Product of Otoacoustic Emissions during the Perinatal Period," *Ear & Hearing*, Oct. 2000; 21(5):400-424.

Hall et al., "Tympanometry in Clinical Audiology," *Handbook of Clinical Audiology*, Chapter 20, 4th Edition, Williams & Wilkins, Baltimore, MD, 1994, pp. 283-299.

Huang et al., "A noninvasive method for estimating acoustic admittance at the tympanic membrane," *J Acoust Soc. Am.*, 2000; 108:1128-1146.

Hunter et al., "Safety and Clinical performance of acoustic reflex tests," *Ear and Hearing*, 1999; 20:506-514.

International Preliminary Report on Patentability and Written Opinion for Application No. PCT/US2006/009418 dated Sep. 9, 2007; 14 pgs.

International Search Report for Application No. PCT/US2006/009418 dated Jan. 4, 2007; 8 pgs.

Jeng, Patricia,"A Wide-band Reflectance—DPOAE (WR-DP) Screener," Grant Abstract, Grant No. 1R43DC006554-01 [online]. National Institute on Deafness and other Communication Disorders, project dates Mar. 1, 2004 to Aug. 1, 2004 [retrieved on Jan. 31, 2006]. Retrieved from the Internet<URL:http://crisp.cit.nih.gov/crisp/CRISP_LIB.getdoc?textkey=6736192&p_num=1R43D...>; 2 pgs.

Jeng, Patricia, "A Wide Band Reflectance—DPOAE (WR-DP) Screener," Grant Abstract, Grant No. 2R44DC006554-02 [online]. National Institute on Deafness and other Communication Disorders, project dates Mar. 1, 2004 to Dec. 31, 2006 [retrieved on Jan. 31, 2006]. Retrieved from the Internet<URL:http://crisp.cit.nih.gov/crisp/CRISP_LIB.getdoc?textkey=6884335&p_num=2R44D...>; 2 pgs.

Jeng, Patricia, "A wide band Reflectance—DPOAE (WR-EP) Screener," Grant Abstract, Grant No. 5R44DC006554-03 [online]. National Institutes on Deafness and Other Commuication Disorders, project dates Mar. 1, 2004 to Dec. 31, 2006 [retrieved on Oct. 19, 2007]. Retrieved from the Internet<URL:http://crisp.cit.nih.gov/CRISP_LIB.getdoc?textkey=7001269&p_Grant_num=5R44DC006554-03&p_query&ticket=47816591&p_audit_session_id=271566830&p_keywords=>; 2 pgs.

Jeng, Patricia, "Acoustical Power Flow as an Audiological Tool" Grant Abstract, Grant No. 2R44DC003138-02 [online]. National Institute on Deafness and other Communication Disorders, project dates Sep. 1, 1996 to May 31, 2002 [retrieved on Jan. 31, 2006]. Retrieved from the Internet<URL:http://crisp/cit.nih.gov/CRISP_LIB.getdoc?textkey=2801447&p_num=2R44D...>; 2 pgs.

Jeng, Patricia, "Acoustical Power Flow as an Audiological Tool," Grant Abstract, Grant No. 3R44DC003138-02S1 [online]. National Institute on Deafness and other Communication Disorders, project dates Sep. 1, 1996 to May 2002 [retrieved on Jan. 31, 2006]. Retrieved from the Internet:<URL:http://crisp/citnih.gov/CRISP_LIB.getdoc.?textkey=6499974&p_num=3 R44D...; 2 pgs.

Jeng, Patricia, "Acoustical Power Flow as an Audiological Tool," Grant Abstract, Grant No. 5R44DC003138-03 [online]. National Institute on Deafness and other Communication Disorders, project dates Sep. 1, 1996 to May 31, 2004 [retrieved on Jan. 31, 2006]. Retrieved from the Internet:<URL:http://crisp.cit.nih.gov/CRISP_LIB.getdoc?textkey=6175405&p_num=5R44D...>; 2 pgs.

Keefe et al., "Session HH. Psychological and Physiological Acoustics VIII: Ear Canal Measures and Hearing Impairment. HH1. Auditory system impedance measurement using the two-microphone wavetube technique," *J Acoust. Soc. Am.*, 113th Meeting: Acoustical Society of America. May 14, 1987; 81:S75.

Keefe et al., "Method to measure acoustic impedance and reflection coefficient," *J Acoust. Soc. Am.*, 1992; 91:470-485.

Keefe et al., "Ear-canal impedance and reflection coefficient in human infants and adults," *J Acoust Soc Am.*, 1993; 94:2617-2638.

Keefe and Levi, "Maturation of the middle and external ears: Acoustic power-based responses and reflectance tympanometry," *Ear and Hearing*, 1996; 17:361-373.

(56) References Cited

OTHER PUBLICATIONS

Keefe, "Otoreflectance of the cochlea and middle ear," *J Acoust Soc. Am.*, 1997; 102:2849-2859.

Keefe et al., "Identification of Neonatal Hearing Impairment: Ear-Canal Measurements of Acoustic Admittance and Reflectance in Neonates," *Ear & Hearing*, Oct. 2000; 21(5):443-461.

Keefe et al., "Ear-canal acoustic admittance and reflectance effects in human neonates. I: Predictions of otoacoustic emission and auditory brainstem responses," *J Acoust. Soc. Am.*, 2003; 113:389-406.

Keefe et al., "Ear-canal acoustic admittance and reflectance measurements in human neonates. II: Predictions of middle-ear dysfunction and sensorineural hearing loss," *J. Acoust. Soc. Am.*, 2003; 113:407-422.

Keefe and Simmons, "Energy transmittance predicts conductive hearing loss in older children and adults," *J Acoust. Soc. Am.*, 2003; 114:3217-3238.

Keefe, DH., "Using reflectance phase to esimate the acoustic response at the tympanic membrane," *J Acoust Soc. Am.*, 2005;115:2499(A).

Keefe, "Influence of middle-ear function and pathology on otoacoustic emissions," *Otoacoustic Emissions: Clinical Applications*, Third Ed., Chapter 7, New York 2007, 78 pgs.

Keefe, Douglas H., "Acoustic Responses of the Human Cochlea and Middle Ear," Grant Abstract, Grant No. 5R01DC003784-09 [online]. National Institutes on Deafness and Other Communication Disorders, project dates May 1, 1999 to Feb. 28, 2009 [retrieved on Nov. 13, 2007]. Retrieved from the Internet<URL:http://crisp.cit.nih.gov/crisp/CRISP_LIB/getdoc?textkey=7174621&p_grant_num=5R01DC003784-09&p_query=&ticket=49915116&p_audit_session id=276355757&p_keywords=>; 1 page.

Keefe, Douglas H., "Otoreflectance Assessment of Middle-Ear Functioning," Grant Abstract, Grant No. R41 DC006607 [CRISP online]. National Institute on Deafness and Other Communication Disorders, project dates Sep. 26, 2003 to Feb. 28, 2005, pp. 1-2.

Keefe, Douglas H., "Otoreflectance Assessment of Middle-Ear Functioning," Grant Abstract, Grant No. 2R42 DC006607-02 [CRISP online]. National Institute on Deafness and Other Communication Disorders, project dates Sep. 26, 2003 to Aug. 31, 2007, pp. 3-4.

Keefe, Douglas H., "Otoreflectance Assessment of Middle-Ear Functioning," Grant Abstract, Grant No. 5R42 DC006607-03 [CRISP online]. National Institute on Deafness and Other Communication Disorders, project dates Sep. 26, 2003 to Feb. 29, 2008, pp. 5-6.

Levitt, H., "Compression Amplification," *Compression: from Cochlea to Cochlear Implants*, Chapter 5, Springer-Verlag, New York, NY, 2004, pp. 153-183.

Lim et al., "Recent Advances in Otitis Media; Report of the Eighth Research Conference, Chapter 7: Diagnosis and Screening," *Annals of Otology, Rhinology, and Laryngology*, Jan. 2005, Part 2, Supplement 194, vol. 114(1):104-113.

Margolis et al., "Wideband reflectance tympanometry in normal adults," *J Acoust Soc Am*, 1999; 106:265-280.

Margolis et al., "Wideband reflectance tympanometry in chinchillas and humans," *J Acoust Soc Am*, 2001; 110:1453-1464.

Moulin et al., "Contralateral auditory stimulation alters acoustic distortion products in humans," *Hearing Research*, 1993; 65:193-210.

Müller-Wehlau et al., "The effects of neural synchronization and peripheral compression on the acoustic-reflex threshold," *J Acoust Soc Am.*, May 2005; 117(5):3016-3027.

Neumann et al., "Detection of the acoustic reflex below 80 dB HL," *Audiol. Neuro-Otol.*, 1996; 1:359-369.

Northern et al., "Tympanometry in Clinical Audiology," Handbook of Clinical Audiology, Chapter 21, 4$^{th}$ Edition, Williams & Wilkins, Baltimore, MD, 1994, pp. 300-315.

Norton et al., "Identification of Neonatal Hearing Impairment: Evaluation of Transient Evoked Otoacoustic Emission, Distortion Product Otoacoustic Emission, and Auditory Brain Stem Response Test Performance," *Ear & Hearing*, Oct. 2000; 21(5):508-528.

Perez, Moises, "Biomedical Acoustics: Designing a Probe for in Ear Signal Acquisition and Interpretation of Hearing Health," *University of Miami, College of Engineering*, EEN 502, Literature Project, Fall 2004, Submitted: Dec. 2, 2004.

Petrak, Michelle, "Tympanometry Beyond 226 Hz—What's Different in Babies?" Audiology Online, [online]. Nov. 18, 2002. [retrieved on Feb. 9, 2006]. Retrieved from the Internet: <URL:http://www.audiologyonline.com/articles/arc_disp.asp?article_id=393>; 5 pgs.

Ryan and Piron, "Functional maturation of the medial efferent olivocochlear system in human neonates," *Acta Otolaryngol*, Sep. 1994; 114(5):485-489.

Sininger et al., "Identification of Neonatal Hearing Impairment: Auditory Brain Stem Responses in the Perinatal Period," *Ear & Hearing*, Oct. 2000; 21(5):383-399.

Stinson, "Estimation of acoustical energy reflectance at the eardrum from measurements of pressure distribution in the human ear canal," *J. Acoust. Soc. Am.*, Sep. 1982; 72:766-733.

Stinson and Khanna, "Sound propagation in the ear canal and coupling to the eardrum with measurements on model systems," *J. Acoust. Soc. Am.*, Jun. 1989; 85:2481-2491.

Ware et al., "Continuous and discrete inverse-scattering problems in a stratified elastic medium. I. Plane waves at normal incidence," *J Acoust. Soc. Am.*, Sep. 9, 1968; 45(4):911-921.

Widen et al., "Identification of Neonatal Hearing Impairment: Hearing Status at 8 to 12 Months Corrected Age Using a Visual Reinforcement Audiometry Protcol," *Ear & Hearing*, Oct. 2000; 21(5):471-487.

Yantis, "Puretone airconduction threshold testing," *Handbook of Clinical Audiology*, Chapter 7, 4$^{th}$ Edition, Williams & Wilkins, Baltimore, MD, 1994.

\* cited by examiner

TEST BATTERY SYSTEM AND METHOD FOR ASSESSMENT OF AUDITORY FUNCTION

CROSS-REFERENCE TO RELATED APPLICATION

This application is a continuation application of U.S. application Ser. No. 11/885,919 filed on 20 Mar. 2008 which is the §371 U.S. National Stage of International Application No. PCT/US2006/009418, filed 16 Mar. 2006, which claims the benefit of U.S. Provisional Application No. 60/662,256 entitled "ASSESSMENT OF PERIPHERAL AUDITORY FUNCTION USING TEST BATTERY SYSTEM INCLUDING AN ACOUSTIC REFLECTANCE TEST," filed 16 Mar. 2005, all of which are incorporated herein by reference in their entirety.

STATEMENT OF GOVERNMENT RIGHTS

The present invention was made with support under NIH Grant No. R41 DC006607 awarded by the NIDCD, an institute of the National Institutes of Health. The government may have certain rights in this invention.

BACKGROUND OF THE INVENTION

The present invention relates generally to the field of auditory measurement. More particularly, the present invention pertains to auditory measurement systems and methods, such as those that may be useful in performing assessments of a patient's auditory function including the fitting of a hearing aid, the screening of a patient's hearing, the diagnosis of middle-ear dysfunction, etc.

The peripheral auditory system includes the external ear, middle-ear, cochlea, the auditory nerve and specific regions of the brain serving auditory perception. The external ear consists of the pinna, which projects from the side of the head and functions as a collector of sound energy, and the ear canal, which leads from the bottom region of the pinna and transmits sound to the eardrum (or tympanic membrane). Functional assessment of the peripheral auditory system is important to identifying and rehabilitating hearing pathologies. A device to screen and diagnose middle-ear dysfunction is valuable in the identification of a hearing disorder and in the clinical management of an existing hearing disorder.

A standard clinical test of middle-ear functioning is an acoustic immittance, test, which refers to one or both of an acoustic admittance or an acoustic impedance test performed in the ear canal of a patient (ANSI S3.39-1987. American National Standard Specifications for Instruments to Measure Aural Acoustic Impedance and Admittance (Aural Acoustic Immittance). An acoustic immittance test includes tympanometry, which is the measurement of acoustic immittance in the ear canal as a function of air pressure, herein termed static pressure, as the static pressure is varied within the ear canal (ANSI S3.39-1987). The acoustic impedance, when expressed as a complex number with two components, is the exact inverse of the acoustic admittance. Thus, knowledge of the acoustic admittance constitutes knowledge of acoustic impedance. In many respects herein, the terms acoustic immittance and acoustic admittance can be used interchangeably. It is understood that the term static pressure refers to the total pressure of air in the ear canal that is slowly varying with respect to the acoustic variations of the stimuli used in acoustic immittance testing. A common stimulus used in clinical tympanometry is a 226-Hz tone, which has a period of approximately 4.4 ins. As long as the total pressure of air is varying slowly with respect to such a 4.4 ms duration, it is common to refer to this total pressure as a static pressure of air. To those skilled in the art, a tympanometry test is a measurement of acoustic admittance or impedance.

In a clinical (immittance) tympanometry test, a probe is inserted into the ear canal in a substantially leak-free manner, and a static pressure pump adjusts the static pressure just above and below the ambient, atmospheric pressure. This creates a static pressure difference across the eardrum. While the pump pressure is varied, a low-frequency sinusoidal sound is presented, typically at a low frequency of 226 Hz. As the static pressure exerts forces on the eardrum, an acoustic response to the low-frequency tone (e.g., measured by a microphone in the probe) varies in the normal-functioning ear. A tympanogram, which is a result of the tympanometry test, is often represented by a plot of the calibrated microphone response to the tone as a function of static pressure This calibrated microphone response is called an acoustic admittance, which is an acoustic transfer function of the ear. The acoustic admittance is defined as the ratio of the acoustic volume per unit time swept out in response to an acoustic pressure signal. The aural acoustic admittance, which is the acoustic admittance measured in the ear canal at one specific location, typically at the tip of the probe, has the property that it is highly sensitive to its choice of measurement location in the ear canal. Clinical immittance tympanometry is usually performed at a frequency of 226 Hz (e.g., see ANSI S3.39-1987), for which a simple compensation mechanism can be used, at least in the ears of older children and adults, to transform the aural immittance response from the probe tip to the eardrum. The eardrum is the port into which acoustically transmitted signals are input from the ear canal into the middle ear, and thus the eardrum location is preferred for a test of air-conducted middle-ear functioning. At frequencies an octave or so higher than 226 Hz, the compensation procedure recommended in ANSI S3.39-1987 becomes increasingly inaccurate. While various forms of multifrequency tympanometry exist, in which acoustic immittance is measured at frequencies of 660 Hz and higher frequencies up to approximately 2000 Hz, a practical difficulty in multifrequency tympanometry is the interpretation of the response at the probe tip in terms of the response at the eardrum, which is the preferred site at which to assess middle-ear functioning. One approach is to calculate a middle-ear resonance frequency from a multifrequency tympanogram, which can indicate some forms of middle-ear dysfunction, and another approach is to classify immittance tympanograms in terms of their shape. The latter classification scheme has interpretative problems at higher frequencies in the range important for speech perception and in responses measured in infants and young children.

A standard aural acoustic immittance test may include immittance tympanometry and an acoustic immittance test of the middle-ear muscle reflex (MEMR). This MEMR is a change in the tonus of a middle-ear (stapedius) muscle in response to a stimulus, often called the activator signal, which is the elicitor of the MEMR. The muscle contractions associated with activation of the MEMR are tested based on a change in the acoustic immittance, and such acoustic reflex testing is part of the acoustic immittance test battery (ANSI S3.39-1987). Thus, to one skilled in the art of audiology, a tympanometry test is an acoustic immittance test at varying pressure and an acoustic reflex test is based on a change in the acoustic immittance produced by presentation of a MEMR activator signal (pure tones and broadband noise are commonly used activators).

Because acoustic immittance testing is commonly used only at low frequencies, the associated acoustic-reflex test in the acoustic immittance test battery is also performed at low frequencies, commonly using the acoustic admittance change at 226 Hz. Such an acoustic reflex test using acoustic admittance change has the disadvantage that the change in response at 226 Hz is typically smaller than the change at a higher probe frequency. As such, acoustic-reflex thresholds measured at this frequency may be higher than acoustic-reflex thresholds measured at higher frequencies.

More generally, an acoustic transfer function of the ear is any ratio of acoustical variables, with each acoustical variable measured in the ear canal. Two examples of acoustic transfer functions have been described, the acoustic admittance and acoustic impedance. Another important acoustic transfer function of the ear is acoustic reflectance, which is the ratio of the reflected to the incident pressure signal that propagates in the ear canal between the probe and eardrum. Each reflected and incident signal is measured at the same location in the ear canal so that the pressure reflectance is an acoustic transfer function at a particular location in the ear canal.

Like acoustic immittance, the acoustic reflectance can be expressed at each frequency by a complex number, which has real and imaginary components, or, alternatively, magnitude and phase components. Unlike any of the components of acoustic immittance, the acoustic reflectance has the property that its magnitude is approximately independent of the measurement location in the ear canal (Stinson M R, Shaw E A G, and Lawton B W (1982), "Estimation of acoustical energy reflectance at the eardrum from measurements of pressure distribution in the human ear canal", *J. Acoust. Soc. Am.* 72, 766-773), as long as the ear-canal walls are sufficiently rigid, as is the case for older children and adults but not necessarily for infants (Keefe D H, Bulen J C, Arehart K H, and Burns E M (1993), "Ear-canal impedance and reflection coefficient in human infants and adults", *J. Acoust. Soc. Am.* 94, 2617-2638).

The energy reflectance, which is also termed power reflectance, is the squared magnitude of the pressure reflectance, and is thus also insensitive to ear-canal measurement location. This means that a measurement of energy reflectance at the probe tip is approximately equal to the energy reflectance at the eardrum, and is thus a direct measurement of the acoustic functioning of the middle ear at the ear drum. As such, the energy reflectance of the middle ear can be interpreted at high frequencies, without the need for a compensation procedure to transform the response between the probe tip and eardrum.

The energy reflectance varies between zero and one in the absence of internal sources of energy within the cochlea, such that an energy reflectance of zero means that no energy is reflected from the eardrum and an energy reflectance of one means that all the energy is reflected from the eardrum. It follows that energy reflectance is advantageous for assessing middle-ear functioning over the wideband range of speech frequencies up to 4000 or 8000 Hz, or even higher depending on the measurement device, whereas acoustic immittance at the probe tip is limited to lower frequencies.

A wideband acoustic admittance can also be calculated up to 4000 or 8000 Hz, or even higher frequencies, using the similar measurement principles underlying wideband acoustic reflectance (Keefe D H, Ling R, and Bulen J C (1992), "Method to measure acoustic impedance and reflection coefficient", *J. Acoust. Soc. Am.* 91, 470-485). By measuring the distance between the probe tip and eardrum and using an interpretative model of acoustic transmission in the ear canal, the wideband acoustic admittance response at the probe tip can be transformed to a wideband acoustic admittance response at the eardrum. Such a wideband analysis is distinct from any compensation procedure for acoustic immittance known to those skilled in the art of acoustic immittance, and thus the term wideband acoustic admittance is fundamentally different from aural acoustic admittance used in aural immittance test devices.

Based on a measurement of wideband acoustic reflectance, the complex components of wideband acoustic admittance can thus be calculated, for which the real component is called the acoustic conductance. The product of acoustic conductance and the squared root-mean squared magnitude of the acoustic pressure is the power absorbed by the ear (Keefe et al., 1993). Because the power dissipated in the ear canal and at its walls is small over a wide frequency range, conservation of energy implies that the power absorbed by the ear at the probe tip is equal to the power absorbed by the ear at the eardrum. Thus, this absorbed power, like energy reflectance, is a second quantity that is insensitive to the measurement location. The acoustic intensity is the rate at which acoustic energy flows per unit through a cross-sectional area. Because the acoustic energy flow in the ear canal is predominantly of the plane-wave form, it follows that the acoustic intensity is equal to the ratio of the absorbed power and the cross-section ear-canal area at the location at which the absorbed power is measured.

With the approximation that no power is dissipated in the ear canal and at its walls, conservation of energy also requires that the incident energy to the ear canal at any location is equal to the sum of the reflected and transmitted energies. It follows that the energy transmittance, which is defined as the ratio of the transmitted energy traveling in the ear canal towards the eardrum to the incident range, is equal to one minus the energy reflectance (Keefe, D. H. and Simmons, J. L. (2003), "Energy transmittance predicts conductive hearing loss in older children and adults," *J. Acoust. Soc. Am.* 114, 3217-3238). Because the energy reflectance is approximately equal at the probe tip (or other measurement location) and eardrum, the energy transmittance is also equal at the probe tip and eardrum. This energy transmittance can also be termed the energy absorptance, because the eardrum absorbs all the transmitted energy (aside from small correction terms due to otoacoustic-emission signals evoked or spontaneously present in the cochlea). This energy transmittance is also called power absorption.

Various patents describe systems and methods for measuring an acoustic reflectance of the ear (e.g., as a function of static pressure and stimulus parameters including time, frequency or stimulus level). For example, U.S. Pat. No. 5,594,174 to Keefe issued 14 Jan. 1997, entitled "System and Method for Measuring Acoustic Reflectance;" U.S. Pat. No. 5,651,371 to Keefe issued 29 Jul. 1997, entitled "System and Method for Measuring Acoustic Reflectance;" and U.S. Pat. No. 5,792,072 to Keefe issued 11 Aug. 1998, entitled "System and Method for Measuring Acoustic Reflectance," all describe various acoustic reflectance measurement systems and methods.

An important step in any device to perform an acoustic reflectance test is a preliminary calibration, which allows the device to measure the acoustic reflectance data in a test ear in terms of the measured microphone pressure at the probe tip and calibration parameters, which are output from the calibration. The calibration of the acoustic reflectance device is typically performed at one stimulus level, and the acoustic reflectance test in the ear is also performed at one stimulus level. The calibration and ear-testing stimulus levels are the same, at least in one preferred embodiment.

In an alternate embodiment, the stimulus levels differ. The difference in stimulus levels is applied as an additional variable to the calibration parameters by the calibration step. For example, it may be convenient to perform the reflectance test in an infant's ear at a higher stimulus level, because the internal physiologic noise level (produced by the cardiovascular and respiratory systems) is higher in infants than in adults. Three possible choices of calibration parameters are the source incident pressure and source reflectance, the Norton source volume velocity and Norton source admittance, and the Thevenin source pressure and Thevenin source impedance. Other choices of calibration parameters may be equivalent to any of these three sets of calibration parameters, which are each equivalent to one another. A higher stimulus level in testing the infant's ear is achieved by increasing the source incident pressure, the Norton source volume velocity or the Thevenin source pressure, respectively.

It should be understood that, in view of the relationships described above for single-frequency and wideband acoustic transfer functions, a device to measure acoustic reflectance is capable of measuring a wideband response of any or all of acoustic reflectance, energy reflectance, energy transmittance, acoustic admittance, acoustic impedance, absorbed power, and acoustic intensity. Thus, an acoustic reflectance test implies the ability to output the acoustic reflectance and any or all of these other acoustic transfer functions and related responses.

The use of the term "tympanometry" in this application has a different and more general meaning than the use of the term by one skilled in the art of audiological measurements, to whom tympanometry means a pressurized acoustic immittance measurement. Tympanometry in this application refers to the measurement of an acoustic transfer function or sound pressure as a function of frequency or time, and as a function of static pressure, which is varied within the ear canal at a rate much more slowly than the longest period of the acoustic stimulus, which is the period of the lowest frequency for which significant energy is present in the stimulus spectrum. Preferably, the lower limit of the frequency range of tympanometry measurements is approximately 200 Hz, so that this longest period does not exceed 5 ms. The restriction of tympanometry measurements to frequencies at and above 200 Hz is reasonable because middle-ear functioning is slowly varying at low frequencies and because the internal noise at the output of the microphone, which has contributions from measurement system noise, environmental noise, and physiologic noise sources within the patient, becomes large at frequencies below 200 Hz. A reflectance tympanometry test was first described by Keefe DH and Levi E (1996) ("Maturation of the middle and external ears: Acoustic power-based responses and reflectance tympanometry," *Ear and Hearing*, 17:361-373), which energy reflectance was measured as a function of frequency and static pressure in the ear canal. In view of the description herein, it should be appreciated that the principles of how an immittance tympanometry device operates in calibration and ear-testing modes differ substantially from the principles of how a reflectance tympanometry device operates.

The above-referenced patents, for example, describe procedures for varying static pressure in the ear canal so as to perform reflectance tympanometry. For example, FIG. 9 of U.S. Pat. No. 5,792,072 shows a system to measure reflectance as a function of static pressure and frequency comprised of a computer, an ear canal estimate storage area, and a tympanometer. The tympanometer is comprised of a probe assembly, a static pressure pump, and a tympanometer processor. However, unlike conventional admittance tympanometers which are known to use various feedback systems to control static pressure, the system measures acoustic reflectance without knowing what the static pressure is in the ear canal.

Published reports of measurements of acoustic reflectance of the ear as a function of static pressure and frequency share the same limitation, e.g., they lack the ability to control or measure static pressure in any fashion; see, for example, Keefe DH and Levi E (1996) ("Maturation of the middle and external ears: Acoustic power-based responses and reflectance tympanometry," *Ear and Hearing,* 17:361-373). Further, for example, in Margolis, et al., "Wideband reflectance tympanometry in normal adults," *J. Acoust. Soc. Am.* 106: 265-280 (1999) and in Margolis, et al., "Wideband reflectance tympanometry in chinchillas and humans," *J. Acoust. Soc. Am.* 110:1453-1464 (2001), researchers measured reflectance by varying static pressure manually. Yet further, acoustic reflectance tympanometry was also performed as described in Keefe and Simmons (2003) ("Energy transmittance predicts conductive hearing loss in older children and adults," *J. Acoust. Soc. Am.* 114, 3217-3238) using a device similar to that described in U.S. Pat. No. 5,792,072 (e.g., a computer commands a static pressure pump to an intended static pressure by supplying a DC voltage to a pump controller).

However, if the intended static pressure is not equal to the actual static pressure in the ear canal when reflectance tympanometry is carried out, then measurement errors occur in such tests. Due to the different manner in which the probe fits in the ear canal in different patients, it may never be possible to know the extent of the errors (e.g., the actual static pressure in the ear canal may be very different than actually intended or even unknown). In fact, whenever there is a leaky fit of the probe assembly into the ear canal, the resulting static pressure in the ear canal may remain at atmospheric pressure independent of the intended static pressure in the device and the resulting measurements may be unusable. Such a lack in accuracy of acoustic reflectance measurements, affects the reliability of the use of such acoustic reflectance systems in clinical applications (e.g., in the screening and diagnosis of middle-ear dysfunction and conductive hearing loss in human patients).

A conductive hearing loss is a hearing loss associated with sound conduction through the middle-ear; some types of middle-ear dysfunction are pathologies that include a conductive hearing loss but other types of middle-ear dysfunction do not include a conductive hearing loss. A child with a conductive hearing loss tends to have associated developmental delays in language acquisition and cognitive skills, so that an improved method to screen and diagnose a conductive hearing loss would be important in efforts to ameliorate the hearing loss, minimize developmental delays, and minimize the resulting personal, family and societal costs associated with an extended period of an unrecognized conductive hearing loss. Conventional admittance tympanometry is inefficient at detecting a conductive hearing loss, whereas acoustic reflectance is capable of detecting the presence of a conductive hearing loss.

The above discussion noted that acoustic-reflex testing in the form of a shift in acoustic immittance has been a well known part of an acoustic immittance test battery for decades. Other types of acoustic-reflex testing, which do not rely on acoustic immittance tests as practiced within the scope of ANSI S3.39-1987 and related audiological publications, have recently been developed. These non-immittance types of MEMR tests fall into two classes based on a shift in a response in the presence of a MEMR activator signal: (1) a MEMR test based on a shift in sound pressure, which may be any shift in the magnitude and/or phase response in the frequency domain or in the waveform of a time-domain response, and (2) a MEMR test based on a shift in a wideband acoustic reflectance response (or in related acoustic absorbed power, transmittance or acoustic intensity responses).

Yet further, in many circumstances, existing individual tests of the functional status of the auditory system (e.g., such as a test of acoustic reflectance to assess the peripheral auditory system) provides incomplete and limited information. For example, the use of an admittance tympanogram to assess the status of the external and middle-ear may not provide desired information about middle-ear functioning in newborns because of the mobility of the ear-canal walls, about the likelihood of a conductive hearing loss, or about the presence of middle-ear dysfunction that affects middle-ear functioning at a frequency higher than that used in the admittance tympanogram. Further, for example, although a conventional middle-ear muscle reflex (MEMR) test may provide an indirect measure of cochlear and auditory nerve functioning, such a test provides a high false-positive rate (e.g., some normal-hearing ears lack a MEMR shift), in part, due to limitation of current testing procedures.

Various apparatus have been described which may be used to perform a battery of tests on a patient. For example, U.S. Pat. No. 6,974,421 to Causevic et al. issued 13 Dec. 2005, entitled "Handheld audiometric device and method of testing hearing," describes an apparatus that may perform a battery of tests, either independently or combined on a patient. Such tests are described as including an otoacoustic measurements utilizing digital signal processing for evoked otoacoustic signal processing, an auditory brain stem response (ABR) test, admittance tympanometry, and otoreflectance. Further, for example, U.S. Pat. No. 5,601,091 to Dolphin issued 11 Feb. 1997, entitled "Audiometric apparatus and association screening method;" as well as U.S. Pat. No. 5,916,174 to Dolphin issued 29 Jun. 1999, entitled "Audiometric apparatus and associated screening method," describe apparatus that may perform multiple tests including an otoacoustic emission (OAE) test, an ABR test, and even an acoustic reflectivity test. Yet further, for example, International Publication No. WO 03/099121 A2, entitled "Systems and methods for conducting multiple diagnostic hearing tests" describes a system that is capable of performing audiometry tests, an otoacoustic emission test, and acoustic immittance tests including admittance tympanometry and reflex testing based on a shift in acoustic immittance.

However, although apparatus previously described may perform a battery of specifically described tests, such combinations of tests still do not provide sufficient information indicative of various auditory functions and/or the impairment of such auditory function. For example, the performance of such tests may not provide sufficient information for the screening of newborn infants at high frequencies, for use in the diagnosis of auditory neuropathy, or for use in the fitting of a hearing aid. As such, improvement in the types of apparatus that combine a battery of tests is needed.

SUMMARY OF THE INVENTION

One embodiment of the present invention is useful in measuring an acoustic reflectance of the ear in response to a sound stimulus as a function of static pressure and sound stimulus parameters such as frequency, time or stimulus level, in which there is a feedback procedure to maintain the actual static pressure in the ear canal at an intended level. Such a feedback procedure to maintain the static pressure at an intended value and alert the operator when a probe assembly used to make the measurements has a leaky insertion into the ear canal would increase the reliability and accuracy of acoustic reflectance measurements. Thus, for example, such feedback would improve the use of acoustic reflectance measurement systems in clinical applications for the screening and diagnosis of middle-ear dysfunction. In one embodiment, the present invention discloses such a feedback system and method which has benefits for practical applications of acoustic reflectance to screen and diagnose middle-ear dysfunction and conductive hearing loss in human patients.

One embodiment of a system for use in performing reflectance tympanometry using feedback includes a probe configured to be coupled into an ear canal in a substantially leak-free state. The probe includes at least one acoustic transmitter to present one or more acoustic stimulus signals into the ear canal and at least one acoustic transducer to measure an acoustic response to the one or more acoustic stimulus signals. A pump is operatively coupled to the probe to vary the static pressure in the ear canal and a processing apparatus is operable to initiate one or more auditory tests on a patient upon receipt of input from a user. The processing apparatus is operable for use in initiating and controlling performance of a reflectance tympanometry test on the patient using the probe resulting in reflectance tympanometry data (e.g., at least one or more transfer functions based at least on a response to an acoustic stimulus signal and a calibrated acoustic transfer function). The system further includes a static pressure transducer to detect static pressure in the ear canal and a controller for use in comparing detected actual static pressure in the ear canal to a desired static pressure. The pump is controlled to maintain the desired static pressure in the ear canal based on the comparison.

In one embodiment of the system, the controller is operable to determine that the pump is unable to maintain the desired static pressure and the system further includes an output device operable to provide an alert indication to the user that the pump is unable to maintain the desired pressure.

One embodiment of a method for use in assessing auditory function in which such a feedback system is used includes providing a test system for use in performing reflectance tympanometry. The test system includes a processing apparatus configured to initiate a reflectance tympanometry test upon receipt of input from a user. A probe is electrically coupled to the processing apparatus and is acoustically coupled (e.g., insertible) into an ear canal in a substantially leak-free state. For any ear-canal test described herein, the probe is alternatively said to be coupled into an ear canal if the meaning is clear that it is acoustically coupled. The probe includes at least one acoustic transmitter to present one or more acoustic stimulus signals into the ear canal, and further includes at least one acoustic transducer to measure an acoustic response to the one or more acoustic stimulus signals. A pump is operatively coupled to the probe to vary the static pressure in the ear canal and a static pressure transducer is provided to detect static pressure in the ear canal.

The method further includes performing a reflectance tympanometry test on a patient using the testing system. The reflectance tympanometry test includes providing a calibrated acoustic transfer function using the probe, inserting the probe into the ear canal of the patient in a substantially leak-free state, and delivering an acoustic stimulus signal into the ear canal using the at least one acoustic transmitter of the probe. The static pressure in the ear canal is controlled using the pump. Such control is provided by detecting actual static pressure in the ear canal using the static pressure transducer, comparing the detected static pressure to a desired static pressure, and controlling the pump to maintain the desired static pressure in the ear canal based on the comparison of the desired static pressure to the actual static pressure. Further, the reflectance tympanometry test includes detecting a response to the acoustic stimulus signal using the at least one acoustic transducer of the probe and providing reflectance tympanometry data based at least on the response to the acoustic stimulus signal and the calibrated acoustic transfer function.

In one embodiment of the method, the method further includes determining that the pump is unable to maintain the desired static pressure and providing an alert indication to the user that the pump is unable to maintain the desired pressure (e.g., the user may then reinsert the probe or take some other action).

Further, in one or more other embodiments of the method and system using feedback, the test system may be operable to perform one or more other auditory tests in addition to reflectance tympanometry, such as an admittance tympanometry test, an Eustachian tube test, a middle-ear muscle reflex decay test, a middle-ear muscle reflex threshold test, an otoacoustic emission test of medial olivocochlear status, an otoacoustic emission test, an acoustic test of eardrum response based on probe response, an acoustic test of volume of air between the probe and eardrum, an acoustic test of ear canal cross-sectional area, an acoustic test of ear canal length, an auditory brain stem response test, and/or an audiometry test.

Yet in a further embodiment of the method and system, analysis of the reflectance tympanometry data and results of the one or more other auditory tests performed on a patient using the test system may be performed and an output to the user representative of a probability of an auditory impairment in function of the patient's auditory system may be provided.

One or more embodiments of the present invention also relate to the use of a combination of tests to assess the functional status of the auditory system (e.g., the peripheral auditory system). For example, such combination of tests may provide results of the status of the external and middle-ears with the status of either the cochlea, the auditory nerve, the specific brain regions serving auditory perception, or some combination thereof.

The ability to combine individual test results in a single test battery, as described in one or more embodiments herein, has the clinical potential of providing a more nearly complete assessment of the peripheral auditory system. For example, such a test battery of the peripheral auditory system may be used to more accurately identify hearing loss in infants, may be used during follow-up clinical management of a patient, and/or may be used to accurately classify normal-hearing infants as having no permanent hearing loss.

Further, at least in one embodiment, the present invention provides a combination of tests that includes the measurement of acoustic reflectance to assess the functioning of the auditory system (e.g., assessments for use in screening and diagnosing hearing pathology, fitting of hearing aids, etc.) An acoustic reflectance measurement is a precise, objective measurement that assesses how much sound is reflected from the eardrum and with what time delay in response to an incident sound stimulus presented into the ear canal. In other words, an acoustic reflectance test quantifies the reflected sound that "echoes" from the middle-ear of a patient in response to a sound stimulus.

In one embodiment of a test system for use in assessing auditory function, the system includes a probe configured to be coupled into an ear canal in a substantially leak-free state (i.e., wherein the probe comprises at least one acoustic transmitter to present one or more acoustic stimulus signals into the ear canal, and further wherein the probe comprises at least one acoustic transducer to measure an acoustic response to the one or more acoustic stimulus signals), a pump operatively coupled to the probe to vary the static pressure in the ear canal, and a processing apparatus operable to initiate one or more auditory tests on a patient upon receipt of input from a user. The processing apparatus is operable for use in initiating and controlling performance of a reflectance tympanometry test (e.g., with or without feedback control of static pressure) on the patient using the probe resulting in reflectance tympanometry data comprising at least one or more transfer functions based at least on a response to an acoustic stimulus signal and a calibrated acoustic transfer function. The system further includes an output device to provide an output to a user based on the reflectance tympanometry data and results of one or more other auditory tests (i.e., the one or more other auditory tests comprise at least one of an admittance tympanometry test, an Eustachian tube test, a middle-ear muscle reflex decay test, a middle-ear muscle reflex threshold test, an otoacoustic emission test of medial olivocochlear status, an otoacoustic emission test, an acoustic test of eardrum response based on probe response, an acoustic test of volume of air between the probe and eardrum, an acoustic test of ear canal cross-sectional area at two or more locations along an axis of the ear canal, an acoustic test of ear canal length, an auditory brain stem response test, and an audiometry test). Further, the output is representative of a probability of one or more auditory impairments in function of the patient's auditory system generated using both the reflectance tympanometry data and results of the one or more other auditory tests.

In another embodiment of a test system for use in assessing auditory function, the system includes a probe configured to be coupled into an ear canal (i.e., wherein the probe comprises at least one acoustic transmitter to present one or more acoustic stimulus signals into the ear canal, and further wherein the probe comprises at least one acoustic transducer to measure an acoustic response to the one or more acoustic stimulus signals), and processing apparatus operable to initiate one or more auditory tests on a patient upon receipt of input from a user. The processing apparatus is operable for use in initiating and controlling performance of an ambient pressure acoustic reflectance test on the patient resulting in acoustic reflectance data comprising at least one or more transfer functions based at least on a response to an acoustic stimulus signal and a calibrated acoustic transfer function. The ambient pressure acoustic reflectance test is controlled by the processing apparatus so as to deliver an acoustic stimulus signal into the ear canal using the at least one acoustic transmitter of the probe. The acoustic stimulus signal is limited to a single amplitude level acoustic stimulus signal. Further, the system includes an output device to provide an output to, a user based on the acoustic reflectance data and results of one or more other auditory tests (i.e., the one or more other auditory tests comprise at least one of an admittance tympanometry test using a pump to vary static pressure in the ear canal, an Eustachian tube test, a middle-ear muscle reflex decay test, a middle-ear muscle reflex threshold test, an otoacoustic emission test, an otoacoustic emission test of medial olivocochlear status, an acoustic test of eardrum response based on probe response, an acoustic test of volume of air between the probe and eardrum, an acoustic test of ear canal cross-sectional area at two or more locations along an axis of the ear canal, an acoustic test of ear canal length, an auditory brain stem response test, and an audiometry test). Further, the output is representative of a probability of one or more auditory impairments in function of the patient's auditory system generated using both the acoustic reflectance data and results of the one or more other auditory tests.

In one or more embodiments of the systems using reflectance data (e.g., acoustic reflectance data or reflectance tympanometry data), the output device may provide an output to the user representative of a probability that the patient has hearing loss associated with sound conduction through the middle-ear and/or the output device may provide an output to the user indicating whether a normal hearing infant has a permanent hearing loss.

Further, in one or more embodiments of the systems using reflectance data, the processing apparatus used to perform the reflectance tympanometry test is also operable to initiate and control performance of one or more of the other auditory tests on the patient.

Further, in one or more embodiments of the systems using reflectance data, one or more of the other auditory tests may be performed using at least one additional test apparatus, wherein the at least one additional test apparatus is operable for use in providing results of the one or more other auditory tests for use in generating the output.

Further, in one or more embodiments of the systems using reflectance data, the one or more other auditory tests includes at least a middle-ear muscle reflex threshold test. Further, the one or more other auditory tests may include a middle-ear muscle reflex decay test based at least in part on results of the middle-ear muscle reflex threshold test.

Further, in one or more embodiments of the systems using reflectance data, the one or more other auditory tests include at least one of an acoustic test of volume of air between the probe and the eardrum of the patient, an acoustic test of ear canal cross-sectional area at two or more locations along an axis of the ear canal of the patient, and an acoustic test of ear canal length of the patient between a tip of the probe and the eardrum. A single frequency admittance tympanometry test may be used in determining the volume of air between the probe and the eardrum of the patient; the slope of a phase of an acoustic reflectance test calculated over a frequency range may be used to determine ear canal length between the tip of the probe and the eardrum; and/or an acoustical measurement of a cross-sectional area at a tip of the probe and a cross-sectional area at one or more locations between the probe tip and the eardrum of the patient or an acoustical measurement of a cross-sectional area at two or more locations between the probe tip and the eardrum of the patient may be used.

Further, in one or more embodiments of the systems using reflectance data, the one or more other auditory tests include at least an otoacoustic emission test.

Further, in one or more embodiments of the system using reflectance data, the one or more other auditory tests include at least an otoacoustic emission test of medial olivocochlear status.

Further, in one or more embodiments of the systems using reflectance data, the one or more other auditory tests include at least an auditory brain stem response test.

Further, in one or more embodiments of the systems using reflectance data, the one or more other auditory tests include at least a middle-ear muscle reflex threshold test. In addition, such embodiments may also include an otoacoustic emission test. Yet further in such embodiments, the processing apparatus is further operable to analyze the reflectance data and the results of the one or more other auditory tests and the output device provides an output to the user representative of a probability of at least one of middle-ear dysfunction, cochlear dysfunction, sensorineural dysfunction, and auditory neuropathy.

Further, in one or more embodiments of the systems using reflectance data, the one or more other auditory tests include at least a middle-ear muscle reflex threshold test and an otoacoustic emission test of medial olivocochlear status. In such embodiments, the processing apparatus may be further operable to analyze the reflectance data and the results of the one or more other auditory tests and the output device may provide an output to the user representative of a probability of auditory neuropathy.

Further, in one or more embodiments of the systems using reflectance data, the one or more other auditory tests include at least a middle-ear muscle reflex threshold test and an otoacoustic emission test. In such embodiments, the processing apparatus may be further operable to analyze the reflectance data and the results of the one or more other auditory tests, and the output device may provide an output to the user representative of a probability of at least one of middle-ear dysfunction, cochlear dysfunction, auditory neuropathy.

Still further, in one or more embodiments of the systems using reflectance data, the one or more other auditory tests include at least one audiometry test resulting in audiometry data. In such embodiments, the processing apparatus may be further operable to analyze the reflectance tympanometry data and the audiometry data, and the output device may provide at least one output indicating a behavioral threshold of hearing for the patient or representative of a probability of an auditory impairment in function of the patient's auditory system.

Another system for use in assessing auditory function is provided that includes a probe configured to be coupled into an ear canal (e.g., wherein the probe comprises at least one acoustic transmitter to present one or more acoustic stimulus signals into the ear canal, and further wherein the probe comprises at least one acoustic transducer to measure an acoustic response to the one or more acoustic stimulus signals) and processing apparatus operable to initiate one or more auditory tests on a patient upon receipt of input from a user. The processing apparatus is operable for use in initiating and controlling performance of a non-immittance type middle-ear muscle reflex threshold test on the patient using the using the probe. Further, the system includes an output device to provide an output to the user based on results of the non-immittance type middle-ear muscle reflex threshold test and results of one or more other auditory tests (i.e., the one or more other auditory tests comprise at least one of an otoacoustic emission test, an acoustic reflectance test comprising at least one of an ambient pressure acoustic reflectance test and a reflectance tympanometry test using a pump to vary static pressure, an auditory brain stem response test, and an otoacoustic emission test of medial olivocochlear status).

Further, in one or more embodiments of the systems relating to use of non-immittance middle-ear muscle reflex threshold tests, the processing apparatus may be further operable to analyze results of the non-immittance type middle-ear muscle reflex threshold test and results of the one or more other auditory tests performed on the patient, and further the output device may provide an output to the user representative of a probability of an auditory impairment in function of the patient's auditory system (e.g., a probability of a probability of auditory neuropathy).

Still another system for use in assessing auditory function includes a probe that can be coupled into an ear canal (e.g., wherein the probe comprises at least one acoustic transmitter to present one or more acoustic stimulus signals into the ear canal, and further wherein the probe comprises at least one acoustic transducer to measure an acoustic response to the one or more acoustic stimulus signals) and processing apparatus operable to initiate one or more auditory tests on a patient upon receipt of input from a user. The processing apparatus is operable for use in initiating and controlling performance of a middle-ear muscle reflex threshold test on the patient using the using the probe. Further, the system includes an output device to provide an output to the user based on results of the middle-ear muscle reflex threshold test and results of one or more other auditory tests (i.e., the one or more other auditory tests comprise at least one of an otoacoustic emission test, an acoustic reflectance test comprising at least one of an ambient pressure acoustic reflectance test and a reflectance tympanometry test using a pump to vary static pressure, an auditory brain stem response test, and an otoacoustic emission test of medial olivocochlear status). The output is representative of a probability of one or more auditory impairments in function of the patient's auditory system generated using both the results of the middle-ear muscle reflex threshold test and the results of the one or more other auditory tests.

Further, in one or more embodiments of the systems relating to use of non-immittance middle-ear muscle reflex threshold tests as well as any other middle-ear muscle reflex threshold tests, the processing apparatus is further operable to initiate and control performance of one or more of the other auditory tests on the patient.

Further, in one or more embodiments of the systems relating to use of non-immittance middle-ear muscle reflex threshold tests as well as any other middle-ear muscle reflex threshold tests, one or more of the other auditory tests are performed using at least one additional test apparatus. The at least one additional test apparatus is operable for use in providing results of the one or more other auditory tests for use in generating the output.

Further, in one or more embodiments of the systems relating to use of non-immittance middle-ear muscle reflex threshold tests as well as any other middle-ear muscle reflex threshold tests, the processing apparatus is operable for use in initiating and controlling performance of a middle-ear muscle reflex decay test.

Further, in one or more embodiments of the systems relating to use of non-immittance middle-ear muscle reflex threshold tests as well as any other middle-ear muscle reflex threshold tests, the processing apparatus is further operable for initiating and controlling a middle-ear muscle reflex threshold test based on a wideband shift of a response in a reflectance tympanometry test in the presence of an ipsilateral or contralateral sound.

Further, in one or more embodiments of the systems relating to use of non-immittance middle-ear muscle reflex threshold tests as well as any other middle-ear muscle reflex threshold tests, the one or more other auditory tests comprise at least one of an ambient pressure acoustic reflectance test and a reflectance tympanometry test using a pump to vary static pressure in the ear canal resulting in reflectance tympanometry data.

Further, in one or more embodiments of the systems relating to use of non-immittance middle-ear muscle reflex threshold tests as well as any other middle-ear muscle reflex threshold tests, the one or more other auditory tests comprise at least an ambient pressure acoustic reflectance test or a reflectance tympanometry test performed on a patient using a pump to vary the static pressure in the ear canal of the patient, an otoacoustic emission test; and an auditory brain stem response test. In such embodiments, the output device may provide an output to the user representative of a probability of at least one of middle-ear dysfunction, cochlear dysfunction, sensorineural dysfunction, and auditory neuropathy.

Further, in one or more embodiments of the systems relating to use of non-immittance middle-ear muscle reflex threshold tests as well as any other middle-ear muscle reflex threshold tests, the one or more other auditory tests comprise at least an otoacoustic emission test and an auditory brain stem response test. In such embodiments, the output device may provide an output to the user representative of a probability of at least one of middle-ear dysfunction, cochlear dysfunction, sensorineural dysfunction, and auditory neuropathy.

Further, in one or more embodiments of the systems relating to use of non-immittance middle-ear muscle reflex threshold tests as well as any other middle-ear muscle reflex threshold tests, the one or more other auditory tests comprise at least an otoacoustic emission test. In such embodiments, the output device may provide an output to the user representative of a probability of at least one of middle-ear dysfunction, cochlear dysfunction, sensorineural dysfunction, and auditory neuropathy.

Further, in one or more embodiments of the systems relating to use of non-immittance middle-ear muscle reflex threshold tests as well as any other middle-ear muscle reflex threshold tests, the one or more other auditory tests comprise at least an auditory brain stem response test performed on the patient. In such embodiments, the output device provides an output to the user representative of at least one of middle-ear dysfunction, cochlear dysfunction, sensorineural dysfunction, and auditory neuropathy.

Further, in one or more embodiments of the systems relating to use of non-immittance middle-ear muscle reflex threshold tests as well as any other middle-ear muscle reflex threshold tests, the processing apparatus is operable to control the middle-ear muscle reflex threshold test by controlling the delivery of two or more acoustic stimulus signals into the ear canal such that onset of at least a first acoustic stimulus signal of the two or more acoustic stimulus signals is earlier than an onset of at least a second acoustic stimulus signal of the two or more acoustic stimulus signals by a time that is the same as or longer than the middle-ear reflex latency, wherein the first stimulus signal is delivered in the same or opposite ear to activate a middle-ear muscle reflex effect that acts on an acoustic response to the later of the two or more stimulus signals, and further wherein the processing apparatus is operable to compare acoustic responses to each of the two or more acoustic stimulus signals to detect whether a middle-ear muscle reflex is present or absent.

Further, in one or more embodiments of the systems relating to use of non-immittance middle-ear muscle reflex threshold tests as well as any other middle-ear muscle reflex threshold tests, the processing apparatus is operable to control the middle-ear muscle reflex threshold test by controlling delivery of a first acoustic stimulus signal into the ear canal at a first onset time, delivery of a third acoustic stimulus signal that is identical to the first acoustic stimulus signal into the same ear at a third onset time, and delivery of a second acoustic stimulus signal after the first onset time and before the third onset time to activate a middle-ear muscle reflex effect that acts on an acoustic response to the third acoustic stimulus signal, and further wherein the processing apparatus is operable to compare acoustic responses to each of the first and third acoustic stimulus signals to detect whether a middle-ear muscle reflex is present or absent.

Further, in one or more embodiments of the systems relating to use of non-immittance middle-ear muscle reflex threshold tests as well as any other middle-ear muscle reflex threshold tests, the processing apparatus is operable to control the middle-ear muscle reflex threshold test by controlling delivery of a first acoustic stimulus signal into the ear canal at a first onset time, delivery of a second acoustic stimulus signal into the ear canal at a second onset time after the first onset time to activate a middle-ear muscle reflex effect, and delivery of the first acoustic stimulus signal and the second acoustic stimulus signal together jointly into the ear canal at a third onset time, and further wherein the processing apparatus is operable to compare a sum of responses to the first and second acoustic stimulus signals to a response to the first acoustic stimulus signal and the second acoustic stimulus signal delivered together jointly into the ear canal to determine a nonlinear residual for use in detecting whether a middle-ear muscle reflex is present or absent.

Further, in one or more embodiments of the systems relating to use of non-immittance middle-ear muscle reflex threshold tests as well as any other middle-ear muscle reflex threshold tests, the processing apparatus is operable to control the middle-ear muscle reflex threshold test by controlling delivery of a first acoustic stimulus signal into the ear canal at a first onset time, delivery of a second acoustic stimulus signal into the ear canal at a second onset time, and delivery of the first acoustic stimulus signal and the second acoustic stimulus signal together jointly into the ear canal at a third onset time, wherein the processing apparatus is operable to control the gating of an activator signal on and off, and further wherein the processing apparatus is operable to determine a first nonlinear residual by comparing a sum of responses to the first and second acoustic stimulus signals to a response to the first acoustic stimulus signal and the second acoustic stimulus signal delivered together jointly into the ear canal when the activator signal is on, determine a second nonlinear residual by comparing a sum of responses to the first and second acoustic stimulus signals to a response to the first acoustic stimulus signal and the second acoustic stimulus signal delivered together jointly into the ear canal when the activator signal is off, and compare the first and second nonlinear residuals to detect whether a middle-ear muscle reflex is present or absent.

Further, in one or more embodiments of the systems relating to use of non-immittance middle-ear muscle reflex threshold tests as well as any other middle-ear muscle reflex threshold tests, the one or more other auditory tests comprise at least an acoustic reflectance test and an otoacoustic emission test of medial olivocochlear status. In such embodiments, the output device may provide an output to the user representative of a probability of an auditory impairment in function of the patient's auditory system (e.g., a probability of auditory neuropathy).

Further, in one or more embodiments of the systems relating to use of non-immittance middle-ear muscle reflex threshold tests as well as any other middle-ear muscle reflex threshold tests, the one or more other auditory tests comprise at least an audiometry test resulting in audiometry data, and further the output device may provide at least one of an output indicating a behavioral threshold of hearing for the patient and an output representative of a probability of an auditory impairment in function of the patient's auditory system.

Another system for use in assessing auditory function includes a probe configured to be coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals) and processing apparatus operable to initiate one or more auditory tests on a patient upon receipt of input from a user. The processing apparatus is operable for use in initiating and controlling performance of at least one of an acoustic test of volume of air between the probe and the eardrum of the patient, an acoustic test of ear canal cross-sectional area at two or more locations along an axis of the ear canal of the patient, and an acoustic test of ear canal length of the patient between a tip of the probe and the eardrum resulting in ear canal measurements. The processing apparatus is further operable for use in initiating and controlling performance of an acoustic reflectance test using the probe. The system further includes an output device to provide an output to the user based on the ear canal measurements and results of the acoustic reflectance test.

In one or more embodiments of the system, the processing apparatus may be operable for initiating and controlling performance of a single frequency admittance tympanometry test for use in determining the volume of air between the probe and the eardrum of the patient, the processing apparatus may be operable to use the slope of a phase of an acoustic reflectance test calculated over a frequency range to determine ear canal length between the tip of the probe and the eardrum, and/or the processing apparatus may be operable for initiating and controlling performance of an acoustical measurement of a cross-sectional area at a tip of the probe and a cross-sectional area at one or more locations between the probe tip and the eardrum of the patient or an acoustical measurement of a cross-sectional area at two or more locations between the probe tip and the eardrum of the patient.

In one further embodiment of the system, the processing apparatus is further operable analyze the ear canal measurements and determining a measure of cross-sectional area variability along the axis of the ear canal.

In further embodiments of the system, the processing apparatus is further operable to use the ear canal measurements to estimate sound pressure levels at the eardrum of the patient or one or more acoustic transfer functions at the eardrum of the patient.

Yet another system for use in assessing auditory function is described that includes a probe configured to be coupled into an ear canal (i.e., wherein the probe comprises at least one acoustic transmitter to present one or more acoustic stimulus signals into the ear canal, and further wherein the probe comprises at least one acoustic transducer to measure an acoustic response to the one or more acoustic stimulus signals) and a processing apparatus operable to initiate one or more auditory tests on a patient upon receipt of input from a user. The processing apparatus is operable for use in initiating and controlling performance of an acoustic reflectance test resulting in acoustic reflectance data and is operable for use in initiating and controlling performance of an audiometry test resulting in audiometry data. The system includes an output device for use in providing an output to a user based on the acoustic reflectance data and the audiometry data.

In one or more embodiments of the system, the processing apparatus is further operable for initiating and controlling performance of an air-conduction audiometry test or a bone-conduction audiometry test.

Further, in one or more embodiments of the system, the processing apparatus is further operable to analyze the auditory test data and the acoustic reflectance data, and the output device may provide an output to the user representative of at least one of a measurement of hearing and a risk assessment of middle-ear dysfunction.

A method for use in assessing auditory function includes providing a test system for use in performing one or more auditory tests on a patient. The test system includes a processing apparatus operable to initiate one or more tests upon receipt of input from a user, a probe electrically coupled to the processing apparatus and configured to be acoustically coupled into an ear canal in a substantially leak-free state (i.e., the probe comprises at least one acoustic transmitter to present one or more acoustic stimulus signals into the ear canal, and further wherein the probe comprises at least one acoustic transducer to measure an acoustic response to the one or more acoustic stimulus signals), and a pump operatively coupled to the probe to vary the static pressure in the ear canal. The method further includes performing a reflectance tympanometry test on the patient using the test system resulting in reflectance tympanometry data and performing one or more other auditory tests on the patient (i.e., the one or more other auditory tests comprise at least one of an admittance tympanometry test, an Eustachian tube test, a middle-ear muscle reflex decay test, a middle-ear muscle reflex threshold test, an otoacoustic emission test of medial olivocochlear status, an otoacoustic emission test, an acoustic test of eardrum response based on probe response, an acoustic test of volume of air between the probe and eardrum, an acoustic test of ear canal cross-sectional area at two or more locations along an axis of the ear canal, an acoustic test of ear canal length, an auditory brain stem response test, and an audiometry test). The reflectance tympanometry data and results of the one or more other auditory tests are analyzed and an output to the user is provided that is representative of a probability of one or more auditory impairments in function of the patient's auditory system based on both the reflectance tympanometry data and results of the one or more other auditory tests (e.g., a probability that the patient has hearing loss associated with sound conduction through the middle-ear, classification of a normal hearing infant as having no permanent hearing loss).

In another method for use in assessing auditory function, the method includes providing a test system for use in performing one or more auditory tests on a patient. The test system includes a processing apparatus operable to initiate one or more tests upon receipt of input from a user and a probe electrically coupled to the processing apparatus and configured to be acoustically coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals). The method further includes performing an ambient pressure acoustic reflectance test on the patient using the test system. Performing the ambient pressure acoustic reflectance test includes providing a calibrated acoustic transfer function using the probe, inserting the probe into the ear canal of the patient, delivering an acoustic stimulus signal into the ear canal using the at least one acoustic transmitter of the probe (i.e., the acoustic stimulus signal being limited to a single amplitude level acoustic stimulus signal), detecting a response to the acoustic stimulus signal using the at least one acoustic transducer of the probe, and providing acoustic reflectance data based at least on the response to the acoustic stimulus signal and the calibrated acoustic transfer function. The method further includes performing one or more other auditory tests on the patient (i.e., the one or more other auditory tests comprise at least one of an admittance tympanometry test using a pump to vary static pressure, an Eustachian tube test, a middle-ear muscle reflex decay test, a middle-ear muscle reflex threshold test, an otoacoustic emission test, an otoacoustic emission test of medial olivocochlear status, an acoustic test of eardrum response based on probe response, an acoustic test of volume of air between the probe and eardrum, an acoustic test of ear canal cross-sectional area at two or more locations along an axis of the ear canal, an acoustic test of ear canal length, an auditory brain stem response test, and an audiometry test) and analyzing the acoustic reflectance data and results of the one or more other auditory tests. An output is provided to the user representative of a probability of one or more auditory impairments in function of the patient's auditory system based on both the acoustic reflectance data and results of the one or more other auditory tests.

Another method for use in assessing auditory function includes providing a test system for use in performing one or more auditory tests on a patient. The test system includes a processing apparatus operable to initiate one or more tests upon receipt of input from a user and a probe electrically coupled to the processing apparatus and configured to be acoustically coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals). The method further includes performing a non-immittance type middle-ear muscle reflex threshold test on the patient using the test system and performing one or more other auditory tests on the patient (i.e., the one or more other auditory tests comprise at least one of an otoacoustic emission test, an acoustic reflectance test comprising at least one of an ambient pressure acoustic reflectance test and a reflectance tympanometry test using a pump to vary static pressure, an auditory brain stem response test, and an otoacoustic emission test of medial olivocochlear status).

Yet another method for use in assessing auditory function includes providing a test system for use in performing one or more auditory tests on a patient. The test system includes a processing apparatus operable to initiate one or more tests upon receipt of input from a user and a probe electrically coupled to the processing apparatus and configured to be acoustically coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals). The method further includes performing a middle-ear muscle reflex threshold test on the patient using the test system and performing one or more other auditory tests on the patient (i.e., the one or more other auditory tests comprise at least one of an otoacoustic emission test, an acoustic reflectance test comprising at least one of an ambient pressure acoustic reflectance test and a reflectance tympanometry test using a pump to vary static pressure, an auditory brain stem response test, and an otoacoustic emission test of medial olivocochlear status) Yet further, the method include analyzing results of the middle-ear muscle reflex threshold test and results of the one or more other auditory tests and providing an output to the user representative of a probability of an auditory impairment in function of the patient's auditory system based on both the results of the middle-ear muscle reflex threshold test and the results of the one or more other auditory tests.

Still further, another method for use in assessing auditory function includes providing a test system for use in performing one or more auditory tests on a patient. The test system includes a processing apparatus operable to initiate one or more tests upon receipt of input from a user and a probe electrically coupled to the processing apparatus and configured to be acoustically coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals). The method further includes performing, with use of the test system, at least one of an acoustic test of volume of air between the probe and the eardrum of the patient, an acoustic test of ear canal cross-sectional area at two or more locations along an axis of the ear canal of the patient, and an acoustic test of ear canal length of the patient between a tip of the probe and the eardrum. The method further includes performing an acoustic reflectance test using the test system.

Yet further, still another method for use in assessing auditory function includes providing a test system for use in performing one or more auditory tests on a patient. The test system includes a processing apparatus operable to initiate one or more tests upon receipt of input from a user and a probe electrically coupled to the processing apparatus and configured to be acoustically coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals). The method further includes performing an acoustic reflectance test using the test system resulting in acoustic reflectance data and performing an audiometry test using the test system resulting in audiometry data.

In one or more embodiments of system or methods summarized herein, a handheld enclosure may be provided that includes the processing means configured for at least initiating one or more tests upon receipt of input from a user. The probe is electrically coupled to the processing means within the handheld enclosure. Further, the processing means within the handheld enclosure may be configured for communication of information to a base unit (e.g., the base unit including base unit processing means for use in processing the information).

A system for use in fitting a hearing aid is also described. The system includes a probe configured to be coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals) and a processing apparatus operable to initiate one or more auditory tests on a patient upon receipt of input from a user. The processing apparatus is operable for use in initiating and controlling performance of an acoustic reflectance test resulting in acoustic reflectance data and an output device is included to provide an output based on at least the acoustic reflectance data for use in adjusting one or more parameters of the hearing aid.

In one embodiment of the hearing aid fitting system, the system further includes a hearing aid. The hearing aid includes at least the processing apparatus and probe with the at least one acoustic transmitter and the at least one acoustic transducer to measure an acoustic response in the ear.

Further, in one or more embodiments of the hearing aid fitting system, the output device may provide an output based on at least the acoustic reflectance data for use in adjusting one or more parameters of the hearing aid to modify at least one of automatic gain control of the hearing aid, linear amplification of the hearing aid, compression limiting of the hearing aid, wide dynamic range compression of the hearing aid, syllabic compression of the hearing aid, and attack and release times of the hearing aid.

Further, in one or more embodiments of the hearing aid fitting system, the output device may provide an output based on at least the acoustic reflectance data for use in adjusting one or more parameters of the hearing aid to compensate for effects of middle-ear dysfunction or may provide a warning signal to a user if the acoustic reflectance test detects a probable middle-ear dysfunction or conductive hearing loss.

Further, in one or more embodiments of the hearing aid fitting system, the processing apparatus may be operable for use in initiating and controlling performance of one or more other auditory tests on the patient in addition to the acoustic reflectance test, wherein the one or more other auditory tests comprise at least one of an admittance tympanometry test, an Eustachian tube test, a middle-ear muscle reflex threshold test, an otoacoustic emission test of medial olivocochlear status, an otoacoustic emission test, an acoustic test of eardrum response based on probe response, an acoustic test of volume of air between the probe and eardrum, an acoustic test of ear canal cross-sectional area, an acoustic test of ear canal length, an auditory brain stem response test, and an audiometry test.

Further, in one or more embodiments of the hearing aid fitting system, the processing apparatus may be operable for initiating and controlling performance of an ambient pressure acoustic reflectance test or a reflectance tympanometry test.

Still further, in one or more embodiments of the hearing aid fitting system, the processing apparatus may be further operable for initiating and controlling performance of an audiometry test resulting in audiometry data. In such embodiments, the output device provides an output based on an analysis of the audiometry data and the acoustic reflectance data for use in adjusting one or more parameters of the hearing aid.

Further, in one or more embodiments of the hearing aid fitting system, the processing apparatus may be further operable for controlling performance of a measurement of at least one of a sound pressure level and an acoustic transfer function at the eardrum as an eardrum test estimate using the ear canal measurements (i.e., the eardrum test estimate based on measurements at the probe tip located in the ear canal some distance away from the eardrum) and may be operable to analyze the audiometry data based on the eardrum test estimate to control for acoustic standing wave effects that otherwise hinder the interpretation of audiometry data at high frequencies in the ear canal.

Further, in one or more embodiments of the hearing aid fitting system, the processing apparatus may be operable to use one or more ear canal measurements to estimate at least one of sound pressure level and acoustic transfer function at the eardrum for use in fitting of a high-frequency hearing aid.

A method for use in fitting a hearing aid is also described that includes providing a test system for use in performing one or more auditory tests on a patient, wherein the test system includes a processing apparatus operable to initiate one or more tests upon receipt of input from a user and a probe electrically coupled to the processing apparatus and configured to be acoustically coupled into an ear canal (i.e., the probe comprises at least one acoustic transmitter to present one or more acoustic stimulus signals into the ear canal, and further wherein the probe comprises at least one acoustic transducer to measure an acoustic response to the one or more acoustic stimulus signals). The method further includes performing an acoustic reflectance test using the test system resulting in acoustic reflectance data and fitting a hearing aid for the patient using results of at least the acoustic reflectance test.

In one embodiment, fitting a hearing aid for the patient includes using results from the acoustic reflectance test to adjust one or more of the parameters of the hearing aid to modify at least one of automatic gain control of the hearing aid, linear amplification of the hearing aid, compression limiting of the hearing aid, wide dynamic range compression of the hearing aid, syllabic compression of the hearing aid, and attack and release times of the hearing aid.

A hearing aid system is also described that includes at least one acoustic transmitter in a hearing aid to present one or more acoustic stimulus signals into the ear canal, at least one acoustic transducer in the hearing aid to measure an acoustic response to the one or more acoustic stimulus signals, and a processing apparatus in the hearing aid operable to initiate one or more auditory tests on a patient. The processing apparatus is operable for use in initiating and controlling performance of an acoustic transfer function test (e.g., an acoustic reflectance test or an acoustic admittance test) resulting in acoustic transfer function data and is operable for use in adjusting one or more parameters of the hearing aid based on at least the acoustic transfer function data.

A method for adjusting a hearing aid is also provided that includes providing a hearing aid that comprises at least one acoustic transmitter to present one or more acoustic stimulus signals into the ear canal and at least one acoustic transducer to measure an acoustic response to the one or more acoustic stimulus signals, and initiating and controlling performance of an acoustic transfer function test (e.g., an acoustic reflectance test or an acoustic admittance test) resulting in acoustic transfer function data using the hearing aid. One or more parameters of the hearing aid are adjusted based on at least the acoustic transfer function data.

In one or more embodiments of the hearing aid system or hearing aid adjustment method, the method and system may be operable to adjust one or more parameters of the hearing aid to modify at least one of automatic gain control of the hearing aid, linear amplification of the hearing aid, compression limiting of the hearing aid, wide dynamic range compression of the hearing aid, syllabic compression of the hearing aid, and attack and release times of the hearing aid.

In one or more other embodiments of the hearing aid system or hearing aid adjustment method, the adjustment may be to compensate for effects of middle-ear dysfunction (e.g., otitis media, eardrum perforation, ossicular discontinuity, and otosclerosis) based on at least the acoustic transfer function data and/or a warning signal may be provided if the acoustic transfer function test detects a probable middle-ear dysfunction or conductive hearing loss.

It will be recognized that one or more of the functions carried out by the systems (e.g., the processing apparatus of the systems) may be included as one or more steps that form a part of the methods that can be implemented using the respective systems.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

Figure 1:
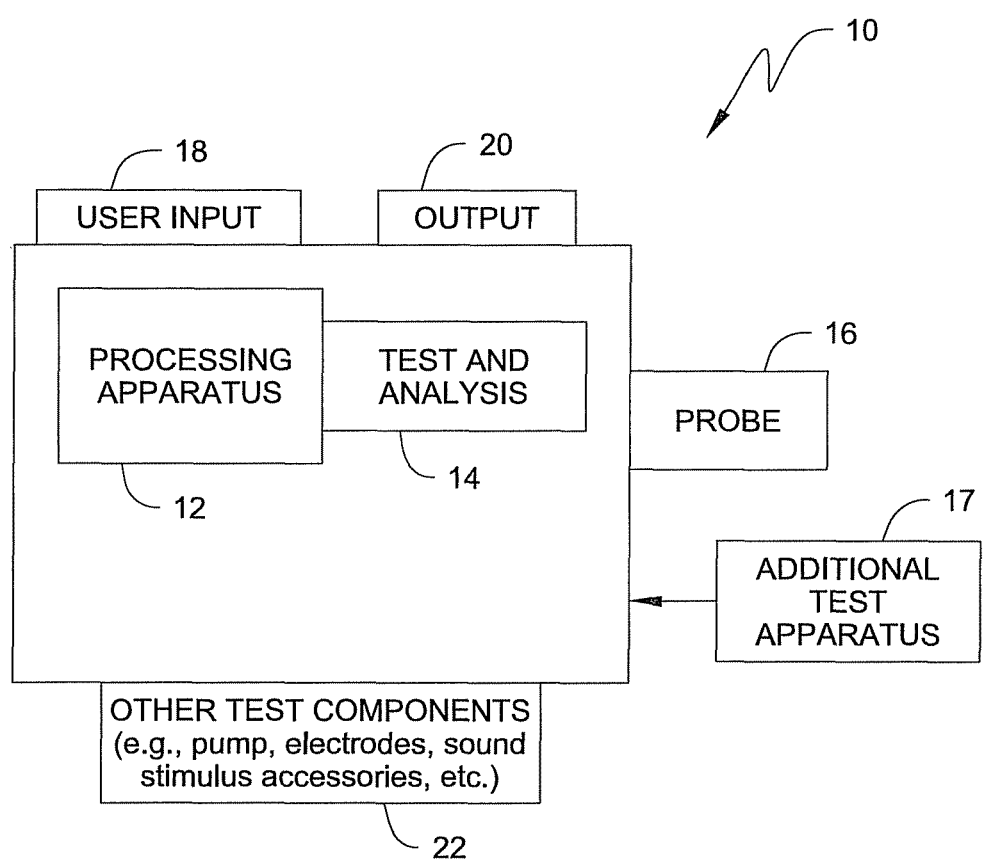
FIG. 1 is a generalized functional block diagram of one embodiment of an auditory test battery system according to the present invention.

Generally, exemplary embodiments of an auditory test battery system 10 and test battery method 50, according to the present invention, shall be described with reference to FIGS. 1 and 6, respectively. Various illustrative embodiments of such systems and methods, including reflectance tympanometry methods and systems (e.g., those that include feedback control) that may be used alone or in combination with such test battery systems and methods, shall thereafter be further described with reference to FIGS. 2-5 and 7-11.

One skilled in the art will recognize from the description herein that various illustrative embodiments described herein include some features or elements included in other illustrative embodiments and/or exclude other features or elements. However, a test battery system or method, according to the present invention, may include any combination of features or elements selected from one or more of the various embodiments as described herein with reference to FIGS. 1-11. For example, one or more embodiments of a test battery system and method may include use of reflectance tympanometry with or without feedback control, one or more embodiments of a test battery system and method may include use of ambient pressure acoustic reflectance measurements rather than reflectance tympanometry, one or more embodiments of a test battery system and method may include use of an acoustic reflectance test or does not need to include such an acoustic reflectance test, one or more embodiments of a test battery system and method may include use of an audiometry test for use in fitting a hearing aid, and/or one or more embodiments may be used for diagnostic or screening purposes. Yet further, one or more embodiments may use the same test instrument (e.g., probe) to perform multiple tests of a test battery or may use different individual test instruments (e.g., each with a separate or shared probe according to the requirement) to perform such tests. In either case, the results of such tests may be processed (e.g., by a personal computer) to provide outputs as described herein. In other words, one skilled in the art will readily recognize that any number of various embodiments of test battery systems and/or methods may benefit from one or more of the features described herein.

Generally, according to one aspect of the present invention, a system is provided for the measurement of an acoustic reflectance of the ear as a function of static pressure in the ear canal and sound stimulus parameters, which include frequency or time, in which the system includes a feedback system designed to maintain the actual static pressure approximately equal to the intended static pressure. Such a system allows a user to make more accurate acoustic reflectance measurements in patients, in whom it is sometimes difficult to establish a leak-free insertion of a probe assembly into an ear canal of the patient. For example, a feedback circuit can monitor the success of the acoustic reflectance tympanometry system in creating an actual static pressure in the ear canal that is close to the static pressure intended in the implementation of an acoustic reflectance tympanometry test. Such a system may be used to perform reflectance tympanometry alone (e.g., a single or individual auditory test) or may be used as part of a test battery system that can be used to perform more than a single test.

In one embodiment of the system provided for the measurement of acoustic reflectance, an electrical signal representing the actual static pressure is measured by the system, so that the error in static pressure between the intended and actual pressure is measured by the system and reported to the operator. If the error is sufficiently large, as would be the case when the probe assembly has a leaky fit in the ear canal, and thus in which the static pressure pump would be unable to maintain a different pressure from atmospheric pressure for any significant duration, then the operator is alerted to adjust the probe fit or take other appropriate actions.

In addition to existing systems that measure acoustic reflectance in the ear as a function of static pressure and frequency or time, one embodiment of the system according to the present invention includes a static pressure transducer to measure ear-canal static pressure and a pump control unit that functions in the feedback system to maintain the measured static pressure approximately equal to the intended static pressure. The pump control unit may be a part of the main signal-processing unit of the system or a subsystem with bi-directional signal transmission with the main signal processor to enable the feedback loop to operate between the main signal processing unit of the system and the static pressure pump.

Further, in one embodiment of the system for the measurement of acoustic reflectance, the main signal processing unit is a digital computer. The pump control unit is a subsystem distinct from the main signal processor. The main signal processor is able to transmit electrical signals to the pump control unit, and receive electrical signals from the pump control unit. The pump control unit is able to transmit electrical signals to the main signal processor, and receive electrical signals from the main signal processor. The pump control unit transmits a signal to the pump so that an intended static pressure is produced, and receives an electrical signal from the static pressure transducer indicating the actual static pressure.

A feedback circuit is implemented in the main signal processor, which could be embodied as computer software or in hardware on a circuit card or other electrical component, to adjust the signal that the pump control unit transmits to the pump so that the intended and actual static pressures are approximately equal. This feedback circuit acts while the main signal processor is varying the static pressure in the ear canal over a range of clinically useful static pressures, (e.g., in the range from about minus 400 daPa to 400 daPa, where 100 daPa is the same pressure as 0.145 psi), and in which the main signal processor is measuring an acoustic reflectance of the ear as a function of static pressure and time or frequency.

Generally, according to another aspect of the present invention a system and/or method provides the use of a combination of tests to assess the functional status of the auditory system (e.g., the peripheral auditory system). The auditory system is the sensory system for hearing, and is comprised of the ear and the neural auditory systems. The ear is comprised of the external ear, including pinna and ear canal, the middle ear and the inner ear (or cochlea), which includes inner hair cells and outer hair cells. The neural auditory systems include the nerve fibers that innervate the cochlea and are part of the auditory nerve, the brainstem system, which include the cochlear nucleus, superior olivary complex and inferior colliculus, the thalamus systems, which includes the medial geniculate nucleus, and various specialized sites in the auditory cortex. Tests of the functional status of the auditory system include hearing tests that are correlated to the functioning of the auditory system, and physiological tests of the auditory system. Many but not all tests described herein relate to functional tests of the peripheral auditory system, which includes the ear and the auditory neural systems below the brainstem level. In response to sensory stimulation, e.g., an acoustic stimulus presented in the ear canal, a hearing test relates a patient's subjective report or response to the overall functioning of the patient's auditory system at peripheral and central levels. The MEMR test and the OAE test of the medial olivocochlear (MOC) efferent system are each a test of the patient's auditory system at both peripheral and central levels, because the MEMR and MOC systems involve efferent system responses from sites in the brain back to the ear.

Such a system and/or method may combine test results of the status of the external and middle-ears with the status of the cochlea, the auditory nerve, the specific brain regions serving auditory perception, or some combination thereof. The functional assessment of the peripheral auditory system is improved by the use of multiple tests that provide complementary information on auditory processing in response to sound stimuli at various levels of the peripheral auditory system.

Because sound energy is typically transmitted through the external ear and middle-ear before that energy influences the cochlea, auditory nerve or related functional centers in the brain, the function of the external and middle-ears constrains the interpretation of cochlear and neural responses. Thus, in screening and diagnosing auditory system dysfunction in patients, it is useful to compare tests indicative of cochlear and auditory nerve status with tests indicative of external and middle-ear function. A middle-ear muscle reflex (MEMR) test of middle-ear muscle activity is an indirect measure of cochlear and auditory-nerve functioning, because neural efferents are responsible for activating the MEMR via a change in the state of the stapedius muscle, which is a middle-ear muscle. By combining multiple tests of the peripheral auditory system in a single device, the overall clinical assessment of peripheral auditory system function can be improved.

As will be described further herein with respect to the FIGS. 1-11, one particular auditory test of the status of the external and middle-ears is the test of the acoustic reflectance of the ear, which can be performed as an ambient pressure reflectance test or as a reflectance tympanometry test. Generally, at least in one embodiment, a probe including the capability to deliver an acoustic sound stimulus and measure an acoustic response is inserted into the ear canal and used for the reflectance test. The ambient pressure reflectance test is defined as an acoustic reflectance of the ear test performed at ambient, or atmospheric, static pressure in the ear canal. The reflectance tympanometry test, which may or may not include a feedback circuit as described herein to control static pressure, is an acoustic reflectance of the ear test performed by inserting a probe in a substantially leak-free manner in the ear canal and pressurizing the ear canal using a static pressure pump.

As used herein inserting a probe in the ear canal in a substantially leak-free state refers to a state such that a pressure pump is able to maintain a desired pressure in the ear canal different from atmospheric pressure for a significant duration (e.g., sufficient duration to perform a desired auditory test). If the pump is unable to maintain such pressure in the ear canal than the probe is not in a substantially leak-free state.

In many cases, an acoustic reflectance test (i.e., an ambient pressure acoustic reflectance test or a reflectance tympanometry test) is confused with other types of tests having similar names. An acoustic reflectometry test is described in U.S. Pat. Nos. 4,601,295 and 4,459,996 to Teele, issued 22 Jul. 1986 and 17 Jul. 1984, respectively, and both entitled "Ear Pathology Diagnosis Apparatus and Method," that differs fundamentally from the acoustic reflectance tests described in the present application, because the tests described by Teele are not calibrated acoustic transfer functions. Each of the acoustic reflectance tests (i.e., an ambient pressure acoustic reflectance test or a reflectance tympanometry test) differs from an acoustic reflectivity or acoustic reflectometry test in the following manner: (1) acoustic reflectivity or acoustic reflectometry does not include a measurement of a calibrated acoustic transfer function (e.g., a calibrated iso-level acoustic transfer function) of the ear as does acoustic reflectance measured in an acoustic reflectance test, and (2) an acoustic reflectivity or acoustic reflectometry test uses a probe that is not sealed in the ear canal in a substantially leak-free manner whereas a typical acoustic reflectance test does use a probe that is sealed in the ear canal in a substantially leak-free manner. Further, an acoustic reflectivity or acoustic reflectometry test is also called a spectral gradient acoustic reflectometry test in the literature.

Further, an "acoustic reflectance curve" test described in U.S. Pat. No. 5,699,809 to Combs, et al., issued 23 Dec. 1997, and entitled "Device and Process for Generating and Measuring the Shape of an Acoustic Reflectance Curve of an Ear," has the same properties as described above in (1) and (2) provided with reference to the acoustic reflectivity test. Further, the acoustic reflectance curve test lacks the desired properties of the acoustic reflectance test described herein. Thus, the acoustic reflectance test of the ear as used herein is fundamentally different from the acoustic reflectance curve test as described in the literature. In addition, the acoustic reflectance curve test lacks pressurization in the ear canal, and thereby differs still further from a reflectance tympanometry test.

In the present invention, the acoustic reflectance of the ear is an acoustic transfer function (e.g., an iso-level acoustic transfer function) of the ear; namely, the acoustic transfer function is based on a one-dimensional acoustic transmission line description of the sound field in the ear canal that is defined, at least in one embodiment, in the frequency domain by the complex ratio of the reflected pressure signal at a given frequency to the incident pressure signal at the same frequency.

Further, "otoreflectance" used in the scientific literature, Douglas H. Keefe, "Otoreflectance of the cochlea and middle ear," *J. Acoust. Soc. Am.* 102, 2849-2859 (1997), refers to acoustic pressure reflectance measurements in the ear canal, by the use of a substantially leak-free insertion of a probe assembly, in the frequency or time domain over a range of two or more stimulus signals (i.e., over a range of two or more stimulus signals with varying amplitude). Otoreflectance measurements differ from ambient pressure acoustic reflectance measurements that use a single stimulus level in that otoreflectance measures a nonlinear, or stimulus level-dependent change, in the acoustic reflectance function. This is preferred inasmuch as the nonlinear otoreflectance includes response information on cochlear functioning whereas the acoustic reflectance measurement does not.

As further described herein with reference to one or more embodiments, to assess non-invasively in human patients the functioning of the peripheral auditory system in a more nearly complete fashion, the ambient pressure acoustic reflectance test or the reflectance tympanometry test may be combined with one or more other auditory tests to form a test battery. Such auditory tests may include an acoustic admittance tympanometry test resulting in an admittance tympanogram or data representative thereof, a test of the acoustic middle-ear muscle reflex threshold, a supra-threshold test of reflex decay, a tympanometric test of Eustachian tube dysfunction, a test of evoked otoacoustic emissions (OAF) (e.g., sounds measured in the ear canal with an origin in the cochlear-mechanical response to a sound stimulus presented in the ear canal), an acoustic test to determine the volume of air enclosed between the tip of the probe used in an acoustic reflectance test and the eardrum, an acoustic test to determine the cross-sectional area of the ear canal at two or more locations along an axis of the ear canal (e.g., used to determine variability of the ear canal cross-sectional area along the axis thereof), an acoustic test to determine the length of the ear canal between the probe tip and the eardrum, an acoustic test to estimate the acoustic pressure or acoustic admittance or acoustic reflectance at the eardrum based on responses measured by a probe microphone located some distance away from the eardrum, an auditory brainstem response (ABR) test, and a behavioral audiometric test.

It should be recognized that the acoustic test to determine the volume of air enclosed between the tip of the probe used in the acoustic reflectance test and the eardrum, the acoustic test to determine the cross-sectional area of the ear canal at two or more locations along an axis of the ear canal, and the acoustic test to determine the length of the ear canal between the probe tip and the eardrum do not constitute tests of the functioning of the peripheral auditory system, but rather are used with the acoustic response measured at the probe to estimate the acoustic response at some other location in the ear canal, for which the most clinically relevant location is at the eardrum. The response in the ear canal between the probe tip and the eardrum can differ substantially at higher frequencies, particularly above approximately 4 kHz in the adult ear. A combination of tests to measure the eardrum response at higher frequencies in the range of hearing has potential clinical advantages in assessing middle-ear functioning, hearing-aid fitting and in interpreting outcomes of cochlear, neural and behavioral tests at high frequencies. The types of eardrum responses include at least one of the sound pressure level and phase at the eardrum and acoustic transfer functions such as acoustic admittance and acoustic reflectance at the eardrum. A combination of other auditory tests in the test battery may provide information that is indicative of the functioning of the peripheral auditory system.

The present invention, at least in one embodiment, describes the combination of various tests that when performed using the same test system provide one or more benefits as opposed to the test being performed individually, analyzed individually, and not considered in combination. However, in some circumstances, individual tests performed using individual testing apparatus, but having the results thereof analyzed in combination as described herein, may also be beneficial. For example, and not to be taken as limiting to the present invention, the test battery may include the use of an ABR test.

In contrast to other tests listed herein, the ABR is an auditory evoked electrical potential in response to an acoustic sound stimulus presented in the ear canal. An ABR response is measured using signals recorded from at least one electrode, but preferably two or three electrodes, that are affixed to the skin of the patient's head so as to obtain a good electrical connection. The ABR test can detect damage to the auditory nerve and auditory pathways in the brainstem and can be used to predict the presence of a sensorineural hearing loss. Such a sensorineural hearing loss is distinct from a conductive hearing loss in that sensorineural hearing loss has its functional origin in cochlear dysfunction or in the auditory nerve and auditory pathways. In one embodiment, the ABR test is performed by attaching three electrodes on the head and measuring the electric potential between an electrode pair as a sound stimulus is repetitively presented. The ABR is typically obtained as a time average of the electrical response measured to the repetition of a sound stimulus; the electrical noise associated with the ABR is also measured to construct a measure of the extent to which the ABR signal plus noise differs from the ABR noise.

OAE and ABR tests have relevance to newborn hearing screening (NHS) programs to identify hearing loss. The addition of an acoustic reflectance test has relevance to such a NHS program because of its ability to identify middle-ear dysfunction.

Each of the ABR and audiometric tests can be either of the air-conduction type, the bone-conduction type, or both. The air-conduction test supplies the sound stimulus through a probe inserted in the ear canal in the manner described herein or using a free sound field. The bone-conduction test applies the stimulus using a bone vibrator, which is typically placed behind the ear in contact with the skin, and which generates a vibration of the skull and thence to the cochlea through multiple pathways in response to an electrical stimulus applied to the input of the bone vibrator.

A generalization of the OAE test is used to test the functioning of the medial olivocochlear (MOC) region of the brain. Efferent nerves from the MOC region terminate on the outer hair cells in the cochlea or inner ear, and the function of these outer hair cells is closely related to the ability of human hearing to analyze a complex sound into its frequency-specific components. The MOC efferents provide a neural feedback mechanism that affects the function of the cochlea. In one embodiment of the present invention, by combining the OAE measurement with the presentation of an activator signal in the same ear as is presented the OAE test stimulus, in the opposite ear, or in both ears, it is possible to test the functional status of the MOC system. Here, the term activator signal is understood to refer to an activator of the MOC efferent system, and in one embodiment uses a wideband noise signal as the activator.

A class of auditory pathologies collectively referred to as auditory neuropathy have in common that patients with an auditory neuropathy typically lack both MOC and MEMR function, which each include a neural efferent control of peripheral auditory mechanics. Yet some auditory neuropathy patients have OAE responses in the normal range. In one embodiment of the present invention described herein, the combination of an acoustic reflectance test with at least one of an OAE test of MOC function and a MEMR test can be used to identify patients at risk for auditory neuropathy. Further, such a combination of tests to detect auditory neuropathy would be useful in NHS programs, in that the acoustic reflectance form of the MEMR test has advantages in testing of infants' ears. For example, the MEMR test based on acoustic reflectance can measure a MEMR shift at high frequencies and measurements are possible using only a single test ear. Although both ears of an infant might be tested in a NHS program, it is advantageous for a test battery to provide a result using a single test ear because it is inconvenient to simultaneously couple transducers to both ears of an infant.

In standard clinical practice, the acoustic-reflex test in an acoustic immittance battery sets the static pressure in the ear canal using a pump at the tympanometric peak pressure of a low-frequency immittance tympanogram. This provides the largest possible MEMR shift, which is typically detected at 226 Hz. Because the non-immittance types of acoustic-reflex testing may be more sensitive than the clinical testing in the acoustic immittance battery, e.g., because the measured MEMR thresholds may be lower in the non-immittance types of MEMR tests, these non-immittance MEMR tests can be performed at ambient static pressure. Alternatively, they can be performed at a slightly positive static pressure that tends to open the tiny ear canals found in newborn infants, and thus is more likely to provide an open acoustic pathway between the probe and the eardrum. The non-immittance MEMR tests detect a MEMR shift at higher frequencies than the 226 probe tone used in standard clinical testing, which leads to a larger MEMR shift and avoids the low-frequency problems (below 1000 Hz) that complicate the interpretation of acoustic immittance and acoustic reflectance responses in newborns and infants less than 6 months old (Keefe D H, Bulen J C, Arehart K H, and Burns E M (1993), "Ear-canal impedance and reflection coefficient in human infants and adults", *J. Acoust. Soc. Am.* 94, 2617-2638). These problems are related to an additional shunt pathway between the probe and eardrum, which is thought to involve a motion of the compliant and lossy ear-canal walls of infants. The MEMR threshold tests based on shifts in sound pressure and shifts in acoustic reflectance responses may provide advantages for use in infant testing by reducing the false-positive rates and increasing the identification of infants with auditory neuropathy and other diseases that result in elevated or absent MEMR thresholds. Also, the use of lower-level activator signals to measure the MEMR threshold may improve the safety of these tests.

Figure 6:
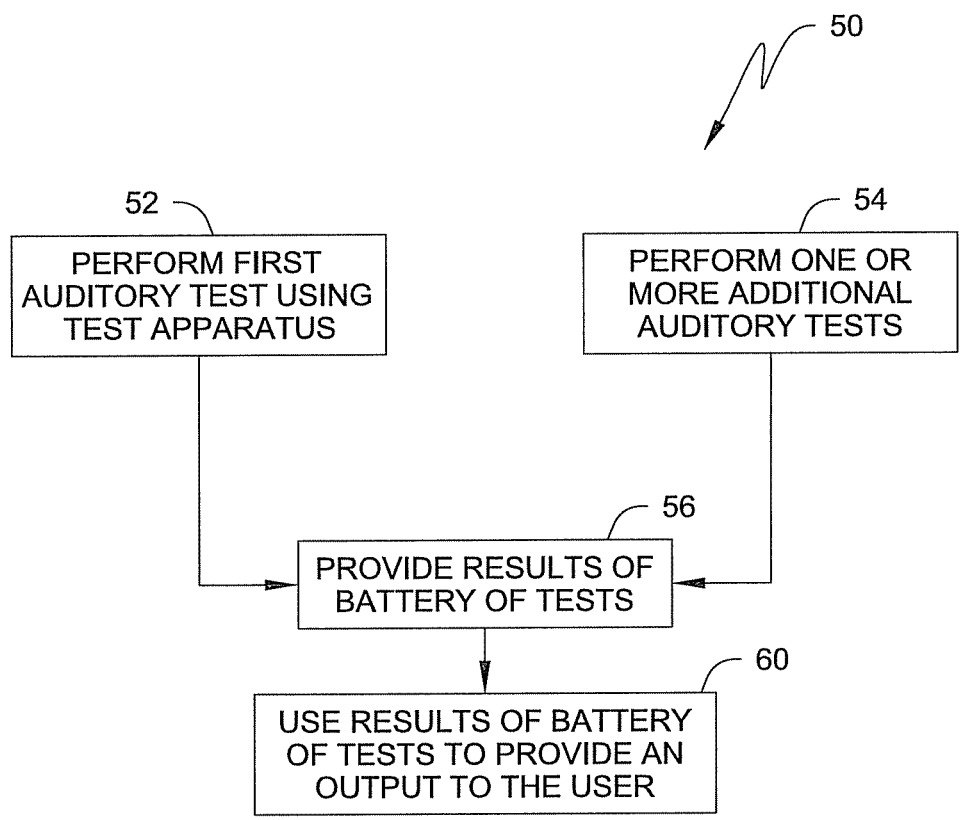
FIG. 6 is a flow diagram showing one embodiment of a generalized test battery method that may be implemented using the test battery system shown generally in FIG. 1 according to the present invention.

The auditory test battery system 10 generally shown in FIG. 1 can be used to implement the test battery method 50 shown generally in FIG. 6 to perform multiple auditory tests as described herein, or can be used to perform, for example, an acoustic reflectance test, alone or in combination with one or more other auditory tests as part of a test battery as described herein. Generally, the test battery system includes a processing apparatus 12 (e.g., one or more processing components either implemented using hardware and/or software such as by means of a computer, a dedicated digital signal processor, or a circuit board configuration) for performing functionality as described herein. For example, the processing apparatus 12 is configured to initiate one or more auditory tests upon receipt of input from a user via user input 18 of the system 10.

The test battery system 10 further includes a probe 16 electrically coupled to the processing apparatus (e.g., via a wired connection or a wireless transmission system between probe 16 and processing apparatus). In one embodiment, the probe 16 that can be coupled (e.g., acoustically coupled, or insertible) into an ear canal in a substantially leak-free state and includes, at least one acoustic transmitter to present one or more acoustic stimulus signals into the ear canal and at least one acoustic transducer to measure an acoustic response to the one or more acoustic stimulus signals. The probe is coupled into an ear canal prior to the test in the test battery.

Alternately, the probe 16 and its at least one acoustic transmitter and at least one acoustic transducer can also be included within the earmold of a hearing aid coupled into the ear canal, such that the earmold may also have a vent hole, thus removing the substantially leak-free insertion, to prevent the occlusion effect that is well known to audiologists who fit hearing aids. The presence of a vent hole predominantly influences the lower frequencies of an ear-canal measurement (particularly below 1000 Hz). If a vent hole is present in this earmold, then the probe 16 is not used with a pressure pump in a tympanometric test system, but the frequency range of the ambient-pressure acoustic transfer function measurement may be suitably restricted (to frequencies above approximately 1000-1500 Hz) so that information on middle-ear functioning can nonetheless be obtained using the test battery system 10.

In an open fit type of hearing aid, the earmold may be replaced by a dome or other apparatus within the ear canal, and small-diameter tubes may couple the one or more microphones and receiver transducers in the hearing aid, which is external to the ear canal, to the sound field within the ear canal. Thus, the hearing aid itself may function as the probe 16 in the invention, such that the hearing aid processor generates an electrical stimulus to create an acoustic stimulus in the ear canal and the microphone receives the response. The hearing aid is acting in a special test mode for a limited time to measure a wideband acoustic transfer function at the probe, and can further be used to measure a wideband acoustic transfer function at the eardrum, with the result used to estimate any conductive hearing loss or middle-ear dysfunction such as otitis media. By time averaging the response to the acoustic stimulus, the effect of environmental sound on the acoustic transfer function response is minimized.

In one embodiment of an open-fit hearing aid or a hearing aid with a substantial vent, the acoustic transfer function response is limited to approximately 1500 Hz and above and a two microphone technique is used to measure the acoustic transfer function as described in a published abstract (Keefe, D H, Ling R, Burns E M (1987), "Auditory system impedance measurement using the two-microphone wavetube technique," *J. Acoust. Soc. Am.* 81:S75), but in which the wavetube is replaced by two microphones coupled by small-diameter tubing to different locations in the ear canal separated by approximately 3-7 mm, and in Blayney A W, McAvoy G J, Rice H J, Williams K R ("An experimental technique for determining middle ear impedance," *Acta Otolaryngol.* 116, 201-204, 1996).

Hearing aids have previously been described, for example, in U.S. Pat. No. 4,548,082 to Engebretson, et al., issued 22 Oct. 1985, and entitled "Hearing Aids, Signal Supplying Apparatus, Systems for Compensating Hearing Deficiencies, and Methods," that include a microphone for sensing sound in the ear of the user of the hearing aid in response to a test signal generated by the hearing aid, but the present invention uses such a microphone signal to measure an acoustic reflectance or related acoustic transfer function such as wideband acoustic admittance and uses such a signal to measure or assess middle-ear dysfunction in the ear of the user of the hearing aid.

Generally, the probe with transducers is most often a probe that is inserted in a substantially leak-free manner into the ear canal, or otherwise coupled into the ear canal. In specialized applications, the probe and acoustic transmitter may be a headphone of the circumaural, supraaural or other types and a microphone may be spatially separated from the headphone and placed in the ear canal. In other specialized applications, for example, when the probe functionality is embedded in a hearing aid apparatus, either or both of the at least one acoustic transmitter and the at least one acoustic transducer to measure an acoustic response may include a transducer external to the ear canal and a small-diameter tube or other acoustic coupler extending to at least one location within the ear canal to deliver sound or to measure an acoustic response. As used herein, the components of such configurations are to be considered as being a part of the probe even though they are not necessarily all provided within a probe enclosure (e.g., they may be separately provided).

As further shown in FIG. 1, one or more other test components 22 form a part of the system 10 and may include components such as a pressure pump in systems that use tympanometry tests, electrodes in systems that perform ABR tests, sound stimulus elements in systems that perform tests requiring the use of other acoustic stimulus signals such as a contralateral acoustic stimulus signal, etc. One will recognize that the test battery system 10 includes all the components necessary to carry out the single or combination of auditory tests as described herein (e.g., one or more processors either part of the same test system or part of different test systems).

The processing apparatus 12 controls the performance of the one or more tests and obtains the results thereof for analysis. For example, as shown in FIGS. 1 and 6, the processing apparatus 12 upon input from a user via user input 18 initiates and controls the performance of a first auditory test using the test battery system 10 (block 52) and, also thereafter, may upon input from a user via user input 18 initiate and control the performance of one or more additional auditory tests using the battery test system 10 (block 54). The processing apparatus 12 is associated with the appropriate hardware and/or software to initiate, control and collect information for such tests as indicated generally by test and analysis block 14. The results of such tests are provided for analysis (block 56) by the processing apparatus 12. The processing apparatus 12 uses the results of the battery of tests to provide an output to the user (block 60) via the output 20 of the test battery system 10. The output may be provided in any possible manner, such as with use of a display, a printer, a speaker, or any other output type that relays information to the user.

In one embodiment, the system 10 may include one or more additional test apparatus 17 including, for example, processing apparatus associated with the appropriate hardware and/or software to initiate, control and collect information for one or more of the tests described herein. For example, the separate and additional test apparatus or instrument may include processing components (as well as other components necessary to carry out one or more tests) to initiate and control one or more tests of the test batteries described herein, or may be controlled by processing apparatus 12. Information to be analyzed together is collected from such separate instruments and provided for analysis (block 56) by the processing apparatus 12 or any other processing apparatus that provides an output (e.g., an output that takes into consideration the results of multiple tests; for example, providing a probability of auditory neuropathy) such as described herein (e.g., a personal computer having access to the results of the multiple tests and suitable software/hardware to analyze the results in combination to generate an output).

The present invention and/or one or more portions thereof may be implemented in hardware or software, or a combination of both. For example, the functions described herein may be designed in conformance with the principles set forth herein and implemented as one or more integrated circuits using a suitable processing technology.

As another example, the present invention may be implemented using one or more computer programs executing on programmable computers, such as computers that include, for example, processing capabilities, data storage (e.g., volatile and nonvolatile memory and/or storage elements), input devices, and output devices. Program code and/or logic may be applied to input data to perform functionality described herein and generate desired output information. The output information may be applied as an input to one or more other devices and/or processes, in a known fashion.

Any program used to implement the present invention may be provided in a high level procedural and/or object orientated programming language to communicate with a computer system. Further, programs may be implemented in assembly or machine language. In any case, the language may be a compiled or interpreted language.

Any such computer programs may preferably be stored on a storage media or device (e.g., read-only memory (ROM), other static memory or magnetic disk) readable by a general or special-purpose program, computer, or a processor apparatus for configuring and operating the computer when the storage media or device is read by the computer to perform the procedures described herein. The system may also be considered to be implemented using a computer readable storage medium, configured with a computer program, where the storage medium so configured causes the computer to operate in a specific and predefined manner to perform functions described herein. In view of the above, it will be readily apparent that the functionality as described herein may be implemented in any manner as would be known to one skilled in the art.

It is also readily apparent that the present invention may be adapted to be operable using any processing system, e.g., personal computer, and further, that the present invention is in no manner limited to any particular processing system. The amount of memory of the systems should be sufficient to enable the user to allow for operation of appropriate software and store data resulting from such operation. It is readily apparent that such memory may be provided by peripheral memory devices to capture relatively large files resulting from operation of the system. The system may include any number of other peripheral devices as desired for operation of the system, such as, for example, the following respective devices: a display; a keyboard or other user input mechanism, including, for example, a mouse. However, it is readily apparent that the system is in no manner limited to use of such devices, nor that such devices are necessarily required for operation of the system.

Figure 2:
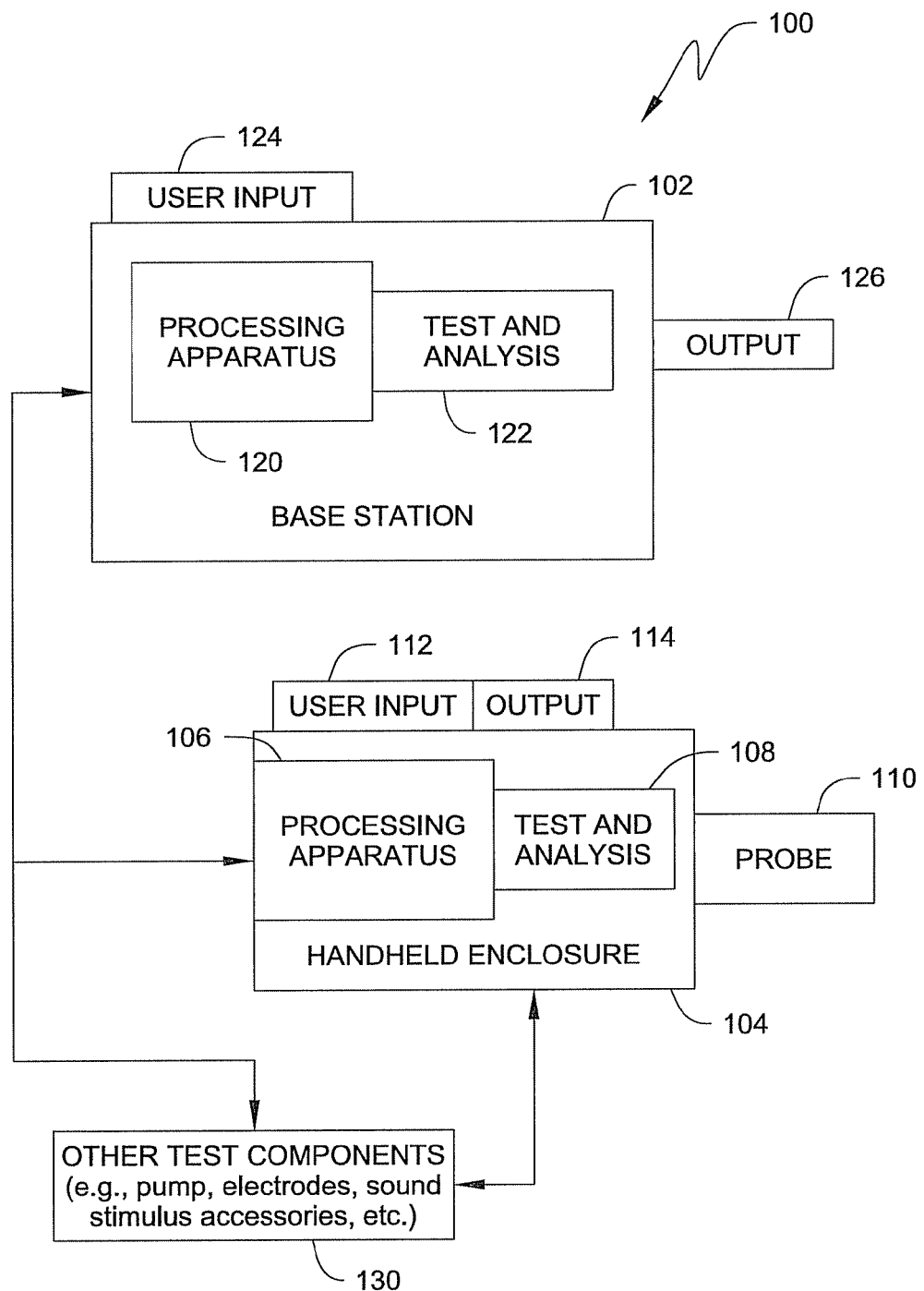
FIG. 2 is a functional block diagram of one embodiment of an auditory test battery system such as shown generally in FIG. 1 but which includes a handheld device and possibly, a base station.

In one embodiment, as shown in FIG. 2, a test battery system 100 may be a portable standalone test system including a handheld enclosure 104. The handheld enclosure 104 includes processing apparatus 106 therein for use in at least initiating one or more tests upon receipt of input from a user via user input 112. Further, a probe 110 is electrically coupled to the processing apparatus 106 within the handheld enclosure 104 (e.g., by cables and tubing).

The processing apparatus 106 may, in addition to initiating and/or controlling the one or more auditory tests, be configured for communication of information to a base unit 102 as shown in FIG. 2. The base unit 102 may include base unit processing apparatus 120 for use in processing the information provided from the handheld enclosure 104. However, one will recognize that the handheld device may operate completely independent of any other computer system and include all the processing capabilities necessary to carry out the functionality described herein within the handheld enclosure itself. Yet further, one or more embodiments of a test battery system (or a system that may only perform an individual test such as ambient pressure reflectance) may be encompassed within a hearing aid as further described herein. For example, acoustic transfer function tests including ambient pressure acoustic reflectance tests and acoustic admittance tests may performed by such a hearing aid embodiment for use in real-time adjustment of one or more parameters of the hearing aid.

One will recognize that the processing capabilities may be divided among the processing apparatus 120 of the base station 102 and the processing apparatus 106 of the handheld enclosure 104 as is indicated by the general inclusion of test and analysis components 122 and 108 respectively in both the base station 102 and handheld enclosure 104. Further, for example, the handheld enclosure 104 may provide an output 114 to a user, as may the base station 102 via output 126. Likewise, respective input devices 124 and 112 may be provided for both the base station 102 and handheld enclosure 104. Yet further, the test battery system 100 includes other test components 130 necessary to carry out the desired auditory tests which form a part of the test battery (e.g., pump, electrodes, etc.).

In other words, as opposed to use of a computer system with connection to a probe assembly to implement the one or more auditory tests described herein in one or more various combinations, the one or more test battery configurations described herein (e.g., including, or not including, an acoustic reflectance test of the ear) may be implemented using a portable device (e.g., the handheld enclosure 104) in which the probe assembly 110 and the cables and tubing are directly connected thereto, while there may also be a cable or a wireless connection to the base unit 102. If a wireless connection is used, for example, then a system to transmit and receive information must be present in both the base unit 102 and the portable device (e.g., the handheld enclosure 104), such that the base unit 102 can transmit signals that can be received and interpreted by the portable device 104, and the portable device (e.g., the handheld enclosure 104) can transmit signals that can be received and interpreted by the base unit 102. The portable device 104 may, but need not, be designed as a hand-held unit. Further, multiple handheld devices may be used to carry out different tests with results thereof transmitted to the base station (e.g., for analysis).

As described herein, portions of the function of the signal processing may be separated between the portable device (e.g., the handheld enclosure 104) and the base unit 102 in such a manner that the test battery system 100 performs properly. In one embodiment, the base unit 102 includes storage and archiving of data, a printout and other output capabilities, and networking. In another embodiment, the portable device (e.g., the handheld enclosure 104) includes a rechargeable battery for which the recharger is part of the base unit 102 or separated in a distinct module holding the portable device (e.g., the handheld enclosure 104) when not in use. The portable device (e.g., the handheld enclosure 104) and base unit 102 may be used to incorporate any of the test battery systems described herein.

For example, in a system implementing a test battery that includes an ABR test, electrodes used in the ABR test would be connected to the portable device (e.g., the handheld enclosure 104) from which signals are transmitted to the signal processing apparatus 106. In the alternative, for example, the electrodes used in the ABR test may be connected to the base unit 102 from which signals are transmitted to the signal processing apparatus 120.

Further, for example, for a system that implements a test battery that includes a contralateral acoustic stimulus signal in the ear opposite to the test ear produced by a contralateral driver, e.g., a loudspeaker, the electrical input to the contralateral driver may be received from a signal transmitted by the portable device (e.g., the handheld enclosure 104). Alternately, the electrical input to the contralateral driver may be received from a signal transmitted by the base unit 102.

One will recognize that various configurations for the test battery system to implement the desired combination of tests may be possible (e.g., multiple test apparatus providing results to a processing apparatus for analysis). However, at least in one embodiment, it is the benefit of performing such battery of tests in a single test system (e.g., using a single probe associated with the system, having the ability to perform the tests using one system that can then analyze results from the tests together, etc.) that provides the improved assessment capabilities described herein. As such, various known methods and system components may be used as part of the test battery system to carry out the battery of tests in the various combinations.

In one embodiment, the acoustic reflectance test (i.e., ambient-pressure reflectance test or reflectance tympanometry) may be carried out by the test battery system 10 in a manner and with components as described, for example, in U.S. Pat. No. 5,594,174 to Keefe and U.S. Pat. No. 5,651,371 to Keefe. One embodiment for calibration of the ambient-pressure reflectance device and for obtaining ambient-pressure reflectance data in a test ear is described in Keefe, D. H. and Simmons, J. L. (2003) ("Energy transmittance predicts conductive hearing loss in older children and adults," *J. Acoust. Soc. Am.* 114, 3217-3238) with one modification. One embodiment for calibration of the reflectance tympanometry device and for obtaining reflectance tympanometry data in a test ear is that described in the same publication (Keefe and Simmons, 2003) with the same modification. This modification is that, whereas Keefe and Simmons (2003) recommend that the area of the ear canal at the probe tip, which is used to calculate the acoustic reflectance in either the ambient-pressure reflectance test or reflectance tympanometry test, be set based on the probe tip size, the modified embodiment uses the area of the ear canal based upon the average cross-sectional area of the tubes included in the calibration tube set, which is used in calibrating the reflectance tympanometry device. One may select all tubes to have the same cross-sectional area with this area within approximately 25% of the cross-sectional area of the ear to be tested. It is useful to calibrate using a tube set with smaller tube areas in a device that will be used to measure acoustic reflectance data in the ears of infants and a tube set with larger tube areas in a device that will be used to measure acoustic reflectance data in the ears of adults.

An alternate embodiment is to acoustically estimate the area of the ear canal at the probe tip using techniques described in the literature (Keefe, D. H., R. Ling, J. C. Bulen (1992), "Method to measure acoustic impedance and reflection coefficient," *J. Acoust. Soc. Am.* 91, 470-485; Huang G T, Rosowski J J, Puria S, Peake W T (2000), "A noninvasive method for estimating acoustic admittance at the tympanic membrane," *J. Acoust. Soc. Am.* 108, 1128-1146).

Figure 3:
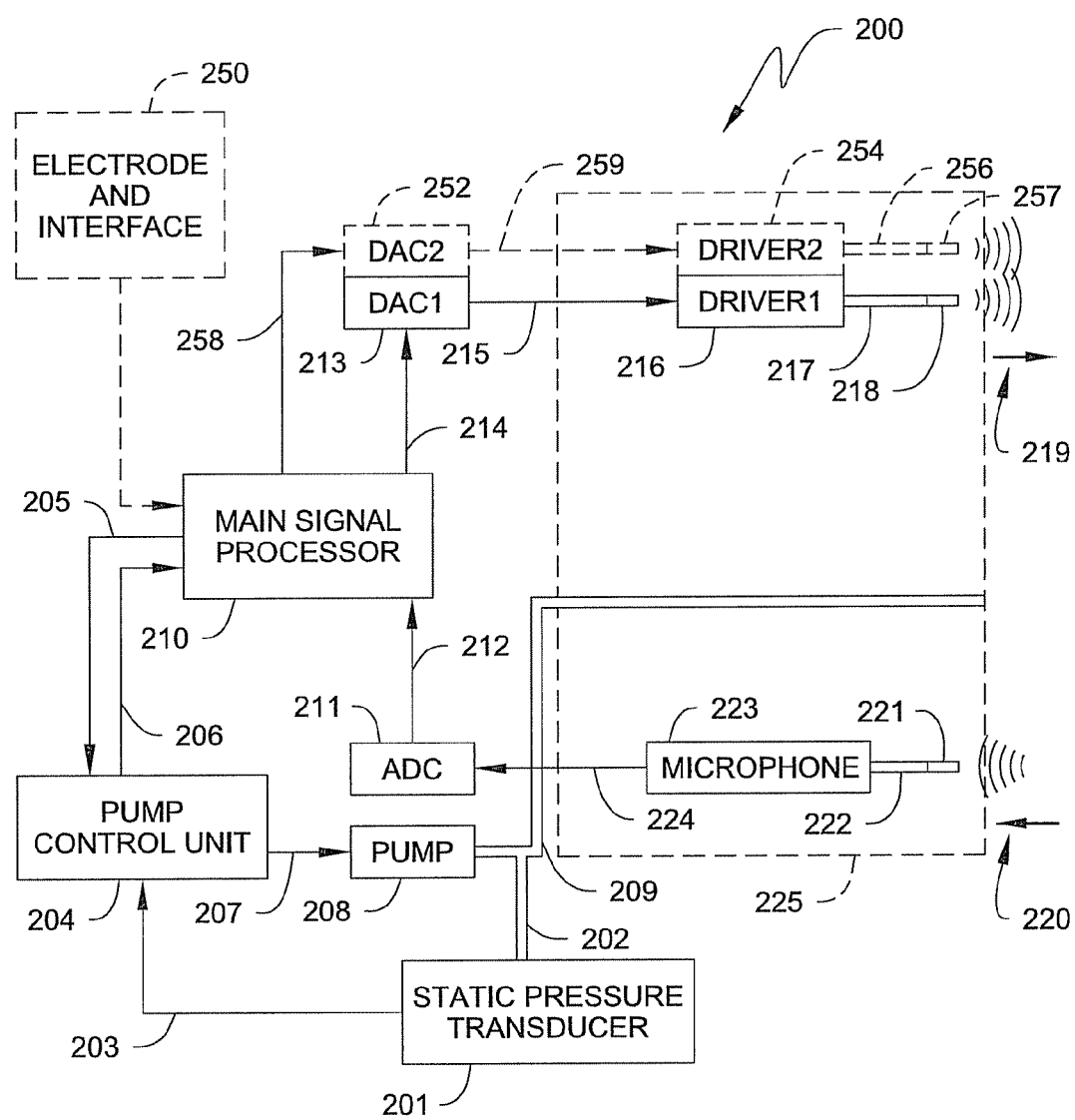
FIG. 3 is a functional block diagram of one embodiment of an auditory test system that includes a feedback control system for use in performing reflectance tympanometry alone, and/or combination with one or more other auditory tests like the test battery system shown generally in FIG. 1.

Yet further, one embodiment of reflectance tympanometry may be carried out (e.g., alone or in combination with one or more other auditory tests) using the system 200 shown in FIG. 3 that includes pump control feedback according to the present invention. The acoustic reflectance measurement is typically a wideband measurement using sound frequencies and measured responses over a broad frequency range (e.g., 0.25 to 8 kHz in some implementations).

The system 200 shown in the functional block diagram of FIG. 3 includes a main signal processor 210 that could be embodied on a computer, dedicated digital processor, or circuit board. The main signal processor 210 generates a stimulus signal 214 that is converted to an analog signal 215 by the digital to analog converter no. 1 (DAC1) 213. In an alternate embodiment, the system 200 may lack the DAC1 213 and the analog signal 215 is a copy of the stimulus signal 214. The analog signal is input to a driver 216 (e.g., a miniature loudspeaker).

The driver 216 is the source of an acoustic stimulus signal that is delivered to the ear through a tube or set of tubes 217 to a first part of a probe assembly 225 and then through a second tube or set of tubes 218 in a second part of the probe assembly 225, from which the sound stimulus 219 is delivered into the ear canal of a human patient. Prior to the measurement of a response to the sound stimulus 219, the probe assembly 225 is inserted in a substantially leak-free manner in the ear canal. In an alternate embodiment, the first and second parts of the probe assembly are identical and the tube or set of tubes 217 is identical to the tube or set of tubes 218.

A sound response 220 of the external and middle-ear to the sound stimulus 219 is transmitted into an inlet tube or set of tubes 221 of the probe assembly 225 and then through a tube or set of tubes 222 to the input of a miniature microphone 223, which, for example, typically includes a microphone preamplifier. The electrical output 224 of the microphone is a detected electrical analog signal that is converted into a digital response signal 212 by an analog to digital converter (ADC) 211. The response signal 212 is recorded by the main signal processor 210. In an alternate embodiment, the system 200 lacks the ADC 211, and the response signal 212 is a copy of the electrical output 224. In yet another alternate embodiment, the inlet tube or set of tubes 221 is identical to the tube or set of tubes 222.

Substantially simultaneously with the presentation of the stimulus signal 214 and the recording of the response signal 212, the main signal processor 210 transmits an intended static-pressure signal 205 to the pump control unit 204, and the pump control unit 204 transmits a driver signal 207 to the electrical input of the static pressure pump 208. The pump output generates a volume displacement of air into a tube or set of tubes 209 that is coupled to the probe assembly 225 sealed in the ear canal. This volume displacement of air generates a static pressure within the ear canal, which is sensed by a static pressure transducer 201 via inlet tube or set of tubes 202 that is coupled to the tube or set of tubes 209.

The probe assembly 225 is schematically represented as including the driver 216, microphone 223 and tubes or sets of tubes 217, 218, 221, 222, and 209. However, in one embodiment, the probe assembly 225 sealed in the ear canal includes only one tube 218 coupled to the driver 216, one tube 221 coupled to the microphone 223, and one tube 209 coupled to both the pump 208 output and the static pressure transducer 201 input. The present invention includes the possibility of a probe assembly with two or more drivers such as shown by optional Driver2 254, each of which may be a miniature loudspeaker. Such drivers 216 and 254 may each receive an analog signal 215, 259 from an associated digital to analog converter as represented by the dual DAC1 213 and digital to analog converter (DAC2 252), e.g., by converters that convert a stimulus signal 214, 258 generated by the main signal processor 210 to an analog signal, for use in providing an acoustic stimulus in the ear canal.

Multiple drivers are convenient when the probe assembly 225 is used to measure an acoustic reflectance response with an OAE response or with MEMR threshold and supra-threshold responses. Such measurements are obtained as a function of stimulus parameters to each driver as a function of time, frequency, or stimulus level.

The electrical output 203 of the static pressure transducer 201 is transmitted to the pump control unit 204, which transmits an actual static pressure signal 206 back to the main signal processor 210. The main signal processor 210 includes a feedback control circuit. For example, the feedback control circuit may be embodied in the main signal processor (e.g., a digital computing device) as a feedback control circuit implemented in software in which the intended static pressure signal is adjusted so that the actual static pressure measured in the ear canal is approximately equal to the intended static pressure to within some prescribed operating tolerance.

The design of such a feedback control circuit based on separate intended and actual measurements of a single variable, in this case the static pressure in the ear canal, and a prescribed operating tolerance, provides the necessary control to provide accurate static pressure in the ear canal and, thus, accurate reflectance measurements. In an alternate embodiment, the feedback procedure can reside in the pump control unit 204 rather than the main signal processor 210, which also follows from the description herein that the function of the pump control unit 204 may alternatively be included in the function of the main signal processor 210.

Figure 4:
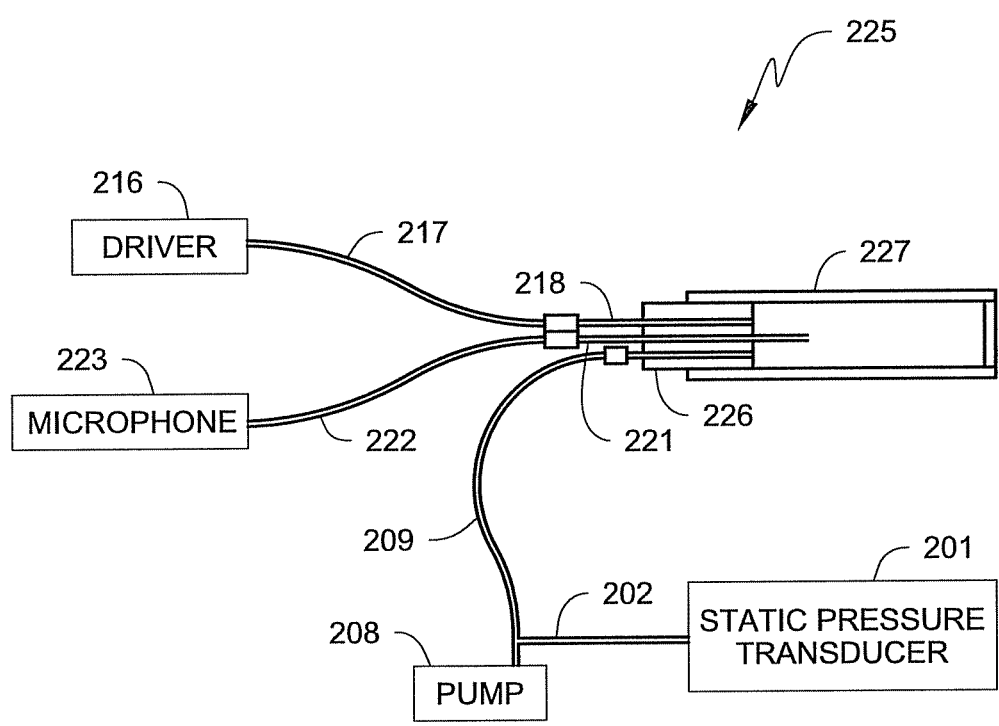
FIG. 4 is diagrammatic side view of the probe assembly shown in FIG. 3 in more detail.

Further details of one embodiment of the probe assembly 225 shown in FIG. 3 are represented in FIG. 4. FIG. 4 illustrates the components of the system 200 that are directly connected, each through a tube or set of tubes, to the probe assembly 225 and thence to the ear canal. The driver 216 output is the acoustic stimulus signal that is transmitted through a tube or set of tubes 217 to a tube or set of tubes 218 directly coupled to the probe assembly 225 through an eartip 226 that forms an air-tight seal between the body of the probe assembly 225 and the ear canal 227. The ear canal 227 is schematically illustrated by a cylindrical cross-section. The acoustic response signal in the ear canal is transmitted through inlet tube or set of tubes 221 of the probe assembly 225 to a tube or set of tubes 222 that is connected to the inlet of the microphone 223, such that, for example, the inlet is typically terminated by the diaphragm of the microphone 223.

The volume displacement of the static pressure pump 208 is connected to the probe assembly 225 by a tube or set of tubes 209 that is threaded through the eartip 226 into the ear canal 227. The inlet tube 202 of the static pressure transducer 201 is coupled to the tube or set of tubes 209 so that the static pressure measured is representative of the static pressure in the ear canal 227.

Properties of tube cross-sectional area and length constrain the ability of the static pressure transducer 201 to measure a static pressure that is representative of the static pressure in the ear canal 227. The intended static pressure is slowly varied so that pressure differences in the tubing systems and ear canal have sufficient time to equilibrate. The microphone 223 that typically includes a diaphragm, also typically includes a vent on the side of the diaphragm opposite to that of the inlet, and in a system with such a microphone the intended static pressure is slowly varied so that the pressure difference across the microphone diaphragm has sufficient time to equilibrate.

Figure 5A:
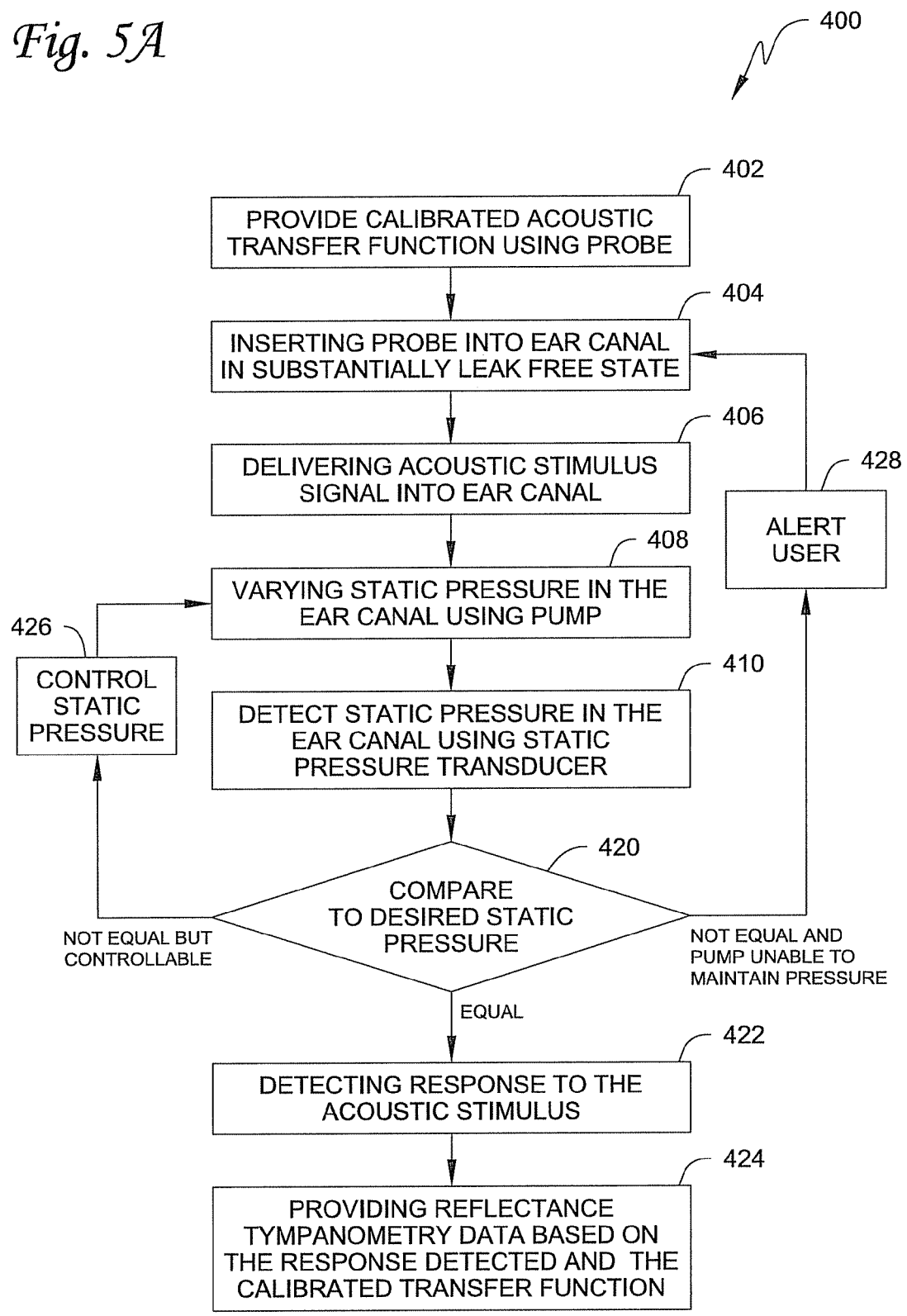
FIG. 5A is a flow diagram showing one embodiment of a reflectance tympanometry method with feedback control that may be implemented using the system shown in FIG. 3 according to the present invention.

FIG. 5A shows a flow diagram of one embodiment of a reflectance tympanometry method 400 with feedback control that may be implemented using the system shown in FIG. 3 according to the present invention. As shown therein, performing the reflectance tympanometry test on a patient using the test system shown in FIG. 3 includes providing a calibrated acoustic transfer function using the probe 225 (block 402). For example, as described in U.S. Pat. No. 5,594,174 to Keefe and U.S. Pat. No. 5,651,371 to Keefe, such calibration may be performed using one or more calibration tubes (not shown) at the time of testing the patient, or may be performed at any time prior to such testing. Detail with respect to such calibration is known and shall not be provided in any further detail herein.

The probe 225 is then inserted in the ear canal of the patient in a substantially leak-free state (block 404). An acoustic stimulus signal is delivered into the ear canal using the at least one acoustic transmitter (i.e., driver 254) of the probe 225 (block 408). Substantially simultaneously, the static pressure in the ear canal is controlled using the pump 208 (block 408).

The static pressure is controlled by detecting actual static pressure in the ear canal using the static pressure transducer 201 (block 410) and comparing the detected static pressure to a desired static pressure (block 420). The pump 208 is then controlled to maintain the desired static pressure in the ear canal based on the comparison of the desired static pressure to the actual static pressure (e.g., using pump control unit 204). For example, if the actual static pressure in the ear canal is not equal to the desired static pressure, then control static pressure loop 426 is used to adjust the static pressure (blocks 426 and 408).

Assuming that the actual static pressure in the ear canal is equal to the desired static pressure (e.g., due to the control of the pump using the static pressure transducer 201), then a response to the acoustic stimulus signal is detected using the at least one acoustic transducer (e.g., using microphone 223 of the probe 225) (block 422). Reflectance tympanometry data is then provided based at least on the response to the acoustic stimulus signal and the calibrated acoustic transfer function as, for example, described in U.S. Pat. No. 5,594,174 to Keefe and U.S. Pat. No. 5,651,371 to Keefe (block 424).

However, in certain situations, the pump 208 may be unable to maintain the desired static pressure in the ear canal. For example, if the probe 225 is not in a substantially leak-free state in the ear canal, the pump 208 may be unable to adjust the pressure sufficient to meet the desired static pressure in the ear canal. In such cases, the inability of the actual static pressure to meet the desired static pressure is detected (e.g., if the desired static pressure is not met upon a predetermined period of time) and the user is alerted (e.g., via an output of the system) that the pump is unable to maintain the desired pressure. For example, the alert may include any indicator to the user such as a visual cue, a sound alarm, etc.

Upon being alerted that the pump 208 is unable to maintain the desired pressure, the user may take one or more different actions. For example, as shown in block 428 of FIG. 5A, the user may desire to reinsert the probe 225 into the ear canal such that a substantially leak-free fit is achieved. Further, for example, the user may check one or more portions of the system in response to the alert.

Figure 5B:
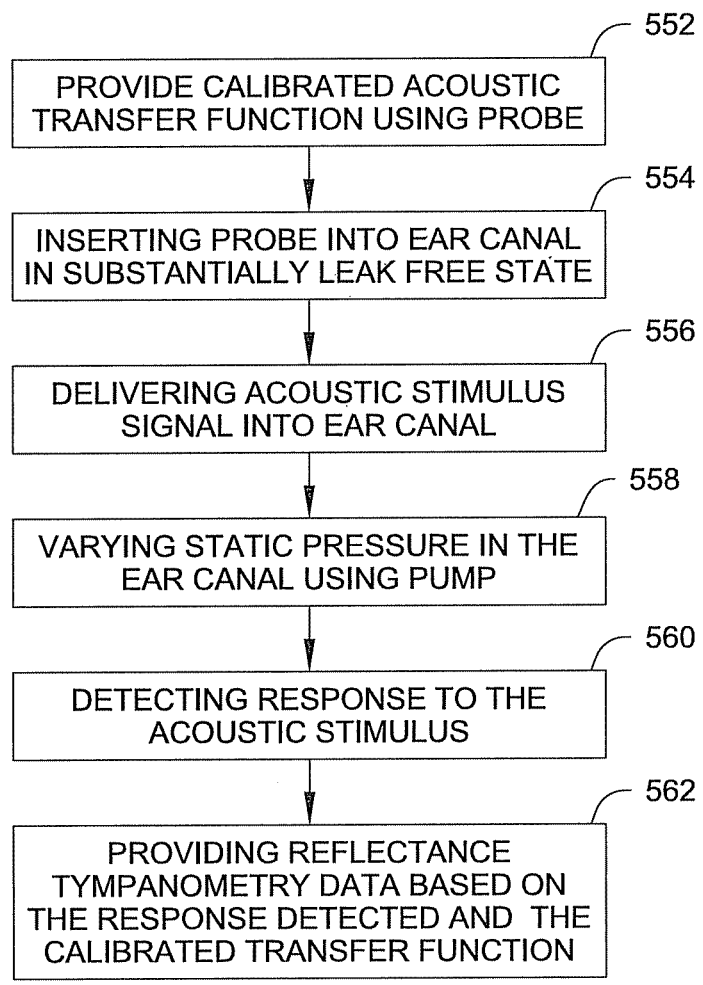
FIG. 5B and FIG. 5C show flow diagrams of another embodiment of a reflectance tympanometry test method and also an embodiment of an ambient pressure acoustic reflectance test method, respectively, that may be implemented using a test battery system such as that shown in FIG. 1, or that shown in FIG. 3 with one or more modifications.
Figure 5C:
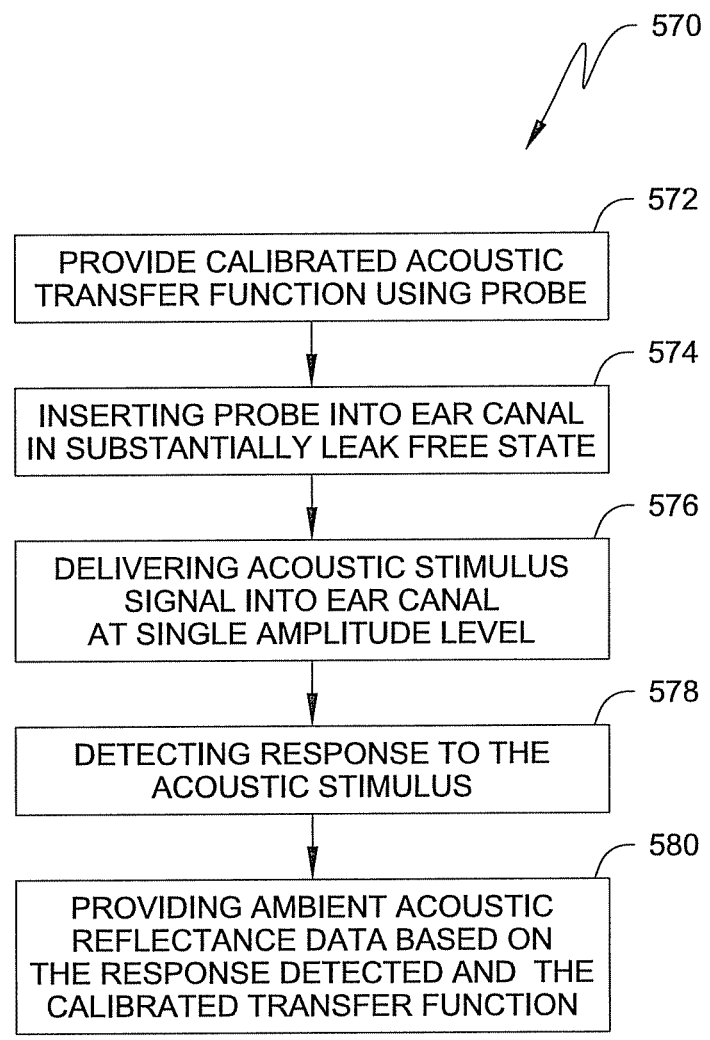

FIG. 5B and FIG. 5C show flow diagrams of another embodiment of a reflectance tympanometry test method 550 without feed back control and an embodiment of an ambient pressure acoustic reflectance test method 570, respectively, that may be implemented using a test battery system such as that shown in FIG. 1, or FIG. 3 with one or more modifications (e.g., removal of pump and feedback control).

As shown in FIG. 5B, performing the reflectance tympanometry test method 550 on a patient using the test system shown generally in FIG. 1 (or using components such as those of FIG. 3 without the feedback control) includes providing a calibrated acoustic transfer function using the probe 225 (block 552). As indicated previously, such calibration is described in U.S. Pat. No. 5,594,174 to Keefe and U.S. Pat. No. 5,651,371 to Keefe. The probe 225 is then inserted in the ear canal of the patient in a substantially leak-free state (block 554). An acoustic stimulus signal is delivered into the ear canal using the at least one acoustic transmitter (i.e., driver 254) of the probe 225 (block 556). Substantially simultaneously, the static pressure in the ear canal is varied using the pump 208 (block 558).

Assuming that the actual static pressure in the ear canal is equal to the desired static pressure, a response to the acoustic stimulus signal is detected using the at least one acoustic transducer (e.g., using microphone 223 of the probe 225) (block 560). Reflectance tympanometry data is then provided based at least on the response to the acoustic stimulus signal and the calibrated acoustic transfer function as, for example, described in U.S. Pat. No. 5,594,174 to Keefe and U.S. Pat. No. 5,651,371 to Keefe (block 562).

As shown in FIG. 5C, performing the ambient pressure reflectance test method 570 on a patient using the test system shown generally in FIG. 1 (e.g., using components such as those of FIG. 3 without the feedback control or the pump to vary static pressure) includes providing a calibrated acoustic transfer function using the probe 225 (block 572). As indicated previously, such calibration is described in U.S. Pat. No. 5,594,174 to Keefe and U.S. Pat. No. 5,651,371 to Keefe. The probe 225 is then inserted in the ear canal of the patient in a substantially leak-free state (block 574). An acoustic stimulus signal is delivered into the ear canal using the at least one acoustic transmitter (i.e., driver 254) of the probe 225 (block 576).

Reflectance measurements in the ear canal may be provided at ambient pressure in response to the use of a leak-free insertion of a probe assembly, in the frequency or time domain, over a range of two or more stimulus levels (i.e., otoreflectance). As used herein ambient pressure measurements, as opposed to tympanometry, refers to measurements taken at ambient pressure without the use of a pump adjusting the pressure in the ear canal in any manner.

However, as shown in FIG. 5C, the stimulus signal in the method 570 is at a single amplitude level. With use of a single level stimulus signal, there is the advantage of shorter test time, simpler instrumentation, simpler processing, and thus reduced overall cost, yet which is able to assess useful clinical information on middle-ear functioning.

Further, with reference to FIG. 5C, a response to the single level acoustic stimulus signal is detected using the at least one acoustic transducer (e.g., using microphone 223 of the probe 225) (block 578). Acoustic reflectance data is then provided based at least on the response to the single level acoustic stimulus signal and the calibrated acoustic transfer function as, for example, described in U.S. Pat. No. 5,594,174 to Keefe and U.S. Pat. No. 5,651,371 to Keefe (block 580).

As described herein, the battery of tests that may be implemented by the test battery system as shown generally in FIG. 1, or that shown in FIG. 3 with one or more modifications thereto, may include one or more various other auditory tests in addition to, or in the alternative to, an acoustic reflectance test. As such, various components (e.g., hardware and/or software) in addition to those described herein may be used to implement such tests in combination with an acoustic reflectance test or in combination with one or more other auditory tests.

For example, the system 200 of FIG. 3 (as well as the generalized system 10 of FIG. 1) further shows that an optional electrode configuration and interface 250 may be provided as a part thereof. Such an electrode configuration may be used to perform an ABR test.

For example, various embodiments of system components for performing ABR measurements have been described. For example, U.S. Pat. No. 6,974,421 to Causevic et al.; U.S. Pat. No. 5,601,091 to Dolphin; and U.S. Pat. No. 5,916,174 to Dolphin all describe ABR tests and components for carrying out such a test. In one embodiment, the system shown in FIG. 3 may be modified in view thereof to perform such tests.

Further, an ABR test may be performed using wideband stimuli such as a click or chirp, or more frequency-specific testing using a tone burst, in which the stimulus is gated on and off and contains a signal that is predominantly centered at a single frequency in the normal range of hearing. The ABR test may be used in form of a steady-state evoked potential (SSAEPs), which uses a signal with a carrier signal that is amplitude modulated (AM) by a modulation signal, such that carrier and modulation signals are typically sinusoids. The neural response is measured in the form of AM sidebands. As described in U.S. Pat. No. 6,602,202 to John et al., issued 5 Aug. 2003, entitled "System and Methods for Objective Evaluation of Hearing Using Auditory Steady-State Responses," a linear combination of multiple SSAEP stimulus sets can be used to obtain information on neural status simultaneously over a set of different frequencies in the normal range of hearing, which may provide a clinically useful hearing test. Similar components as described in such references may be incorporated into the test battery systems described herein for carrying out such ABR tests, and the ABR test includes the embodiment in which the form of the test is a SSAEP test.

Likewise, for example, the test battery system 10 generally shown in FIG. 1, or the system shown in FIG. 3 may be modified, for performing an admittance tympanometry test (e.g., a pump, software for output of an admittance tympanogram, etc.). Acoustic admittance tympanometry is distinct from the reflectance tympanometry test, if such a test is included in the test battery system. Admittance tympanometry may include single-frequency or multi-frequency testing using single-component or double-component admittance.

The single-component admittance tympanogram typically uses the acoustic admittance magnitude, and the double-component admittance tympanogram typically uses the real and imaginary parts of the acoustic admittance, or the magnitude and phase of the acoustic admittance.

The conventional acoustic admittance tympanogram test typically includes a compensation procedure to account for the influence of the ear canal volume of air contained between the probe tip sealed in the ear canal and the eardrum (i.e., the tympanic membrane). Such a compensation procedure is typically accurate only at low frequencies, while calibration procedures may be inaccurate for frequencies as low as 0.8 kHz and at higher frequencies. Acoustic reflectance tympanometry is not required to have such a compensation procedure. In a test battery with the acoustic reflectance test, the acoustic admittance tympanogram test may also include such well-known measurements as peak compliance, tympanometric peak pressure, tympanometric gradient and tympanometric width. It is understood by those skilled in the art that a system to measure acoustic admittance is also a system to measure acoustic impedance, because the acoustic impedance is simply the inverse on the complex plane of the acoustic admittance.

Various embodiments of systems for performing admittance tympanometry have been described in, for example, James W. Hall III and David Chandler, "Tympanometry in Clinical Audiology, Chapter 20, Handbook of Clinical Audiology, Fourth Edition, Jack Katz, Editor (1994) (Williams & Wilkins, Baltimore) which also discuss the use of clinical tympanometry tests by audiologists. In one embodiment, the system shown in FIG. 3 may be modified in view thereof to perform such admittance tympanometry.

Figure 8:
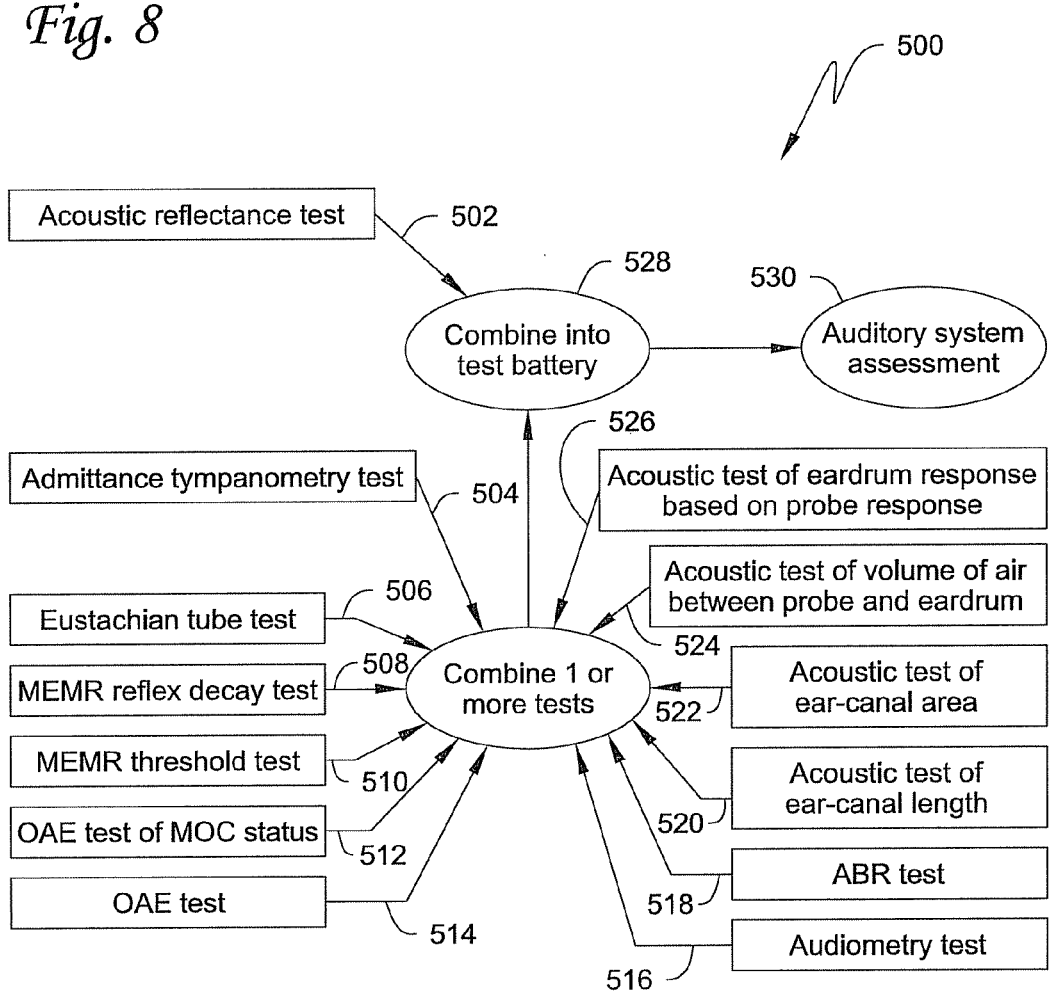
FIG. 8 is a flow diagram showing one embodiment of a test battery method including the use of an acoustic reflectance test that may be implemented using the test battery system shown in FIG. 1, or that shown in FIG. 3 with one or more modifications.

Further, for example, the test battery system 10 generally shown in FIG. 1 further includes other components for performing one or more of the other auditory tests such as those shown in FIG. 8 including, but clearly not limited to: an Eustachian tube test, a middle-ear muscle reflex (MEMR) threshold test, a MEMR reflex decay test, an otoacoustic emission test of medial olivocochlear status, an otoacoustic emission test, an acoustic test of eardrum response based on probe response, an acoustic test of volume of air between the probe and eardrum, an acoustic test of ear canal cross-sectional area at two or more locations along an axis of the ear canal, an acoustic test of ear canal length, an auditory brain stem response test, and an audiometry test.

As discussed herein, acoustic-reflex testing in the form of a shift in acoustic immittance has been a well known part of an acoustic immittance test battery for decades and may be used as one of the tests of a battery of tests described herein. However, at least in one or more embodiments, the other types of acoustic-reflex testing, which do not rely on acoustic immittance tests as practiced within the scope of ANSI S3.39-1987 and related audiological publications, are used so as to provide the advantages of the results from such non-immittance reflex tests. As previously discussed, these non-immittance types of MEMR tests fall into two classes based on a shift in a response in the presence of a MEMR activator signal: (1) a MEMR test based on a shift in sound pressure, which may be any shift in the magnitude and/or phase response in the frequency domain or in the waveform of a time-domain response, and (2) a MEMR test based on a shift in a wideband acoustic reflectance response (or in related acoustic absorbed power, transmittance or acoustic intensity responses). Further discussion of various reflex testing is provided herein.

MEMR responses are typically measured using ipsilateral and contralateral procedures. In ipsilateral procedures, for example, a response shift in acoustic admittance is conventionally measured at a single probe frequency in which an activator signal of varying level is introduced in the same ear that the acoustic admittance response shift is measured. The activator signal is intended to elicit the MEMR.

In contralateral procedures, for example, a response in acoustic admittance is conventionally measured at a single probe frequency in which the activator signal of varying level is introduced in the opposite ear. Instead of a response shift in acoustic admittance at a single probe frequency, a MEMR response shift in the acoustic reflectance can be measured over a broad range of probe frequencies, which may thus provide the ability to detect a MEMR shift at lower activator levels, and this leads to a lower MEMR threshold.

The ipsilateral MEMR response can be measured using, for example, the system illustrated in FIG. 3, with the use of the second driver (Driver2) for presenting the activator signal into the same ear as the other stimulus signal. The contralateral MEMR response can be measured, for example, with the same system as shown in FIG. 3, and with system components (e.g., an additional probe (not shown) including at least an acoustic transmitter to insert into the second ear during the MEMR threshold test) that deliver the activator signal at varying levels in the contralateral ear, which may include the use of Driver2 for presenting the activator signal into the opposite ear to that in which the stimulus signal is presented. In one embodiment for contralateral MEMR measurements, the signal processor 210 controls data acquisition and processing in both ears. A bilateral MEMR response can alternatively be measured using a MEMR activator signal that is delivered both ipsilaterally and contralaterally using an additional Driver3 (not shown).

In another embodiment, MEMR measurements may be performed by measuring shift in a wideband acoustic admittance in response to an acoustic stimulus signal with no other sound presented and in the presence of an ipsilateral or contralateral sound.

In yet a further embodiment, performing a MEMR threshold test using the system may include performing a comparison test in which the at least one acoustic transmitter delivers two or more acoustic stimulus signals into the ear canal, such that the later onset of the two or more stimulus signals is delayed at least on the order of the middle-ear muscle reflex latency. At least one of the earlier of the two or more acoustic stimulus signals is a MEMR activator signal, which is intended to elicit a MEMR. The MEMR activator signal may be presented in the same ear as the other acoustic stimulus signals in the case of an ipsilateral MEMR test, or may be presented in the opposite ear as the other acoustic stimulus signals in the case of a contralateral MEMR test, or may be presented in both ears in the case of a bilateral MEMR test.

An optional refinement of this embodiment performs a comparison test in which at least three acoustic signals are delivered at three different onset times, such that the first, which is the earliest onset, and third, which is the latest onset, of these acoustic signals are the same and such that the first and third acoustic signals are presented in the same ear. The second acoustic signal, which is the MEMR activator, has sufficiently long duration and sufficiently high level to elicit a MEMR in a normal-functioning ear. Activation of the MEMR by the second signal influences the acoustic response to the third signal. A comparison of the acoustic responses of the first and third signals is used to detect whether a MEMR is present or absent. In this optional refinement of the embodiment, the MEMR activator may be presented ipsilaterally, contralaterally or bilaterally, although in the ipsilateral and bilateral tests the preferred embodiment is that the first signal ends before the second signal begins, and the second signal ends before the third signal begins.

The MEMR threshold test for the case of two identical acoustic stimulus signals is described in Neumann et al. (1996), "Detection of the acoustic reflex below 80 dB HL," *Audiol. Neuro-Otol.* 1, pp. 359-369; and Muller-Wehlau et al. (2005) "The effects of neural synchronization and peripheral compression on the acoustic-reflex threshold," *J. Acoust. Soc. Am.* 117, pp. 3016-1037.

One embodiment of such a comparison process, is described with reference to a double-evoked system that has been used to measure an OAE response evoked from the cochlea (e.g., see U.S. Pat. No. 5,792,073 to Keefe issued 11 Aug. 1998 and entitled "System and method for acoustic response measurement in the ear canal"; and U.S. Pat. No. 5,885,225 to Keefe issued 23 Aug. 1999 and entitled "System and method for the measurement of evoked otoacoustic emissions"). By modifying the stimulus parameters, a double-evoked system can be used to measure a MEMR evoked by the middle-ear without evoking a detectable cochlear response indicative of an OAE response by using a similar set of stimulus conditions to those used in a double-evoked system and by combining the responses from each stimulus such that the linear stimulus response cancels from the resultant and a nonlinear response remains, which is the MEMR response.

Of the two stimulus signals used in the double-evoked method, one embodiment uses a first stimulus signal as a low- or moderate-level probe signal with signal energy present below 500 Hz, such that this frequency is selected below the frequency range in which OAEs are typically measured. The second stimulus signal is a higher-level signal to activate the middle-ear muscle reflex. The two stimuli are presented each alone, and then jointly together, and a corresponding set of three responses is obtained. A nonlinear residual is defined as the difference between the sum of the responses to the first stimulus-alone and second stimulus-alone conditions and the response to the joint presentation condition. The resulting nonlinear residual from the double-evoked technique is indicative of a MEMR with a latency in the range of approximately 50-150 ms indicative of such a reflex. A shorter latency of approximately 20 ms or less would indicate that the nonlinear residual includes an OAE contribution and thus can be classified on the basis of latency with respect to a MEMR contribution. The preferred embodiment measures the double-evoked set of three responses to the two stimuli presented both individually and simultaneously in the same test ear, while a MEMR activator signal is gated on and off. The nonlinear residuals in the presence and absence of the MEMR activator signal may be compared to detect the presence of a MEMR, with either ipsilateral, contralateral or bilateral presentations of the MEMR activator.

Systems for performing MEMR threshold tests are also described by Jerry L. Northern and Sandra A. Gabbard ("Tympanometry in Clinical Audiology, Chapter 21, in Handbook of Clinical Audiology, Fourth Edition, Jack Katz, Editor, 1994 (Williams & Wilkins, Baltimore)) discuss the use of clinical tympanometry tests by audiologists.

In one or more embodiments, the system shown in FIG. 3 may be modified in view of the above described MEMR processes to perform such tests.

Further, for example, a MEMR decay test may be carried out based at least in part on a threshold that has been determined in the MEMR threshold test. As described in Northern and Gabbard (1994), the MEMR decay test may be performed by presenting the MEMR activator 10 dB above its MEMR threshold for approximately 10 seconds. The time course of the magnitude of the MEMR shift induced by that activator is assessed over an approximately 10-second interval in one embodiment and the reflex decay is determined by whether the MEMR shift decreased by more than one-half of its initial magnitude. The time-course of the MEMR magnitude over time may be indicative of an eighth nerve lesion or provide information relevant to the detection of otosclerosis. The activator is typically a tone at 500 or 1000 Hz.

A MEMR test that measures the MEMR shift as a function of frequency in a single measurement using a wideband pressure response, or wideband acoustic transfer function such as acoustic admittance or acoustic reflectance, may improve the clinical performance of the MEMR decay test by providing additional frequency-specific information. In such a wideband MEMR decay test, the preferred embodiment uses an activator tone at 500 or 1000 Hz at a level 10 dB above its MEMR threshold. Some MEMR testing can cause a permanent sensorineural hearing loss and tinnitus due to the use of excessively high MEMR activator levels, particularly in the MEMR decay test in which the activator is increased by 10 dB above its threshold value for a 10-second duration (Hunter L L, Ries D T, Schlauch R S, Levine S C, Ward W D (1999), Safety and clinical performance of acoustic reflex tests, *Ear and Hearing* 20, 506-514.). The increased activator level for a longer duration in the MEMR decay than the threshold test increases the safety concerns in the MEMR decay test. Thus, a more sensitive MEMR threshold test leading to a lower MEMR threshold would also have an associated more sensitive MEMR decay test that would use an activator at a lower level, thus improving test safety. This invention describes several classes of more sensitive MEMR threshold tests that would be useful in performing safer MEMR decay tests, e.g., with reduced likelihood that the MEMR decay test will itself produce hearing loss. In one embodiment, the system shown in FIG. 3 may be modified in view thereof to perform such tests.

Otoacoustic emission (OAE) response tests include, among others, distortion product otoacoustic emission (DPOAE) tests, click-evoked otoacoustic emission (CEOAE) tests, transient evoked otoacoustic emission tests (TEOAE) which include chirp-evoked OAEs, and stimulus frequency otoacoustic emission (SFOAE) tests. Various embodiments of systems for performing such otoacoustic emission tests have been described in, for example, U.S. Pat. No. 6,974,421 to Causevic et al.; U.S. Pat. No. 5,601,091 to Dolphin; U.S. Pat. No. 5,916,174 to Dolphin; and U.S. Pat. No. 5,738,633 to Christiansen, issued 14 Apr. 1998, entitled "Oto-Acoustic Emission Analyser," which describes a hand-held OAE analyzer that includes a static pump for use in tympanometric measurements. In one embodiment, the system shown in FIG. 3 may be modified in view thereof to perform such tests.

Typical embodiments of the present invention use either the DPOAE or CEOAE in the otoacoustic emission test or otoacoustic emission test of medial olivocochlear status test, because these are the most widely used and understood OAE responses. However, the SFOAE response may be advantageous for testing at frequencies at and below 1000 Hz.

Further, for example, various embodiments of system components for performing an otoacoustic emission test of medial olivocochlear (OAE test of MOC) status have been described using CEOAEs in Ryan S and Piron J P (1994), "Functional maturation of the medial efferent olivocochlear system in human neonates," *Acta Otolaryngol.* 1994 September; 114 (5):485-489 and using DPOAEs in Moulin A, Collet L and Duclaux R (1993), "Contralateral auditory stimulation alters acoustic distortion products in humans," *Hearing Research*

65, 193-210. In one embodiment, the system shown in FIG. 3 may be modified in view thereof to perform such tests.

In one embodiment, the OAE test of MOC status uses a wideband noise signal as the ipsilateral activator in such a test so that the test is performed in a single test ear. Further, the test uses the shift induced by the MOC function on a SFOAE response as the indicator of MOC function. In an alternate embodiment, the test uses a shift in a DPOAE response or in some other OAE response as the indicator of MOC function.

In various embodiments of the test battery system 10, the system 10 is operable for performing ear canal measurements such as the acoustic test of volume of air between the probe and eardrum, the acoustic test of ear canal cross-sectional area at two or more locations along an axis of the ear canal, or the acoustic test of ear canal length. These can be used with the measured pressure at the microphone inlet of the probe or with acoustic transfer functions at the probe tip to assess the sound pressure level and phase, and acoustic transfer functions, at the eardrum.

One embodiment of the acoustic test to determine the volume of enclosed air uses a single-frequency (e.g., 226 Hz) admittance tympanogram with a conventional compensation procedure that provides ear canal volume. With a conventional single-peaked tympanogram at 226 Hz, the ear-canal volume is assessed in terms of the difference in the admittance magnitude or compliance at the static pressure of the tympanometric peak relative to the maximal or minimal static pressure in the measurement range, which corresponds to a static pressure distant from that of the peak.

One embodiment of the acoustic test to determine the length of the ear canal between the probe tip and ear drum uses the slope of the phase of the acoustic reflectance response at ambient pressure calculated between approximately 5.5 kHz and 8 kHz, because the tympanic membrane has only a slight total volume-velocity motion in this frequency range, although it does also have complex local motions across its surface. The fact that the tympanic membrane is effectively rigid in this frequency range simplifies the plane-wave reflection characteristics so that the reflectance phase measured at the probe tip is dominated by the length between the probe tip and tympanic membrane. The plane-wave acoustic propagation in the ear canal between the probe and tympanic membrane can be modeled by assuming that the ear-canal area varies slowly with respect to the acoustic wavelength. A hierarchy of mathematical models of increasing complexity can be devised, with a cylindrical ear-canal geometry (of constant cross-sectional area between probe and eardrum) being the simplest, a truncated cone geometry being the next simplest, and a model based on estimating the cross-sectional area of the ear canal at various locations between the probe and the eardrum as being the most complex.

Based on any of these models, the acoustic reflectance and pressure at the eardrum, which are associated with the plane-wave mode of acoustic propagation, can be calculated in terms of the acoustic reflectance and pressure at the probe tip and in terms of the model parameters relating the area and distance between the probe and eardrum. Given the acoustic reflectance at the eardrum, it is possible to calculate other acoustic transfer functions at the eardrum such as acoustic admittance.

Those skilled in the art will appreciate that idealizing the tympanic membrane to be located at a single point in the ear canal is but a useful approximation, because the tympanic membrane is an extended surface in three dimensions, which is characterized by local variations in displacement in response to a sound stimulus at high frequencies. Nevertheless, such an idealization may be clinically useful in obtaining high-frequency measures of middle-ear functioning at the eardrum as opposed to measurements at the probe. One will recognize that alterations of this frequency range are possible.

Alternate embodiments of acoustic tests to determine the length of the ear canal have been described, for example, in Joseph C. K. Chan and C. Daniel Geisler (1990) ("Estimation of eardrum acoustic pressure and of ear canal length from remote points in the canal," *J. Acoust. Soc. Am.* 87, 1237-1247), in which the probe microphone must be positioned in two or more locations in the ear canal, and acoustic response information is used in the frequency range above 4 kHz. In one embodiment, the system shown in FIG. 3 may be modified in view thereof to perform such length determination tests.

One embodiment of the acoustic test of ear canal cross-sectional area at one or more locations along the axis of the ear canal may include an acoustic measurement of the cross-sectional area at the probe tip (e.g., such a measurement may be useful in converting admittance measurements to reflectance measurements). Further, such an acoustic test of cross-sectional area may also include a more complete measurement of the cross-sectional area at more than one location between the probe tip and eardrum (e.g., such a measurement may be useful in assessing the high frequency effects of variations in ear-canal cross-sectional area on the accuracy of the acoustic test of eardrum response based on probe response). In other words, when measurements of cross-sectional area at two or more locations along the axis of the ear canal are performed, they may include cross-sectional area at the probe tip and one or more locations between the probe tip and eardrum, or may include cross-sectional area at one or more locations between the probe tip and eardrum. In any case, variability along the axis of the ear canal can be determined based on such measurements.

One embodiment describing the measurement of cross-sectional area in the ear canal is described in Michael R. Stinson and S. M. Khanna (1989) ("Sound propagation in the ear canal and coupling to the eardrum, with measurements on model systems," *J. Acoust. Soc. Am.* 85, 2481-2491), but this method depends on detailed measurements in a reproduction of an ear canal and is not intended for use in clinical measurements.

Another embodiment describing the acoustic measurement of the cross-sectional area in the ear canal at the probe tip is described in Douglas H. Keefe, Robert Ling, and Jay C. Bulen (1992) ("Method to measure acoustic impedance and reflection coefficient," *J. Acoust. Soc. Am.* 91, 470-485). However, this embodiment does not describe how to measure the cross-sectional area elsewhere in the ear canal.

An alternate embodiment to measure the cross-sectional area in an acoustic waveguide is described in Jerry A. Ware and Keith Aki (1968) ("Continuous and discrete inverse-scattering problems in a stratified elastic medium. I. Plane waves at normal incidence," *J. Acoust. Soc. Am.* 45, pp. 911-921), which is appropriate for use in measuring the area-distance function in an ear canal between probe and eardrum. Due to the short ear-canal length between the probe and the eardrum, when measured relative to the transverse cross-sectional diameter, the effect on the area-distance algorithm of viscothermal damping at the ear-canal walls can be neglected in acoustically measuring the area function. Other area-distance function tests have been reported in the literature for measurements of cross-sectional area in an acoustic waveguide. In one embodiment, the system shown in FIG. 3 may be modified in view thereof to perform such cross-sectional area measurement tests. The preferred embodiment is to calculate the ear-canal cross-sectional area using the techniques of Keefe et al. (1992), Huang et al. (2000), and Ware and Aki (1968).

Yet further, audiometry tests used in a test battery, for example, may include air conduction audiometry and bone conduction audiometry. Such audiometry tests have been described in Phillip A. Yantis, "Puretone air-conduction threshold testing," Chapter 7, Handbook of Clinical Audiology, Fourth Edition, Jack Katz, Editor, 1994 (Williams & Wilkins, Baltimore), and in Donald D. Dirks, "Bone-conduction threshold testing," Chapter 9, Handbook of Clinical Audiology, Fourth Edition, Jack Katz, Editor, 1994 (Williams & Wilkins, Baltimore). In one embodiment, the system shown in FIG. 3 may be modified in view thereof to perform such tests by presenting tones of calibrated level using one of the sound sources.

Further, for example, in an embodiment of the invention that includes an audiometry test, tones are presented to the patient's ear and the patient responds whether or not each tone is audible. The audiometry test may be performed by an audiologist or other tester. The patient can respond concerning audibility using a gesture to the tester, which may include any visual or auditory cue communicated from the patient to the tester, or using a response device, which is a component of the audiometer (e.g., as part of the system that performs one or more other auditory tests as described herein). Such a response device collects information from the patient on whether each tone was audible or not. The audiometry test may be performed in an automatic mode, without the need for intervention during the test by the tester, in which case a response device is part of the audiometer and the audibility information contained in the sequence of patient responses via the response device may be used in the procedures of the audiometry test.

Figure 7A:
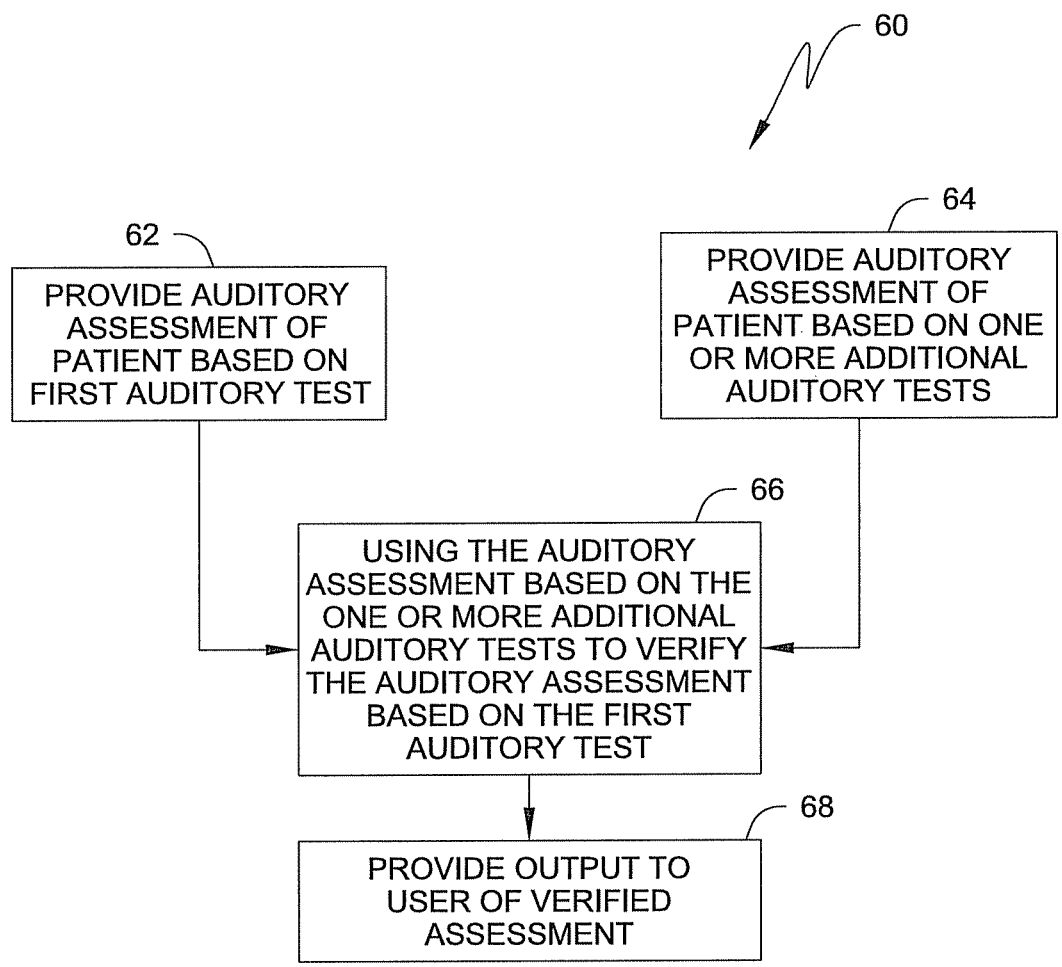
FIGS. 7A and 7B show flow diagrams of one or more analysis and output methods that may be used in the generalized test battery method shown in FIG. 6 according to the present invention.
Figure 7B:
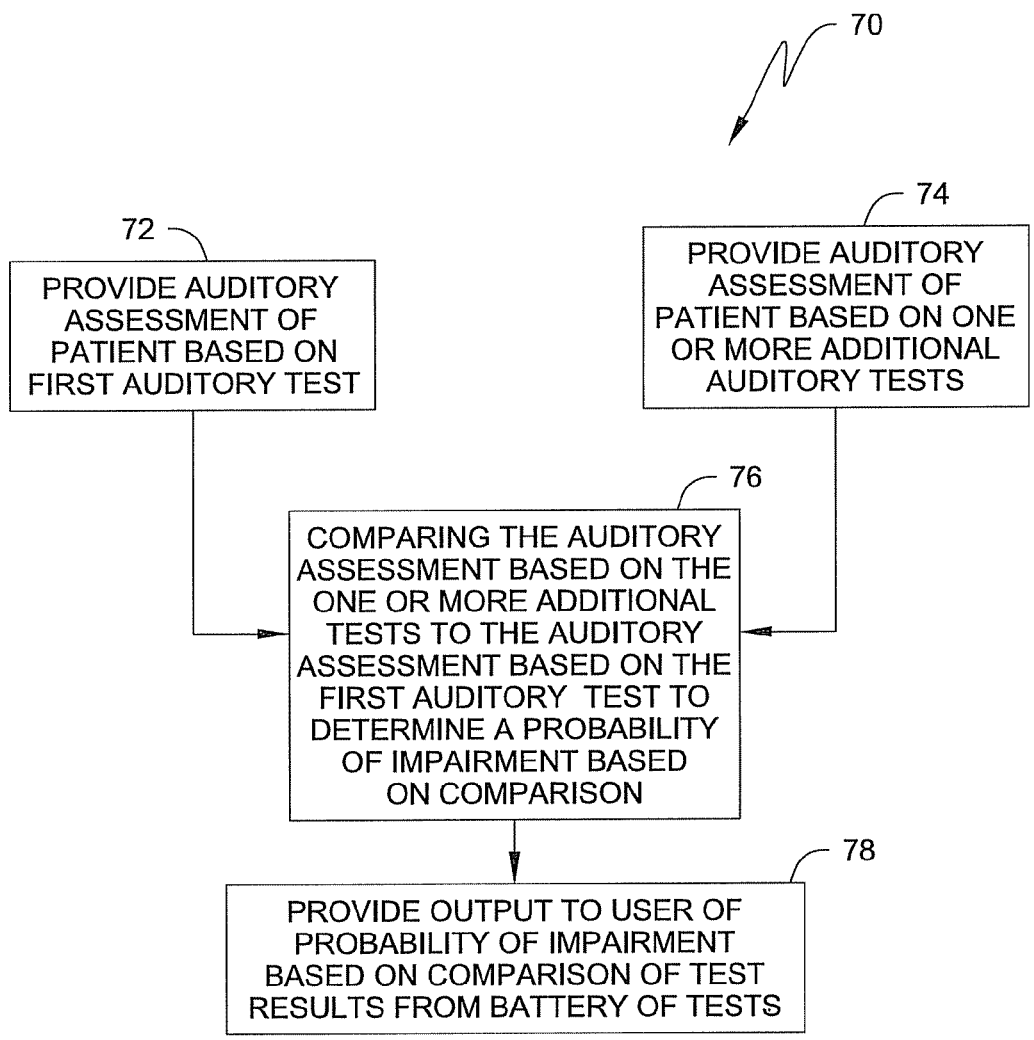

As previously described with reference to FIG. 6, the test battery method according to the present invention includes performing a first auditory test using a test system, such as the battery test system 10 (block 52), performing one or more additional auditory tests using the battery test system 10 or one or more additional test apparatus (block 54), and providing the results of such tests to the user (block 56). In one or more embodiments, as shown in FIGS. 7A and 7B, the use of such results may vary depending on the type of auditory tests which are performed by the system 10. In other words, test results of multiple tests are provided for analysis. Such test results may be provided by separate and individual test instruments (e.g., test system 10 and one or more other test apparatus 17) that perform one or more tests, or may be provided by a single test apparatus (e.g., test system 10). Further, for example, one of the instruments may perform the analysis on the test results to provide an output based on a combination of the test results from one or more test apparatus, or the analysis and output may be provided by another system or apparatus provided with the test results.

FIG. 7A shows a flow diagram of one embodiment of an analysis and output method 60 that may be implemented according to the present invention. For example, an auditory assessment of a patient based on a first auditory test may be provided (block 62) along with an auditory assessment of a patient based on one or more additional auditory tests carried out with the same system 10 (block 64). The results of one or more of the tests may be used to verify the results and/or the auditory assessment based on the results of the one or more other auditory tests (block 66). Thereafter, an output may be provided to a user with reference to the verification or validation of the assessment (block 68).

For example, as discuss further herein, MEMR tests and ABR tests are each sensitive to the presence of auditory neuropathy. If such tests are performed in the same battery of tests by the same system, then, for example, an assessment of the presence of auditory neuropathy could be made for the patient using the MEMR test, and verified using an assessment based on the ABR test. An output to the user may be present that indicates the verification or validation of the presence of auditory neuropathy.

FIG. 7B shows a flow diagram of another embodiment of an analysis and output method 70 that may be implemented according to the present invention. For example, an auditory assessment of a patient based on a first auditory test may be provided (block 72) along with an auditory assessment of a patient based on one or more additional auditory tests (block 74). The results and/or auditory assessment based on such results of one or more of the tests may be compared to the results and/or the auditory assessment based on the results of the one or more other auditory tests (block 76). An output may be provided to a user of a probability of impairment based on the comparison of results from the battery of tests performed (block 78). For example, various weighting factors may be attached to certain test results for use in the determination of a final probability output by the test battery for one or more instances of middle-ear, cochlear, neural or behavioral dysfunction.

Examples of using results of tests performed by different test devices, were described in Keefe D H, Zhao F, Neely S T, Gorga M P & Vohr B R (2003) ("Ear-canal acoustic admittance and reflectance effects in human neonates. I: Predictions of otoacoustic emission and auditory brainstem responses," *J. Acoust. Soc. Am.* 113, 389-406) and in Keefe D H, Gorga M P, Neely S T, Zhao F & Vohr B R (2003) ("Ear-canal acoustic admittance and reflectance measurements in human neonates: II: Predictions of middle-ear dysfunction and sensorineural hearing loss," *J. Acoust. Soc. Am.* 113, 407-444). For example, a test battery of an ambient-pressure acoustic reflectance test, ambient-pressure acoustic admittance test, OAE test and ABR test was used for joint predictions of cochlear hearing loss and middle-ear dysfunction in a group of newborn infants, and a test battery was used for interpreting whether infants, who had been incorrectly identified as having a permanent hearing loss by the OAE/ABR tests, had middle-ear dysfunction as inferred by the acoustic reflectance and admittance tests. However, as indicated, such tests were performed using different test devices with the results later analyzed, in some cases, years after the human-subject data were acquired. It will be appreciated that a single test device as described herein, which may include a handheld device, will be useful in clinical tests of newborns, children and adults. Such assessments using a single test device suitable for carrying out the desired test battery will allow clinical tests to be performed and provide output for immediate use to a clinician. Other applications of the use of combining probabilities of various dysfunctions from a test battery of multiple tests has similar promise in improving the overall assessment of the patient's auditory system and hearing.

In one embodiment, the test battery is used on populations of normal-hearing individuals and on populations of individuals with a specific dysfunction or combination of dysfunctions. Using multivariate signal detection theory, the optimal weighting of test battery outputs is calculated on these populations that best separates the normal-hearing group from the group with the particular dysfunction. These weighting factors are included in the test battery device. The probability can be calculated using these weighting factors with the test battery outputs measured on a newly tested patient, so that the risk that the patient has this particular dysfunction of combination of dysfunctions can be output by the test battery device. This process can be repeated on populations with other known auditory dysfunction or hearing loss, so that multiple sets of weighting factors specific to each dysfunction and hearing-loss category can be compiled into a single database. Given a particular test battery performed on a patient, the probabilities associated with each of several auditory dysfunctions and types of hearing loss can be output by the test battery device. Following Keefe and Simmons (2003), the ambient-pressure acoustic reflectance and reflectance tympanometry test outputs can be transformed using a moment analysis of the energy transmittance derived from the energy reflectance, which reduces the number of variables, particularly for the reflectance tympanometry test that varies with both frequency and static pressure. The use of such a reduced set of moment variables simplifies the multivariate decision theory. The test battery device according to the present invention is simplified, as compared to any previous analysis method performed, in that it directly encodes the weighting of test battery outputs to form each predictor of dysfunction or hearing loss (e.g., probability of such dysfunction or impairment).

For example, as discussed further herein, an acoustic reflectance test used with an ABR test, and a MEMR test could be used to screen and diagnose patients for middle-ear dysfunction, sensorineural dysfunction, and auditory neuropathy. Some tests in the test battery are particularly sensitive to particular dysfunctions, and the use of a battery of multiple test responses allows evaluation of the likelihood of each particular dysfunction based on the most sensitive test or tests for that dysfunction, and the likelihood across multiple tests of one or more dysfunctions. The results of such tests could be compared to give a probability that a patient had any one of such impairments. An output to the user may be presented that shows such a probability (e.g., with or without showing the actual results of each test).

One will recognize that the results of the battery of tests may be used for other purposes or to provide other outputs as well. For example, as further described herein with reference to FIGS. 10A and 10B, such results of the test battery may be used to fit hearing aids (e.g., make adjustments to parameters of the hearing aid to modify functionality thereof).

One or more combinations of tests to assess the functional status of the auditory system are described herein. In one embodiment, the test battery includes a test of the status of the external and middle-ears, and may also include one or more additional tests of the status of the external and middle-ears, tests of the status of the cochlea, the auditory nerve, and the specific brain regions serving auditory perception, and audiometry, which is a behavioral test of hearing with a test result known as an audiogram. The test of the status of the external and middle-ears may be the test of the acoustic reflectance of the ear, which can be performed as an ambient pressure acoustic reflectance test or as a reflectance tympanometry test.

Use of Acoustic Reflectance Test in the Test Battery

FIG. 8 shows one or more embodiments of a test battery method 500 that combines (circle 528) the results of an acoustic reflectance test 502 with the results of one or more other auditory tests for use in auditory system assessment (circle 530) of patient.

The measurement of the acoustic reflectance in the human ear canal conveys clinically important information relevant to screening and diagnosis of middle-ear dysfunction. For example, when results of an acoustic reflectance test is combined with MEMR response measurements that use an activator tone to elicit the MEMR shift in acoustic reflectance or in sound pressure, further clinically important information is obtained on middle-ear and efferent neural pathways in the auditory system. The absence of a MEMR response is indicative of the presence of auditory neuropathy, and a device with an acoustic reflectance test and a MEMR threshold test has potential for early identification of auditory neuropathy, particularly in newborn infants. MEMR responses may be measured at a static pressure in the ear canal that may differ from ambient atmospheric pressure. When a MEMR shift is measured in acoustic reflectance, the addition of the feedback system to maintain the intended static pressure increases the reliability and accuracy of threshold and supra-threshold MEMR response measurements. The further inclusion of an OAE test in such a device provides a test battery of acoustic reflectance for middle-ear dysfunction, MEMR threshold for neural efferent system, and OAEs for cochlear dysfunction in outer-hair cell functioning. The output from such a test battery of responses may include the separate probabilities of middle-ear dysfunction, cochlear dysfunction and neural dysfunction.

For this and other outputs of probabilities, it can be appreciated that the device may provide a few categories of increasing probability for a given dysfunction. For example, a two-category output may include a green and red light in a visual output to indicate normal functioning or a relatively high probability of the dysfunction. A three-category output may include green, yellow and red lights to indicate probability classes corresponding to test results of normal functioning, possible dysfunction, and probable dysfunction. More than three categories may also be used and the test output may be presented in some other visual manner, through an audible alarm or stored as test results for later analysis. In other words, any indication of the probability of an impairment may be output (e.g., by a numerical or ordinal scale, three category probability categories, etc.) to represent distinct probabilities from low to high values.

As shown in FIG. 8, the test battery method 500 includes an acoustic reflectance test 502 for use in generating an objective assessment of the auditory system function (e.g., the acoustic reflectance test being a test of the status of the external and middle-ears). Further, as shown, the test battery also uses one or more test results from a combination of one or more auditory tests. This combination of one or more tests includes one or more of the following tests: an acoustic admittance tympanometry test 504, a tympanometric test of Eustachian tube dysfunction 506, a test of the acoustic MEMR threshold 510, a supra-threshold MEMR test of reflex decay 508, an OAE test 514, an OAF test of MOC status 512, an acoustic test of eardrum response based on probe response 526 (e.g., such eardrum response including one or more of the acoustic reflectance at the eardrum, the acoustic admittance at the eardrum, and the sound pressure level at the eardrum), an acoustic test of volume of air between probe and eardrum 524, an acoustic test of ear-canal area 522, and an acoustic test of ear-canal length 520, an ABR test 518, and an audiometry test 516.

If the audiometry test 516 is not included in the test battery method 500, then the test battery system generates an objective assessment of the peripheral auditory system. If the audiometry test 516 is included in the test battery method 500, then the test battery system generates an objective assessment of the peripheral auditory system and an assessment of the behavioral threshold of hearing.

As described herein, the acoustic admittance tympanometry test 504 (e.g., resulting in an admittance tympanogram or data representative thereof) is distinct from a reflectance tympanometry test, if such a test is included in the test battery. The combination of the results of an acoustic reflectance test 502 and conventional acoustic admittance tympanogram 504 provide more information on the status of the external and middle-ear than either test provides by itself. This is of particular relevance when the acoustic reflectance of the ear test 502 is an ambient pressure reflectance test.

In one or more embodiments, when analyzed together, the results of a test battery including an acoustic reflectance test 502 and conventional acoustic admittance tympanometry 504 may show the likelihood of various types of middle-ear dysfunctions such as otitis media with effusion, tympanic membrane perforation, ossicular disarticulation, otosclerosis, collapsed ear canal, excessively positive or negative middle-ear cavity pressure. Outputs that may result from such a combination of tests may include, for example, whether any middle-ear dysfunction is likely present, and, if so, which dysfunction or dysfunctions are most likely present. The relationship between the test outputs and the probability of one or more impairments would in this and other applications be constructed based on test battery results measured in a normal-functioning population and in a population of patients with each particular dysfunction.

Pattern classification techniques may be used with the data to find optimum predictors from the test battery outputs of a particular dysfunction. This approach has, for example, been described in the pair of Keefe et al. (2003) publications cited earlier on a test battery of acoustic reflectance, acoustic admittance, OAE and ABR tests in newborns, and in Keefe and Simmons (2003) ("Energy transmittance predicts conductive hearing loss in older children and adults," *J. Acoust. Soc. Am.* 114, 3217-3238) to predict conductive hearing loss in older children and adults based upon ambient-pressure and pressurized acoustic transfer function measurements (e.g., reflectance and admittance).

For example, in one embodiment, a battery of tests that combines an acoustic reflectance test and a low-frequency (e.g., about 226 Hz) acoustic admittance tympanometry test can be used by outputting the probability of a patient having Eustachian tube dysfunction. The probability can be provided to the user of the test battery system in terms of a yes-no type of output.

Further, as described herein, the results of an acoustic reflectance test 502 and an MEMR threshold test 510 may be combined to provide an auditory assessment of a patient. In one or more embodiments, when analyzed together, the results of a test battery including an acoustic reflectance test 502 and an MEMR threshold test 510 may show the individual probabilities of middle-ear dysfunction or an auditory neuropathy. For example, an output that may result from such a combination of tests in the form of a simple yes-no classification (e.g., red light-green light) that the ear: is normal functioning (normal middle ear functioning and no auditory neuropathy), has risk for middle-ear dysfunction but no auditory neuropathy, has normal middle-ear function but risk for auditory neuropathy, or has risk for both middle-ear dysfunction and auditory neuropathy.

In one embodiment, a test battery combining an acoustic reflectance test 502 and a MEMR threshold test 510 (or supra-threshold MEMR reflex decay test 508 carried out after a threshold is determined) uses an acoustic reflectance test 502 with a MEMR threshold or shift test 510 based on a wideband shift in the acoustic reflectance response in the presence of an ipsilateral or contralateral sound. An assessment that may be output to a user based on this test battery includes, for example, screening information of the risks for middle-ear dysfunction and auditory neuropathy and diagnostic information from the MEMR decay and other tests.

In an alternate embodiment, an acoustic reflectance test 502 (e.g., either ambient pressure or tympanometric) is used with a conventional MEMR test 510 that measures the shift in the acoustic admittance of a single-frequency probe tone (e.g., a tone at 226 Hz), in the presence of an ipsilateral or contralateral sound. An assessment that may be output to a user based on this test battery includes, for example, the risks of one or more types of middle-ear dysfunction and the risk of auditory neuropathy. In addition, combining MEMR results using ipsilateral and contralateral activators provides information on risks of eighth nerve lesions.

As described herein, the results of an acoustic reflectance test 502 may be combined with one or more ear canal measurement tests to provide an auditory assessment of a patient. For example, such ear canal measurement tests may include an acoustic test to determine the volume of air enclosed between the tip of the probe used in the reflectance test and the eardrum 524, an acoustic test to determine the cross-sectional area at two or more positions along the axis of the ear canal 522, and an acoustic test to determine the length of the ear canal between the probe tip and the eardrum 520.

In one embodiment, the acoustic test of ear-canal cross-sectional area 522 may be calculated as the ratio of the volume of enclosed air to the length of the ear canal between the probe tip and eardrum. The acoustic test of volume of air between probe and eardrum 524 is useful in this regard and may also be used in an alternate embodiment to compensate tympanometric responses for the effect of ear-canal volume, and used to estimate acoustic responses at the eardrum.

Figure 9:
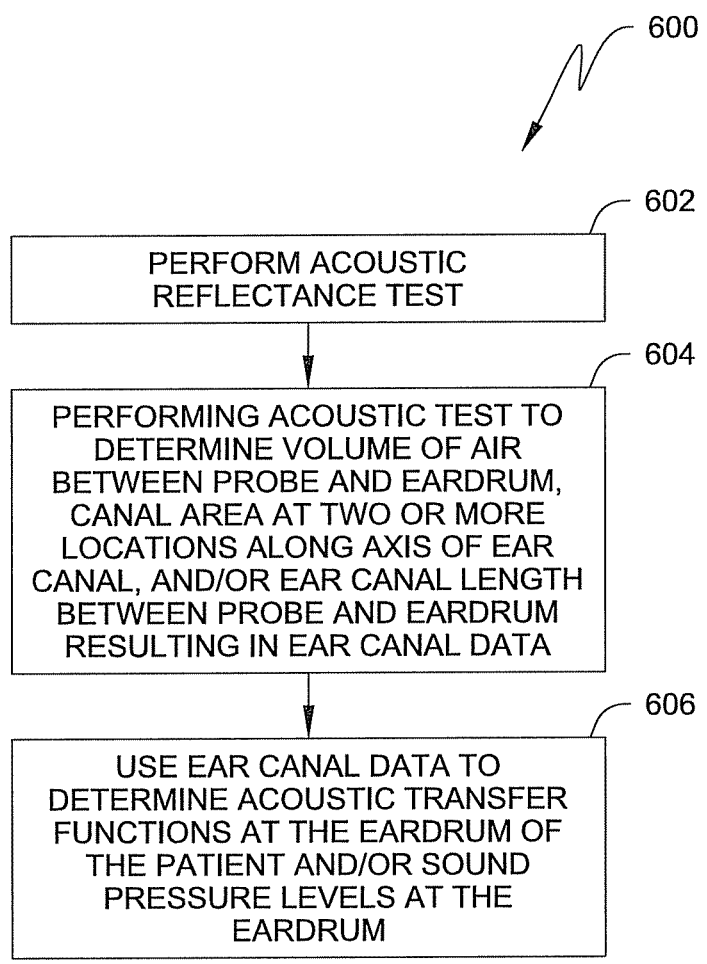
FIG. 9 is a flow diagram showing one embodiment of a test battery method including the use of an acoustic reflectance test and the use of ear canal measurements that may be implemented using the test battery system shown in FIG. 1 according to the present invention.

FIG. 9 shows one embodiment of a method 600 for using one or more of the ear canal measurement tests (e.g., volume test 524, cross-sectional area test 522, and ear canal length test 520). As shown therein, an acoustic reflectance test 502 is performed (block 602). Further, one or more the ear canal measurements are carried out resulting in ear canal data (block 604). Thereafter, such ear canal data is used to determine an acoustic transfer function at the eardrum of the patient and/or sound pressure levels at the eardrum (block 606).

For example, and further with regard thereto, in one or more further embodiments, the results of one or more of the ear canal measurement tests may be used to estimate sound pressure level, acoustic admittance, and acoustic reflectance at the eardrum, as well as sound power or sound intensity absorbed at the eardrum, as opposed to at the tip of the probe. Such ear canal measurement results allow the system to perform a non-invasive test using a single measurement in the ear canal to obtain estimates of the measurements at the eardrum. As such, the ear canal measurements are useful in a single system combined with any of the other tests described herein. This acoustic test of eardrum response based on probe response 526 depends on a determination of the acoustic test of ear canal length 520.

In another embodiment, an acoustic test of ear canal cross-sectional area 522 may be useful in converting admittance measurements to reflectance measurements. Such measurements may also include a more complete measurement of the cross-sectional area at more than one location between the probe tip and eardrum along the ear canal axis. These multiple measurements along the axis may be used in assessing the high-frequency effects of variations in ear canal cross-sectional area on the accuracy of the acoustic test of eardrum response based on probe response 526.

Yet further, in one or more embodiments, when analyzed together, the results of a test battery including an acoustic reflectance test 502 at the probe tip and an ear canal measurement test may be used to calculate at the eardrum the sound pressure level and phase and such acoustic transfer functions as acoustic reflectance and acoustic admittance. An output that may result from such a combination of tests may include, for example, an estimate of the acoustic admittance at the eardrum, which, for normal-hearing subjects, is similar to transfer functions of velocity on the tympanic membrane to sound pressure level at the eardrum, which are obtained using laser Doppler vibrometry systems. These relationships are described in an abstract by DH Keefe (2005), "Using reflectance phase to estimate the acoustic response at the tympanic membrane, *J. Acoust. Soc. Am.* 115, 2499(A). Such tests in a single device may be used to screen and diagnose middle-ear dysfunction or in combination with other tests of peripheral auditory system dysfunction.

Figure 10A:
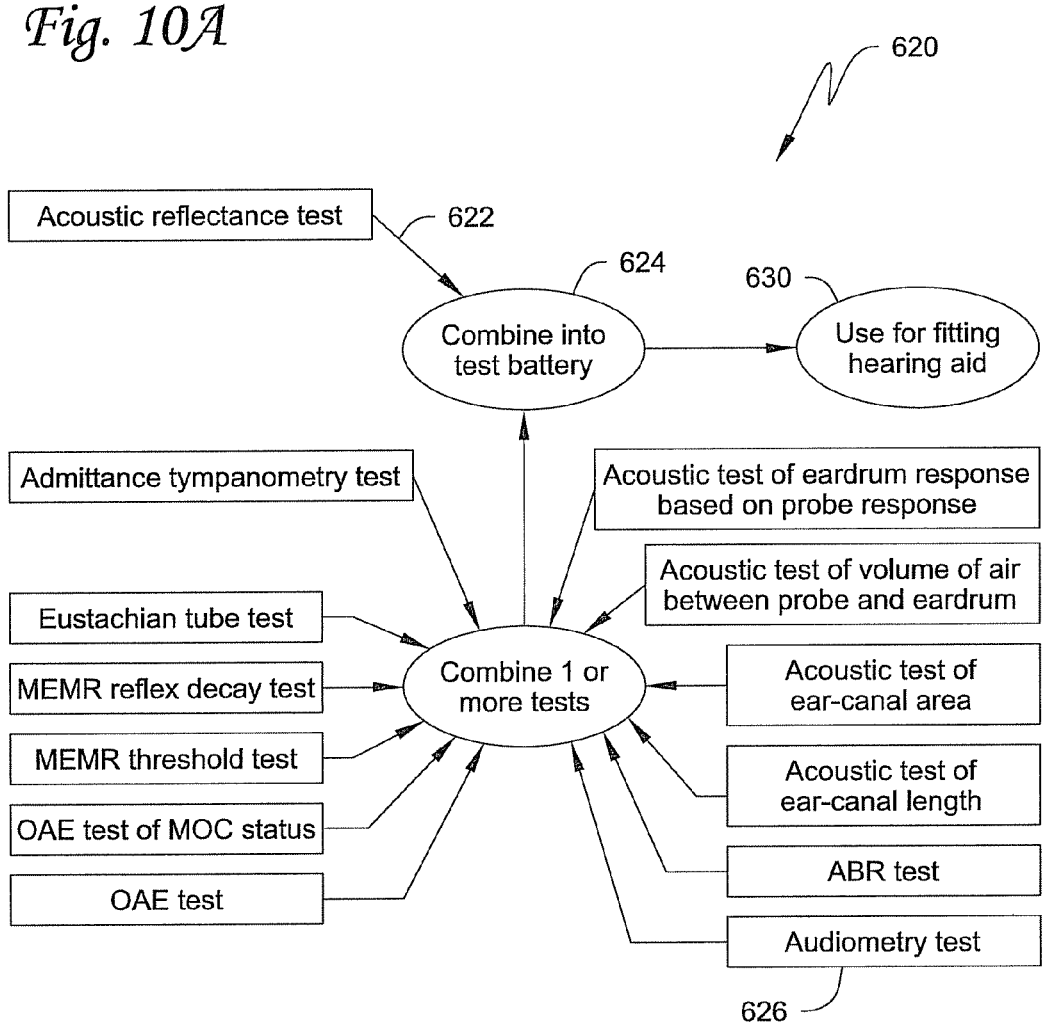
FIG. 10A is a flow diagram showing one embodiment of a test battery method including the use of an acoustic reflectance test for use in fitting a hearing aid that may be implemented using the test battery system shown in FIG. 1, or that shown in FIG. 3 with one or more modifications.

As shown in the flow diagram of the test battery method 620 of FIG. 10A, in addition to assessing a patient auditory system through, for example, diagnosis or screening, the results of acoustic reflection test 622 may be used alone or in combination (circle 624) with one or more other auditory tests (see, for example, the other tests shown in FIG. 8 and again in FIG. 10A) for use in fitting a hearing aid (block 630).

The signal processing elements of a hearing aid circuit (not shown) might include such parameters as those controlling automatic gain control, linear amplification, compression limiting, wide dynamic range compression, and syllabic compression, including modification of the attack and release times of the hearing aid, and are described in Levitt H. (2004), "Compression Amplification", Chapter 5 in "Compression: from Cochlea to Cochlear Implants", Editors, Bacon S P, Fay R R and Popper A N (Springer-Verlag, New York). These parameters may be adjusted based on a battery of tests described herein.

For example, using results from the acoustic response (e.g., a response from an acoustic reflectance test), signal processing elements of the hearing aid may be used to adjust one or more parameters of such elements to modify functions of the hearing aid, including, but clearly not limited to, automatic gain control in the hearing aid, linear amplification in the hearing aid, compression limiting in the hearing aid, wide dynamic range compression in the hearing aid, and syllabic compression in the hearing aid. Further, for example, modification of the attack and release times of the hearing aid may also be adjusted based on such an acoustic response.

A transient conductive hearing loss might be created based upon a transient middle-ear dysfunction, such as in otitis media (including middle-ear effusion) and an eardrum perforation. Otitis media is common in young children, and the presence of otitis media in a patient using a hearing aid, if undetected, may lead to inadequate amplification in the child's hearing aid. A more permanent conductive hearing loss might be created based on such middle-ear dysfunction as an ossicular discontinuity, fixed ossicle in the ossicular chain, or otosclerosis, unless corrected for my middle-ear surgery.

The ability of a hearing diagnostic test using an acoustic response (e.g., a response of an acoustic reflectance test) to detect middle-ear dysfunction and conductive hearing loss might be used to make changes in the signal processing elements of a patient's hearing aid, which are otherwise set to rehabilitate the presence of a sensorineural hearing loss alone. In such a manner, the effects of the middle-ear dysfunction or conductive hearing loss on the patient using the hearing aid might thereby be ameliorated.

Generally, or at least in partial summary of the usefulness of, for example, an acoustic reflectance test in the fitting of a hearing aid, any adjustment in parameters of a hearing aid may be made that are intended to compensate for any effects of middle-ear dysfunction. Middle-ear dysfunction includes, for example, otitis media, eardrum perforation, ossicular discontinuity, a fixed ossicle in the ossicular chain and/or otosclerosis. Such a middle-ear dysfunction may lead to a conductive hearing loss.

It will be recognized that such a hearing diagnostic test could be part of a hearing aid fitting method that is external to the hearing aid or could be included as part of the hearing aid itself to provide a real-time hearing fitting test. For example, the hearing aid may incorporate components to perform an ambient-pressure reflectance test (e.g., may include at least one acoustic transducer to measure an acoustic response in the ear) and automatically (i.e., in real time) make a correction to parameters of the hearing aid. This correction would be performed if the risk assessment output by the test battery is that a conductive hearing loss associated with otitis media with effusion is likely. The hearing-aid amplification, compression and attack and release times may be adjusted based on an estimate of the likely conductive hearing loss, which may add to the sensorineural hearing loss that was previously estimated at the time the hearing aid was fitted and for which the hearing-aid parameters were previously adjusted.

Yet further, in another embodiment, the hearing aid may include circuitry for transmitting a warning signal to a health care practitioner upon the occurrence of one or more events detected by a hearing aid that incorporates components for performing one or more tests as described herein. For example, a warning signal may be issued if the acoustic reflectance test detects a probable middle-ear dysfunction or conductive hearing loss.

Figure 10B:
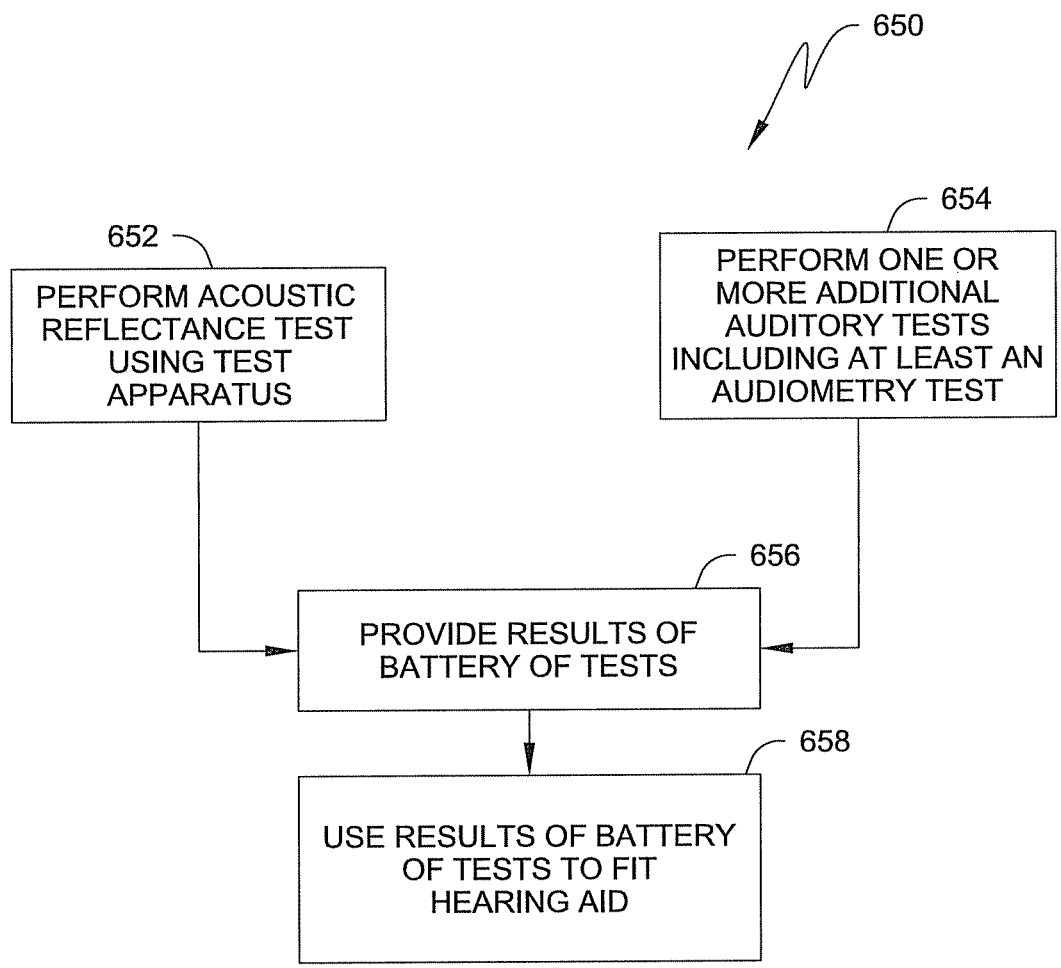
FIG. 10B is a flow diagram showing one embodiment of a test battery method including the use of an acoustic reflectance test and at least one audiometry test that may be implemented using the test battery system shown in FIG. 1, or that shown in FIG. 3 with one or more modifications.

In one embodiment, as shown in the hearing aid fitting method 650 of FIG. 10B, the results of an acoustic reflectance test (block 652) is provided in combination with results of one or more auditory tests including at least one audiometry test (block 654). The results of the battery of such tests (block 656) are used to fit a hearing aid (block 658).

For example, in one embodiment, the estimates of responses (e.g., acoustic reflectance) at the eardrum have particular relevance in combination with results at high frequencies of an audiometry test 516 and in the fitting of a hearing aid at high frequencies to an individual ear. For example, the test battery method may include measuring at least one of sound pressure level and an acoustic transfer function at the eardrum as an eardrum test estimate using one or more of the ear canal measurement tests (e.g., ear canal length). In one embodiment, for example, the eardrum test estimate is based on measurements at the probe tip located in the ear canal some distance away from the eardrum and an estimate at the eardrum is made using at least one of the ear canal measurements (e.g., ear canal length). The one or more audiometry test results may then be interpreted with respect to the eardrum test estimate to control for acoustic standing wave effects that otherwise hinder the interpretation of audiology data at high frequencies in the ear canal. Appropriate adjustments to one or more parameters of the hearing aid may effectively be made.

Yet further, in other embodiments, a test battery including an acoustic reflectance and audiometry test may be combined with the hearing-aid programming device that adjusts the hearing-air parameters based on the configuration of sensorineural hearing loss and any presence of middle-ear dysfunction. Such a device incorporating this test battery may also include single-frequency or wideband tympanometry.

As described herein, the results of an acoustic reflectance test and an ABR test may be combined to provide an auditory assessment of a patient. In one or more embodiments, when analyzed together, the results of a test battery including an acoustic reflectance test and an ABR test may show individual risk assessments for middle-ear dysfunction and neural loss, and the risk for a combined middle-ear dysfunction and neural loss, with such risk assessments based on the probabilities of each impairment. An output that may result from such a combination of tests may include, for example, the set of risk assessments.

As described herein, the results of an acoustic reflectance test and an OAE test may be combined to provide an auditory assessment of a patient. In one or more embodiments, when analyzed together, the results of a test battery including an acoustic reflectance test and an OAE test may show individual risk assessments for middle-ear dysfunction and cochlear dysfunction, and the risk for a combined middle-ear dysfunction and cochlear dysfunction. An output that may result from such a combination of tests may include, for example, the set of risk assessments.

As described herein, the results of an acoustic reflectance test and an OAE test of MOC status may be combined to provide an auditory assessment of a patient. In one or more embodiments, when analyzed together, the results of a test battery including an acoustic reflectance test and an OAE test of MOC status may show individual risk assessments for middle-ear dysfunction, cochlear dysfunction and auditory neuropathy, and the risk for a combined middle-ear dysfunction and cochlear dysfunction, the risk for a combined middle-ear dysfunction and auditory neuropathy, and risk for all three impairments. An output that may result from such a combination of tests may include, for example, the set of risk assessments.

As described herein, the results of an acoustic reflectance test 502 and more than one other auditory test may be combined to provide an auditory assessment of a patient. For example, there is a critical need in newborn hearing screening programs to detect sensorineural hearing loss or a test to detect middle-ear dysfunction and to detect auditory neuropathy. A combined system including an acoustic reflectance test 502, an OAE response test 514, and a MEMR threshold test 510 would screen newborn hearing for middle-ear dysfunction, cochlear dysfunction, and auditory neuropathy.

In one embodiment, the MEMR shift can be measured using a conventional MEMR threshold test 510 with single-frequency acoustic admittance. Because of practical difficulties in testing newborn infants, an ipsilateral MEMR test has the advantage that only one ear is tested at a time. The infant is often tested while his or her head is resting on one side, thus covering one ear.

However, such a test battery is also appropriate for clinical use in older children and adults. OAE response tests include, among others, distortion product otoacoustic emission (DPOAE), click-evoked otoacoustic emission, transient evoked otoacoustic emission, and stimulus frequency otoacoustic emission (SFOAE) tests. In many cases, the DPOAE test is the preferred embodiment of the OAE test in a combined system that includes an acoustic reflectance test, a MEMR threshold test, and an OAE test because the DPOAE test is well accepted and used widely by audiologists. Such a combination of tests may also be useful in the screening and diagnostic of peripheral auditory system dysfunction in older children and adults. Such a test battery would provide individual risk assessments for middle-ear dysfunction, cochlear dysfunction and auditory neuropathy, and the risk for a combined middle-ear dysfunction and cochlear dysfunction, the risk for a combined middle-ear dysfunction and auditory neuropathy, and risk for all three impairments. An output that may result from such a combination of tests may include, for example, the set of risk assessments.

The above tests (e.g., an acoustic reflectance test, a MEMR threshold test, and an OAE test) can also be combined with an OAE test of MOC status 512. Preferably, particularly with infants, the OAE test of MOC function uses a wideband noise signal as the ipsilateral activator, so that this test is also performed in a single test ear, and uses the shift induced by the MOC function on a SFOAE response as the indicator of MOC function. An alternative embodiment uses a shift in a DPOAE response or in some other OAE response as the indicator of MOC function. Such a test battery would provide individual risk assessments for middle-ear dysfunction, cochlear dysfunction and auditory neuropathy, and the risk for a combined middle-ear dysfunction and cochlear dysfunction, the risk for a combined middle-ear dysfunction and auditory neuropathy, and risk for all three impairments. The risk assessment for auditory neuropathy would be improved by having two tests predictive of auditory neuropathy, an absent MEMR threshold and an OAE test of MOC function showing absent MOC function. An output that may result from such a combination of tests may include, for example, the set of risk assessments.

An ABR test 518 can also be included in a test battery to assess the neural status of the auditory system. A test battery including at least an acoustic reflectance test with an ABR test, and a MEMR threshold test can be used to screen and diagnose patients for middle-ear dysfunction, sensorineural dysfunction, and auditory neuropathy. Such a test battery would provide individual risk assessments for middle-ear dysfunction, sensorineural hearing loss, and auditory neuropathy, and the risk for a combined middle-ear dysfunction and sensorineural hearing loss, the risk for a combined middle-ear dysfunction and auditory neuropathy, and risk for all three impairments. The risk assessment for auditory neuropathy would be improved by having two tests predictive of auditory neuropathy, an absent MEMR threshold and an abnormal ABR test results. An output that may result from such a combination of tests may include, for example, the set of risk assessments.

Still further, a combined system capable of measuring acoustic reflectance, OAE response, ABR response, and a MEMR shift in the acoustic reflectance may be used to screen and diagnose patients for middle-ear dysfunction, cochlear dysfunction, sensorineural dysfunction, and auditory neuropathy. Such a test battery would provide individual risk assessments for middle-ear dysfunction, cochlear (outer-hair-cell) dysfunction, sensorineural hearing loss, and auditory neuropathy, and the risk associated with all combinations of subsets of the individual tests comprising the test battery. The risk assessment for auditory neuropathy would be improved by having two tests predictive of auditory neuropathy, an absent MEMR threshold and an abnormal ABR test results. An output that may result from such a combination of tests may include, for example, the set of risk assessments.

The combination of these tests provides complementary clinical information on the functioning of the various levels of the auditory system. Acoustic reflectance, MEMR, OAE and ABR response measurements are each influenced by middle-ear functioning, and MEMR, ABR and an OAE test of MOC status are tests that are each sensitive to the presence of auditory neuropathy. This allows cross-validation between tests and increased refinements in screening and diagnosis.

For each test battery system including at least an acoustic reflectance test with a MEMR test and one or both of OAE and ABR measurements, one alternative embodiment includes measuring acoustic reflectance and MEMR shifts without static pressurization. That is, measurements can be performed at ambient pressure. The ambient pressure acoustic reflectance measurements provide significant clinical information on middle-ear function, and thus can be used in any combination with MEMR tests, either threshold or supra-threshold tests, OAE and ABR tests to improve the accuracy of screening and diagnosing hearing pathologies. This may be useful in newborn hearing screening programs in that static pressurization is thought to strongly affect acoustic responses measured in neonatal ear canals. Infants who are referred for follow-up medical evaluation based on the initial newborn hearing screening program may be tested at older ages than approximately three months using a test battery device that includes static pressurization and single-frequency and/or wideband tympanometry.

For an ambient pressure system of these combined measurements, the system of FIG. 3 would be modified by deleting the pump and associated tubing to the probe assembly, the pump control unit, the static pressure transducer and the feedback control circuit.

For test battery systems, and other systems that use reflectance or wideband tympanometry, the reflectance tympanometry is preferably implemented using components such as those shown in FIG. 3. The addition of the feedback control of static pressure in this implementation increases the reliability and accuracy of such acoustic reflectance measurements. By wideband tympanometry is meant the use of measurements across a wide frequency range and a clinically relevant range of static pressures of either sound pressure level or phase, acoustic transfer functions including acoustic reflectance, acoustic transmittance, acoustic admittance and acoustic impedance, or absorbed power. Such wideband tympanometry devices may also perform wideband frequency measurements at a fixed static pressure different from ambient pressure.

Use of MEMR Threshold Test in the Test Battery

Figure 11:
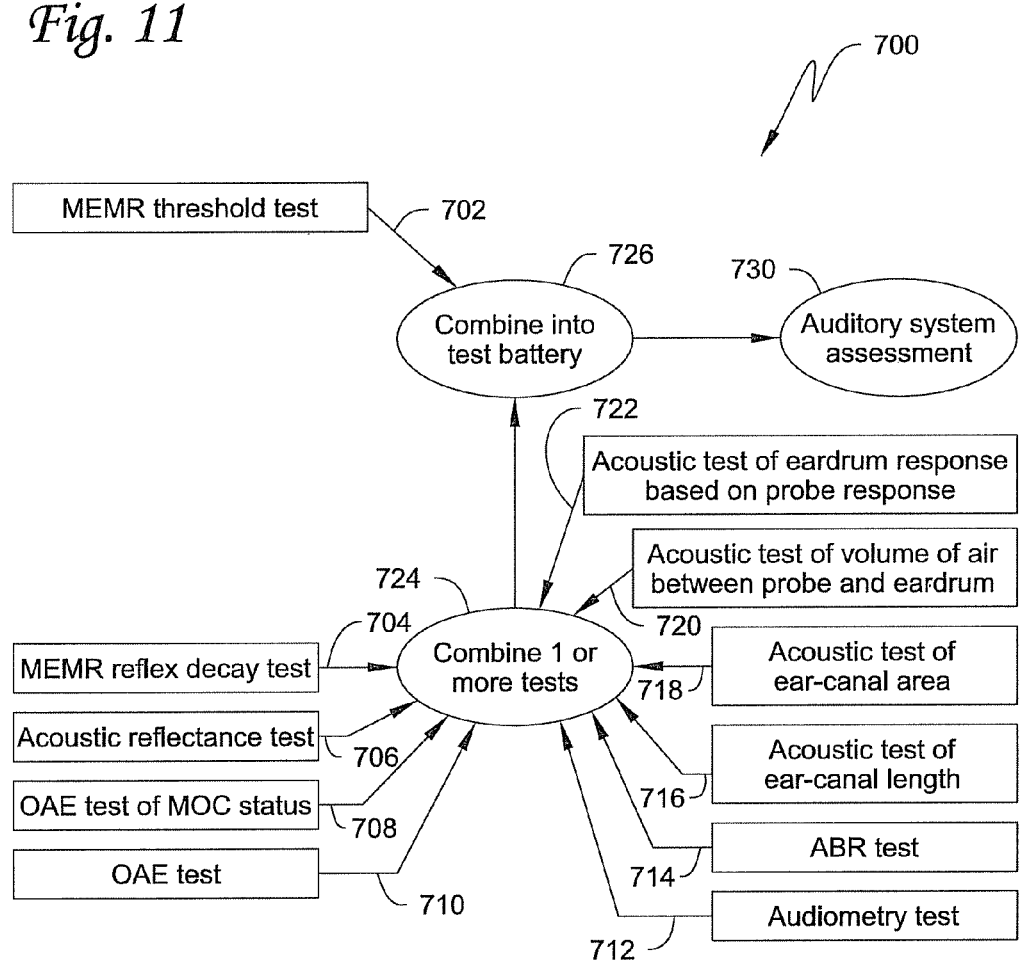
FIG. 11 is a flow diagram showing one embodiment of a test battery method including the use of a middle-ear muscle reflex (MEMR) threshold test that may be implemented using the test battery system shown in FIG. 1, or that shown in FIG. 3 with one or more modifications.

FIG. 11 shows one or more embodiments of a test battery method 700 that combines (circle 726) the results of a MEMR threshold test 702 with the results of one or more other auditory tests for use in auditory system assessment (circle 730) of a patient. As shown in FIG. 11, the test battery includes a MEMR threshold test 702 for use in generating an objective assessment of the auditory system function (e.g., the acoustic reflectance test may or may not be included it the test battery). Further, as shown, the test battery also receives one or more test results from a combination of one or more other auditory tests. This combination of one or more tests includes one or more of the following tests: a MEMR test of reflex decay 704, an OAE test 710, an OAE test of MOC status 708, an acoustic test of eardrum response based on probe response 722 (e.g., such eardrum response including one or more of the acoustic reflectance at the eardrum, the acoustic admittance at the eardrum, and the sound pressure level at the eardrum), an acoustic test of volume of air between probe and eardrum 720, acoustic test of ear-canal cross-sectional area 718, and acoustic test of ear canal length 716, an ABR test 714, and an audiometry test 712.

As described herein, the results of an acoustic reflectance test and an MEMR threshold test may be combined to provide an auditory assessment of a patient and such results and output were provided with reference to FIG. 8.

Further, the results of a MEMR threshold test 702 and an ABR test 714 may be combined to provide an auditory assessment of a patient. In one or more embodiments, when analyzed together, the results of a test battery including a MEMR threshold test 702 and an ABR test 714 may provide individual risk assessments for sensorineural hearing loss and auditory neuropathy, as well as a risk assessment for a conductive deficit (e.g., middle-ear dysfunction) if ABR latencies can be detected and analyzed, and the risk for a combined sensorineural hearing loss and auditory neuropathy. The risk assessment for auditory neuropathy would be improved by having two tests predictive of auditory neuropathy, an absent MEMR threshold and an abnormal ABR test result. An output that may result from such a combination of tests may include, for example, the set of risk assessments.

As described herein, the results of a MEMR threshold test 702 and an OAE test 710 may be combined to provide an auditory assessment of a patient. In one or more embodiments, when analyzed together, the results of a test battery including a MEMR threshold test 702 and an OAE test 710 may provide individual risk assessments for either middle-ear or cochlear dysfunction via an elevated MEMR threshold and low or absent OAEs, and auditory neuropathy via an absent MEMR threshold, and the risk for all combinations of these impairments. Such a risk assessment may identify newborns with OAE responses in the normal range but with auditory neuropathy resulting in an absent MEMR response (i.e., no MEMR threshold present in the range of MEMR activators provided on the device). An output that may result from such a combination of tests may include, for example, the set of risk assessments.

As described herein, the results of a MEMR threshold test 702 and an OAE test of MOC status 708, which includes the OAE test, may be combined to provide an auditory assessment of a patient. In one or more embodiments, when analyzed together, the results of a test battery including a MEMR threshold test 702 and an OAE test of MOC status 708 may provide individual risk assessments for middle-ear dysfunction, cochlear dysfunction and auditory neuropathy, and the risk for a combined middle-ear dysfunction and cochlear dysfunction, the risk for a combined middle-ear dysfunction and auditory neuropathy, and risk for all three impairments. The risk assessment for auditory neuropathy would be improved by having two tests predictive of auditory neuropathy, an absent MEMR threshold and an OAE test of MOC function showing absent MOC function. An output that may result from such a combination of tests may include, for example, the set of risk assessments.

As described herein, the results of a MEMR threshold test 702 and more than one other auditory test may be combined to provide an auditory assessment of a patient. For example, the results of a MEMR threshold test 702 may be combined with an ABR test 714 and an OAE test 710 to provide an auditory assessment of a patient. In one or more embodiments, when analyzed together, the results of such a test battery may provide individual risk assessments for middle-ear dysfunction, cochlear dysfunction, sensorineural hearing loss and auditory neuropathy, and the risks for all subsets of combined test responses. The risk assessment for auditory neuropathy would be improved by having two tests predictive of auditory neuropathy, an absent MEMR threshold and an abnormal ABR test showing evidence of neural asynchrony. An output that may result from such a combination of tests may include, for example, the set of risk assessments.

The above tests (e.g., a MEMR threshold test 702, an OAE test 710, and an ABR test 714) can also be combined with an OAE test of MOC status 708. Outputs that may result from such a combination of tests may provide individual risk assessments for middle-ear dysfunction, cochlear dysfunction, sensorineural hearing loss and auditory neuropathy, and the risks for all subsets of combined test responses. The risk assessment for auditory neuropathy would be improved by having three tests predictive of auditory neuropathy, an absent MEMR threshold, an abnormal OAE test of MOC status, and an abnormal ABR test showing evidence of neural asynchrony. An output that may result from such a combination of tests may include, for example, the set of risk assessments.

For any set of risk assessments output by a test battery, an advantage of having multiple tests of the same underlying pathology is that the confidence of the resulting risk assessment would be qualified by the degree of concurrence in the individual risk assessments. Such a test battery is of particular significance for the widespread practice of newborn hearing screening programs, in which it is important both to reduce the number of false positives, i.e., those newborns referred as at risk for sensorineural hearing loss who are later found not to have such a loss, and reduce the much smaller number of false negatives, i.e., those newborns who are not found at risk for any auditory dysfunction but who are later found to have a sensorineural hearing loss or auditory neuropathy. Providing additional and complementary information on middle-ear functioning may be important in reducing these false-positive and false-negative rates and correctly identifying newborns needing further intervention and rehabilitation.

All patents and references cited herein are incorporated in their entirety as if each were incorporated separately. This invention has been described with reference to illustrative embodiments and is not meant to be construed in a limiting sense. As described herein, one skilled in the art will recognize that various modifications of the illustrative embodiments, as well as additional embodiments to the invention and combinations of various elements and/or steps herein, will be apparent to persons skilled in the art upon reference to this description. It is therefore contemplated that the patent and claims will cover any such modifications or embodiments that may fall within the scope of the present invention, as defined by the accompanying claims.

What is claimed is:

1. A system for use in performing reflectance tympanometry, the system comprising:
    a probe configured to be coupled into an ear canal in a substantially leak-free state, wherein the probe comprises at least one acoustic transmitter to present one or more acoustic stimulus signals into the ear canal, and further wherein the probe comprises at least one acoustic transducer to measure an acoustic response to the one or more acoustic stimulus signals;
    a pump operatively coupled to the probe to vary the static pressure in the ear canal;
    a processing apparatus operable to initiate one or more auditory tests on a patient upon receipt of input from a user, wherein the processing apparatus is operable for use in initiating and controlling performance of a reflectance tympanometry test on the patient using the probe resulting in reflectance tympanometry data comprising at least one or more transfer functions based at least on a response to an acoustic stimulus signal and a calibrated acoustic transfer function;
    a static pressure transducer to detect static pressure in the ear canal; and
    a controller for use in comparing detected actual static pressure in the ear canal to a desired static pressure, wherein the pump is controlled to maintain the desired static pressure in the ear canal based on the comparison.

2. The system of claim 1, wherein the controller is operable to determine that the pump is unable to maintain the desired static pressure, and further wherein the system comprises an output device operable to provide an alert indication to the user that the pump is unable to maintain the desired pressure.

3. The system of claim 1, wherein the processing apparatus is operable for initiating and controlling performance of one or more other auditory tests, and further wherein the one or more other auditory tests comprise at least one of an admittance tympanometry test, an Eustachian tube test, a middle-ear muscle reflex decay test, a middle-ear muscle reflex threshold test, an otoacoustic emission test of medial olivocochlear status, an otoacoustic emission test, an acoustic test of eardrum response based on probe response, an acoustic test of volume of air between the probe and eardrum, an acoustic test of ear canal cross-sectional area, an acoustic test of ear canal length, an auditory brain stem response test, and an audiometry test.

4. The system of claim 3, wherein the processing apparatus is operable to analyze the reflectance tympanometry data and results of the one or more other auditory tests performed on a patient, and further wherein the system comprises an output device to provide an output to the user representative of a probability of an auditory impairment in function of the patient's auditory system.

5. The system of claim 1, wherein the system further includes a handheld enclosure comprising processing means within the handheld enclosure configured for at least initiating one or more tests upon receipt of input from a user; and further wherein the probe is electrically coupled to the processing means within the handheld enclosure.

6. The system of claim 5, wherein the processing means within the handheld enclosure is further configured for communication of information to a base unit, wherein the base unit comprises base unit processing means for use in processing the information.

7. The system of claim 1, wherein the processing apparatus comprises the controller.

8. The system of claim 3, wherein the processing apparatus is operable to initiate and control performance of at least one of the one or more other auditory tests based at least in part on information that has been determined in at least another auditory test.

9. The system of claim 8, wherein the processing apparatus is operable to initiate and control performance of at least one of the one or more other auditory tests based at least on reflectance tympanometry data.

10. The system of claim 3, wherein the one or more other auditory tests comprise at least a middle-ear muscle reflex threshold test.

11. The system of claim 3, wherein the processing apparatus is further operable for initiating and controlling performance of a single frequency admittance tympanometry test for use in determining the volume of air between the probe and the eardrum of the patient.

12. The system of claim 3, wherein the one or more other auditory tests comprise at least an otoacoustic emission test.

13. The system of claim 3, wherein the system further comprises at least one electrode for connection to a patient's scalp, and further wherein the one or more other auditory tests comprise at least at least an auditory brain stem response test using the at least one electrode.

14. The system of claim 3, wherein the one or more other auditory tests comprise at least one audiometry test resulting in audiometry data.

15. A method for use in assessing auditory function, the method comprising:
    providing test system for use in performing reflectance tympanometry, wherein the test system comprises:
        a processing apparatus, wherein the processing apparatus is configured to initiate one or more tests upon receipt of input from a user;
        a probe electrically coupled to the processing apparatus and configured to be acoustically coupled into an ear canal in a substantially leak-free state, wherein the probe comprises at least one acoustic transmitter to present one or more acoustic stimulus signals into the ear canal, and further wherein the probe comprises at least one acoustic transducer to measure an acoustic response to the one or more acoustic stimulus signals;

a pump operatively coupled to the probe to vary the static pressure in the ear canal; and a static pressure transducer to detect static pressure in the ear canal;

performing a reflectance tympanometry test on a patient using the test system, wherein performing the reflectance tympanometry test comprises:

providing a calibrated acoustic transfer function using the probe;

inserting the probe into the ear canal of the patient in a substantially leak-free state;

delivering an acoustic stimulus signal into the ear canal using the at least one acoustic transmitter of the probe;

controlling the static pressure in the ear canal using the pump, wherein controlling the static pressure comprises detecting actual static pressure in the ear canal using the static pressure transducer, comparing the detected static pressure to a desired static pressure, and controlling the pump to maintain the desired static pressure in the ear canal based on the comparison of the desired static pressure to the actual static pressure;

detecting a response to the acoustic stimulus signal using the at least one acoustic transducer of the probe; and providing reflectance tympanometry data based at least on the response to the acoustic stimulus signal and the calibrated acoustic transfer function.

16. The method of claim 15, wherein the method further comprises:

determining that the pump is unable to maintain the desired static pressure; and providing an alert indication to the user that the pump is unable to maintain the desired pressure.

17. The method of claim 15, wherein the test system is operable to perform and the method comprises performing one or more other auditory tests, wherein the one or more other auditory tests comprise at least one of an admittance tympanometry test, an Eustachian tube test, a middle-ear muscle reflex decay test, a middle-ear muscle reflex threshold test, an otoacoustic emission test of medial olivocochlear status, an otoacoustic emission test, an acoustic test of eardrum response based on probe response, an acoustic test of volume of air between the probe and eardrum, an acoustic test of ear canal cross-sectional area, an acoustic test of ear canal length, an auditory brain stem response test, and an audiometry test.

18. The method of claim 17, wherein the method further comprises:

analyzing the reflectance tympanometry data and results of the one or more other auditory tests performed on a patient using the test system; and providing an output to the user representative of a probability of an auditory impairment in function of the patient's auditory system.

19. The method of claim 17, wherein performing one or more other auditory tests on the patient comprises initiating and controlling performance of at least one of the one or more other auditory tests based at least in part on information that has been determined in at least another auditory test.

20. The method of claim 19, wherein initiating and controlling performance of at least one of the one or more other auditory tests based at least in part on information that has been determined in at least another auditory test comprises initiating and controlling performance of at least one of the one or more other auditory tests based at least in part on reflectance tympanometry data.

21. The method of claim 17, wherein performing one or more other auditory tests on the patient comprises performing a middle-ear muscle reflex threshold test.

22. The method of claim 17, wherein performing one or more other auditory tests on the patient comprises performing at least an otoacoustic emission test.

* * * * *